(12) United States Patent
Park et al.

(10) Patent No.: US 10,439,144 B2
(45) Date of Patent: Oct. 8, 2019

(54) ORGANIC COMPOUND FOR ELECTRONIC DEVICE COMPRISING FUSED-CORE STRUCTURE, ORGANIC OPTOELECTRONIC DEVICE COMPRISING SAME, AND DISPLAY DEVICE

(71) Applicant: UNIVERSITY-INDUSTRY COOPERATION GROUP OF KYUNG HEE UNIVERSITY, Yongin-si (KR)

(72) Inventors: JongWook Park, Seoul (KR); JaeHyun Lee, Seoul (KR)

(73) Assignee: UNIVERSITY-INDUSTRY COOPERATEON GROUP OF KYUNG HEE UNIVERSITY, Yongin-si (KR)

( * ) Notice: Subject to any disclaimer, the term of this patent is extended or adjusted under 35 U.S.C. 154(b) by 0 days.

(21) Appl. No.: 15/509,892

(22) PCT Filed: Jan. 14, 2015

(86) PCT No.: PCT/KR2015/000395
§ 371 (c)(1),
(2) Date: Jul. 19, 2017

(87) PCT Pub. No.: WO2016/039510
PCT Pub. Date: Mar. 17, 2016

(65) Prior Publication Data
US 2017/0338416 A1    Nov. 23, 2017

(30) Foreign Application Priority Data
Sep. 12, 2014    (KR) .................. 10-2014-0121222

(51) Int. Cl.
*H01L 51/00*    (2006.01)
*C07D 209/82*    (2006.01)
(Continued)

(52) U.S. Cl.
CPC .......... *H01L 51/0056* (2013.01); *C07C 13/72* (2013.01); *C07C 211/54* (2013.01);
(Continued)

(58) Field of Classification Search
CPC ..... C07C 13/72; C07C 211/54; C07C 211/61; C07D 209/56; C07D 209/86;
(Continued)

(56) References Cited

U.S. PATENT DOCUMENTS

2011/0204354 A1* 8/2011 Sekiguchi ............... C07C 13/62
                                                                  257/40
2014/0159024 A1* 6/2014 Takada ................. C07D 401/04
                                                                  257/40

FOREIGN PATENT DOCUMENTS

JP    2013-041893        2/2013
JP    2013247179 A   * 12/2013
KR    10-2014-0045377    4/2014

OTHER PUBLICATIONS

G.T. Ventura et al., The composition, origin and fate of complex mixtures in the maltene fractions of hydrothermal petroleum assessed by comprehensive two-dimensional gas chromatography, Organic Geochemistry 45 (2012) 48-65. (Year: 2012).*
(Continued)

*Primary Examiner* — Daniel P Shook
(74) *Attorney, Agent, or Firm* — Lex IP Meister, PLLC

(57) ABSTRACT

The present invention relates to: an organic compound represented by a combination of Chemical Formulas 1 and 2; an organic optoelectronic device comprising the organic compound; and a display device.
(Continued)

[Chemical Formula 1]

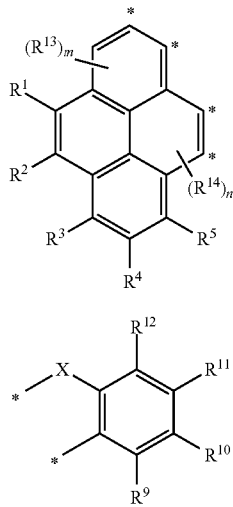

[Chemical Formula 2]

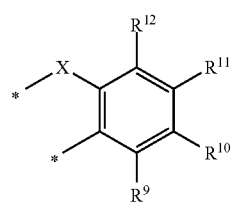

8 Claims, 10 Drawing Sheets

(51) Int. Cl.
| | |
|---|---|
| *C07C 13/72* | (2006.01) |
| *C07D 307/91* | (2006.01) |
| *C07C 211/54* | (2006.01) |
| *C07C 211/61* | (2006.01) |
| *C07D 209/56* | (2006.01) |
| *C07D 209/86* | (2006.01) |
| *C07D 209/88* | (2006.01) |
| *C07D 251/24* | (2006.01) |
| *C07D 307/77* | (2006.01) |
| *C07D 333/50* | (2006.01) |
| *C07D 403/14* | (2006.01) |
| *C07D 405/04* | (2006.01) |
| *C07D 409/04* | (2006.01) |
| *C09K 11/06* | (2006.01) |
| *H05B 33/14* | (2006.01) |
| *H01L 51/50* | (2006.01) |

(52) U.S. Cl.
CPC .......... *C07C 211/61* (2013.01); *C07D 209/56* (2013.01); *C07D 209/82* (2013.01); *C07D 209/86* (2013.01); *C07D 209/88* (2013.01); *C07D 251/24* (2013.01); *C07D 307/77* (2013.01); *C07D 307/91* (2013.01); *C07D 333/50* (2013.01); *C07D 403/14* (2013.01); *C07D 405/04* (2013.01); *C07D 409/04* (2013.01); *C09K 11/06* (2013.01); *H01L 51/0054* (2013.01); *H01L 51/0058* (2013.01); *H01L 51/0067* (2013.01); *H01L 51/0072* (2013.01); *H01L 51/0073* (2013.01); *H01L 51/0074* (2013.01); *H05B 33/14* (2013.01); *C07C 2603/18* (2017.05); *C07C 2603/24* (2017.05); *C07C 2603/26* (2017.05); *C07C 2603/48* (2017.05); *C07C 2603/50* (2017.05); *C07C 2603/90* (2017.05); *C07C 2603/94* (2017.05); *C09K 2211/1011* (2013.01); *C09K 2211/1014* (2013.01); *C09K 2211/1018* (2013.01); *C09K 2211/1022* (2013.01); *H01L 51/006* (2013.01); *H01L 51/5012* (2013.01)

(58) Field of Classification Search
CPC .. C07D 209/88; C07D 251/24; C07D 307/77; C07D 333/50; C07D 405/04; C07D 409/04; C07D 2603/94; C09K 11/06; H01L 51/0056; H01L 51/006; H01L 51/0067; H01L 51/0072–51/0074; H01L 51/5012

See application file for complete search history.

(56) References Cited

OTHER PUBLICATIONS

Jinchong Xiao et al., "Synthesis, Characterization, Self-Assembly, and Physical Properties of 11-Methylbenzo[d]pyreno[4,5-b]furan", Organic Letters, vol. 13, No. 12, May 19, 2011, pp. 3004-3007.

H. Surya Prakash Rao and Satish Vijjapu, "Synthesis and photochromic properties of benzofuran-phenanthrene and benzofuran-pyrene hybrids", The Royal Society of Chemistry Advance, vol. 4, Apr. 30, 2014, pp. 25747-25758.

* cited by examiner

ORGANIC COMPOUND FOR ELECTRONIC DEVICE COMPRISING FUSED-CORE STRUCTURE, ORGANIC OPTOELECTRONIC DEVICE COMPRISING SAME, AND DISPLAY DEVICE

BACKGROUND OF THE INVENTION

(a) Field of the Invention

An organic compound, an organic optoelectronic device including the same, and a display device are disclosed.

The present invention is derived from research conducted as one of industrial fusion original technology development projects by Ministry of Trade, Industry, and Energy and Korea Evaluation Institute of Industrial Technology (Project No.: 10042590, Title: Development of material for 50 inch UD level next generation OLED TV using super hybrid composite process) and research conducted as one of senior researcher support projects by Ministry of Education, Science, and Technology and National Research Foundation of Korea (Project No: 2012001846, Title: Future π electronic material system research using molecular precise control fusion technique).

(b) Description of the Related Art

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, and an organic solar cell.

Of these, the organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. A light emitting wavelength and performance of an organic light emitting diode may be affected by characteristics of the organic layer, and among them, may be mainly affected by characteristics of an organic material of the organic layer.

SUMMARY OF THE INVENTION

Technical Object

An embodiment provides a compound applicable to an organic optoelectronic device.

Another embodiment provides an organic optoelectronic device including the compound.

Yet another embodiment provides a display device including an organic light emitting diode of the organic optoelectronic device.

Technical Solution

According to an embodiment, an organic compound represented by a combination of Chemical Formulas 1 and 2 is provided.

[Chemical Formula 1]

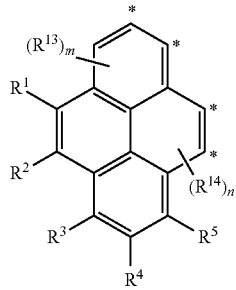

[Chemical Formula 2]

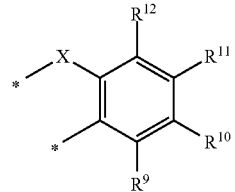

In Chemical Formulas 1 and 2, $R^1$ to $R^5$ and $R^9$ to $R^{14}$ are independently hydrogen, deuterium, a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, X is —$CR^aR^b$—, —$NR^c$—, —O—, —S—, —Si—, or —$PR^d$—, wherein $R^a$ to $R^d$ are independently hydrogen, deuterium, a substituted or unsubstituted amine group, a substituted or unsubstituted C1 to C30 alkyl group, a substituted or unsubstituted C6 to C30 aryl group or a substituted or unsubstituted C2 to C30 heteroaryl group or Ra and Rb are linked with each other to form a fused ring, m is an integer of 1 or 3, n is an integer of 0 or 2, and two *'s of Chemical Formula 2 are bound to adjacent two of four *'s of Chemical Formula 1 to form a fused ring.

The organic compound may be represented by Chemical Formula 3.

[Chemical Formula 3]

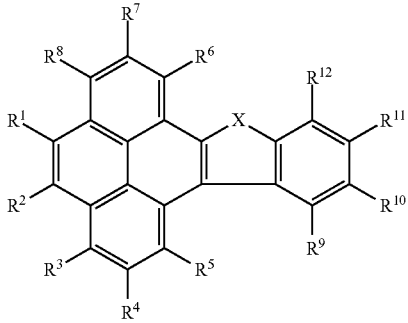

In Chemical Formula 3, $R^1$ to $R^{12}$ are independently hydrogen, deuterium, a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, provided that R6 to R8 are the same, X is —CR$^a$R$^b$—, —NR$^c$—, —O—, —S—, —Si—, or —PR$^d$—, wherein R$^a$ to R$^d$ are independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heteroaryl group or R$^a$ and R$^b$ are linked with each other to form a fused ring.

In Chemical Formula 3, at least one of R$^1$ and R$^2$ may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof. For example, one of R1 and R2 may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof and the other may be hydrogen.

In Chemical Formula 3, at least one of R$^9$ to R$^{12}$ may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof. For example, one of R9 to R12 may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof and the other three may be hydrogen.

In Chemical Formula 3, X may be —CR$^a$R$^b$—, —NR$^c$—, —O—, or —S—, wherein R$^a$ to R$^c$ are independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heteroaryl group or R$^a$ and R$^b$ are linked with each other to form a fused ring.

The organic compound may be represented by one of Chemical Formulas 4-1 to 4-38, 5-1 to 5-49, 6-1 to 6-37, and 7-1 to 7-37.

[Chemical Formula 4-1]

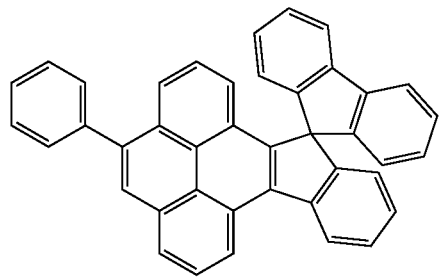

[Chemical Formula 4-2]

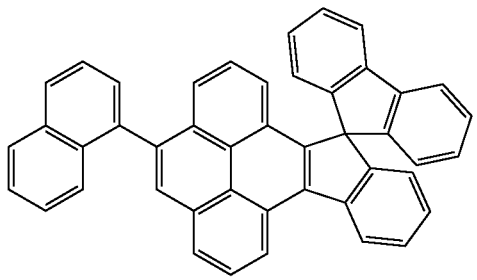

[Chemical Formula 4-3]

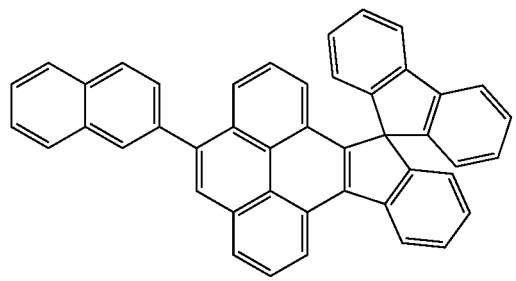

[Chemical Formula 4-4]

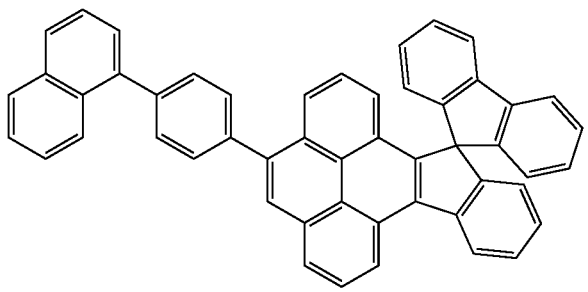

[Chemical Formula 4-5]

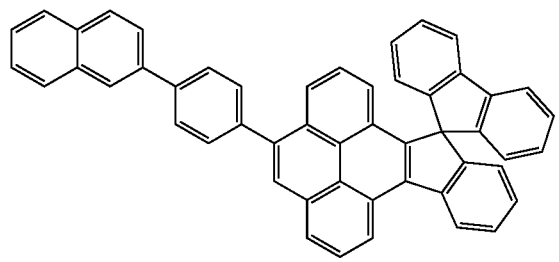

[Chemical Formula 4-6]

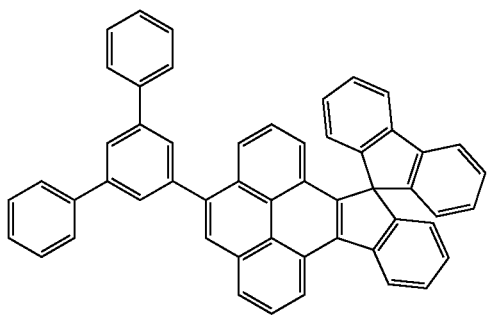

[Chemical Formula 4-7]
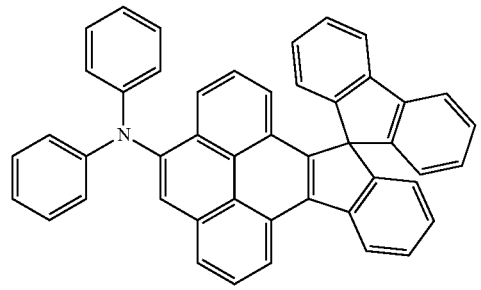
[Chemical Formula 4-8]
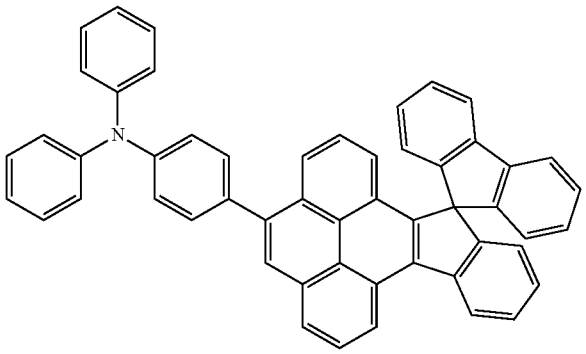
[Chemical Formula 4-9]
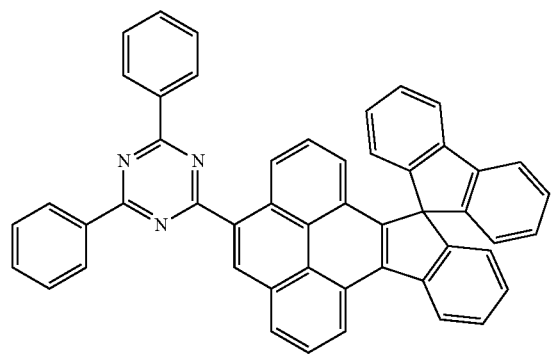
[Chemical Formula 4-10]
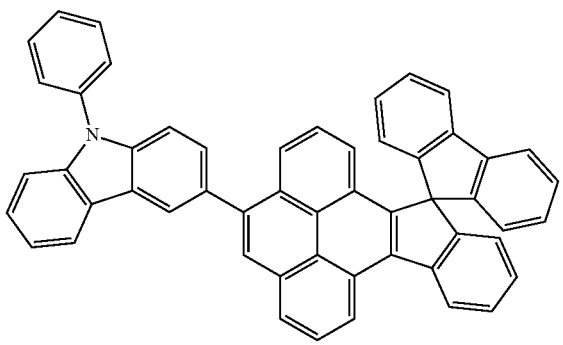
[Chemical Formula 4-11]
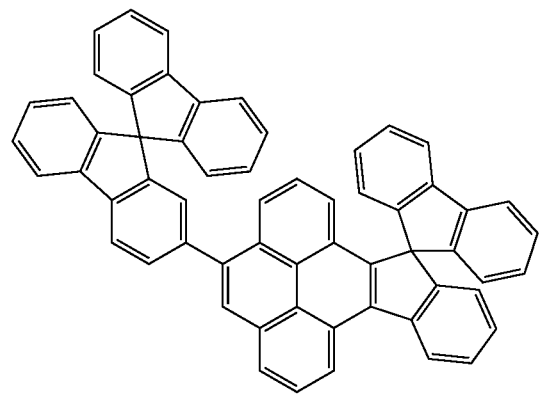
[Chemical Formula 4-12]
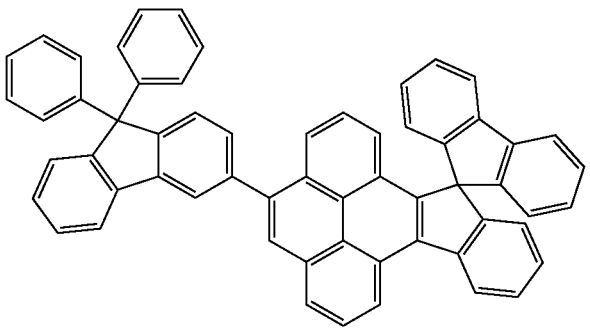
[Chemical Formula 4-13]
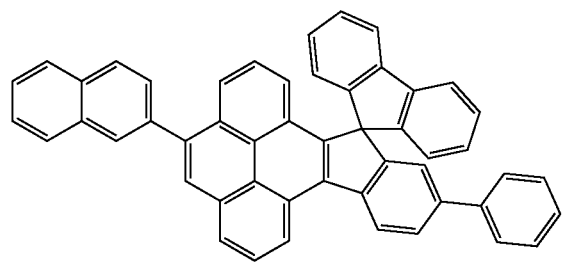
[Chemical Formula 4-14]
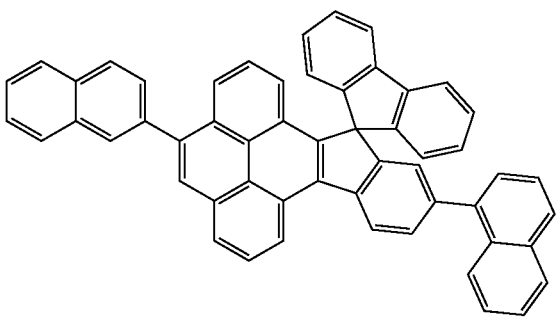

-continued
[Chemical Formula 4-15]
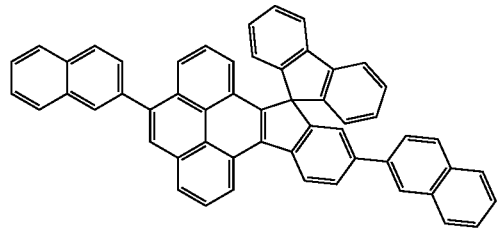
[Chemical Formula 4-16]
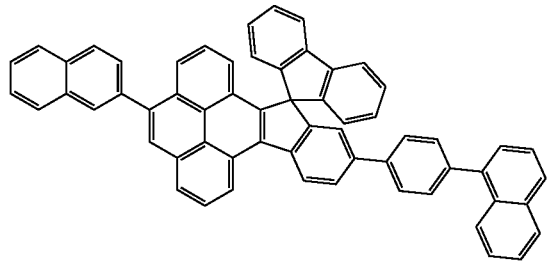
[Chemical Formula 4-17]
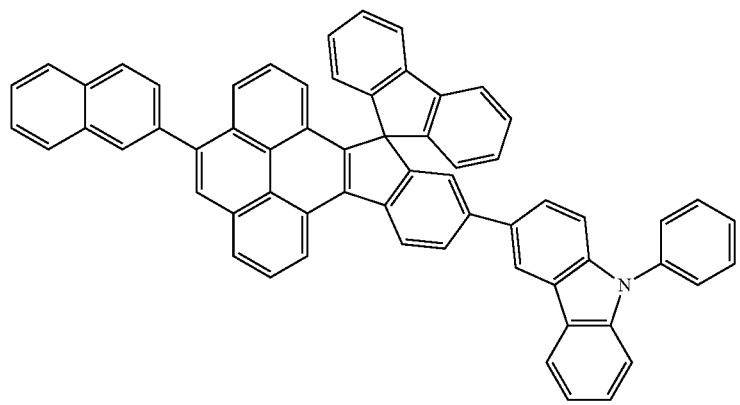
[Chemical Formula 4-18]
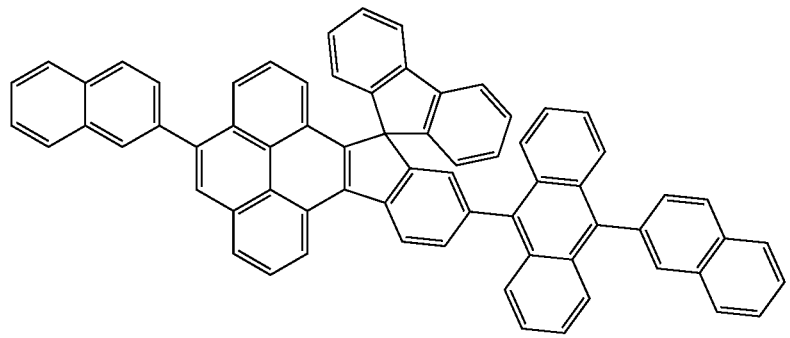
[Chemical Formula 4-19]
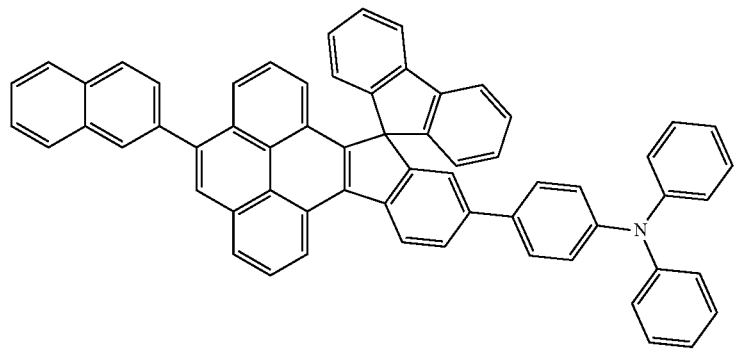

[Chemical Formula 4-20]
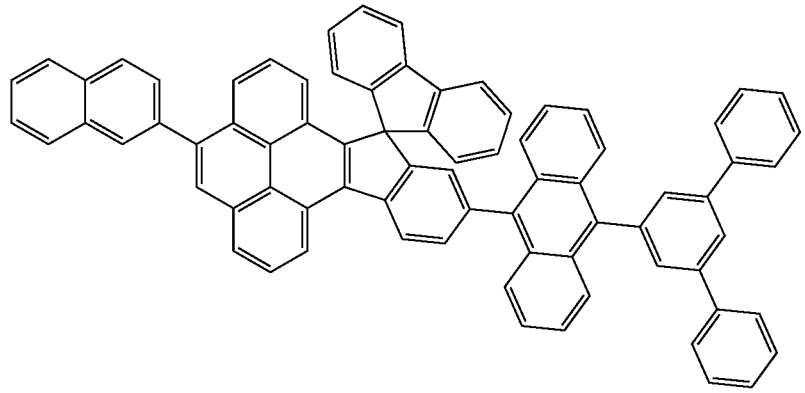
[Chemical Formula 4-21]
[Chemical Formula 4-22]
[Chemical Formula 4-23]
[Chemical Formula 4-24]
[Chemical Formula 4-25]
[Chemical Formula 4-26]

[Chemical Formula 4-27]
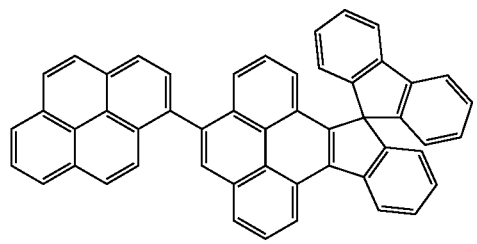
[Chemical Formula 4-28]
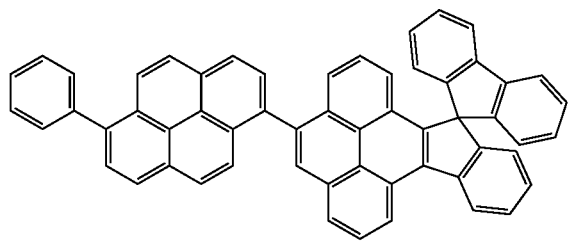
[Chemical Formula 4-29]
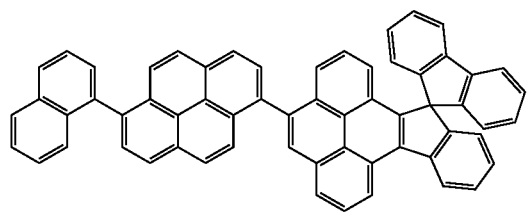
[Chemical Formula 4-30]
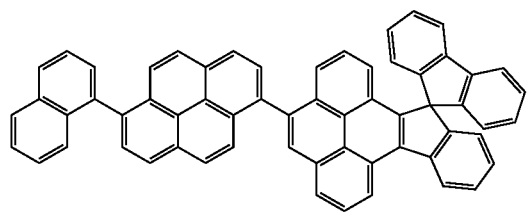
[Chemical Formula 4-31]
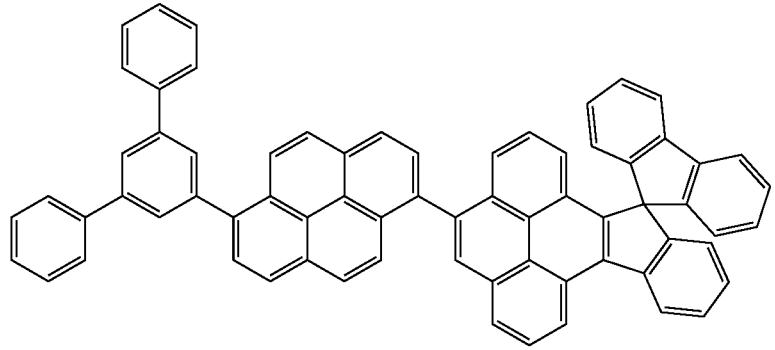
[Chemical Formula 4-32]
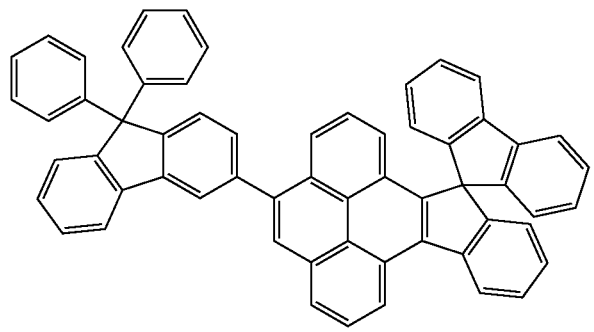
[Chemical Formula 4-33]
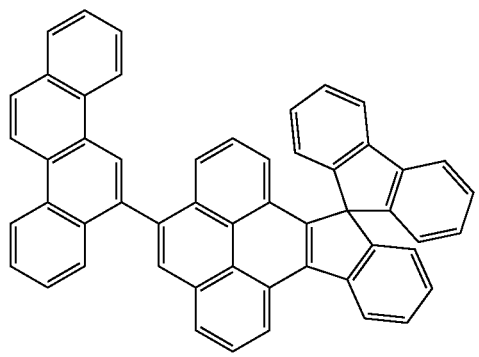
[Chemical Formula 4-34]
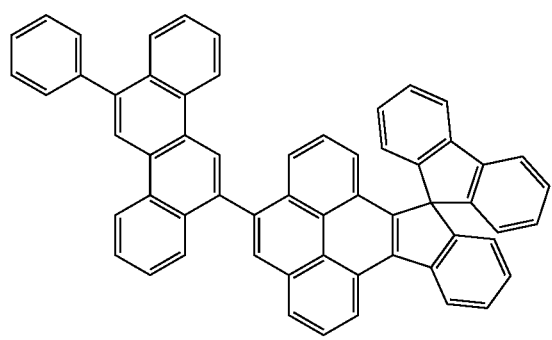
[Chemical Formula 4-35]
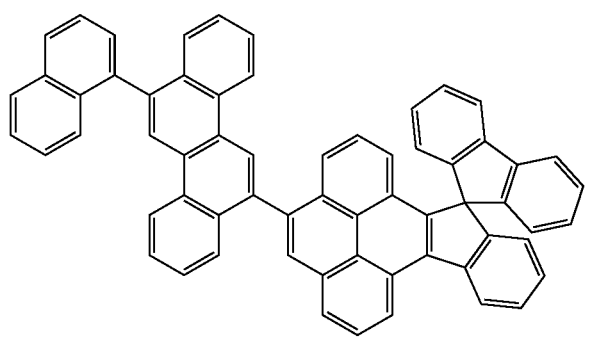

-continued
[Chemical Formula 4-36]
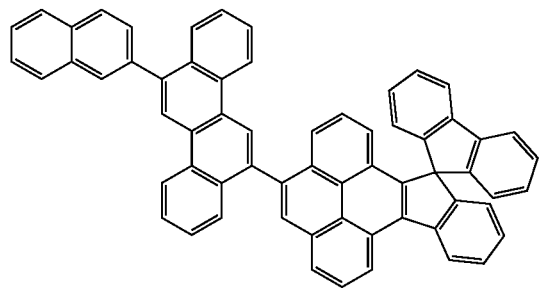
[Chemical Formula 4-37]
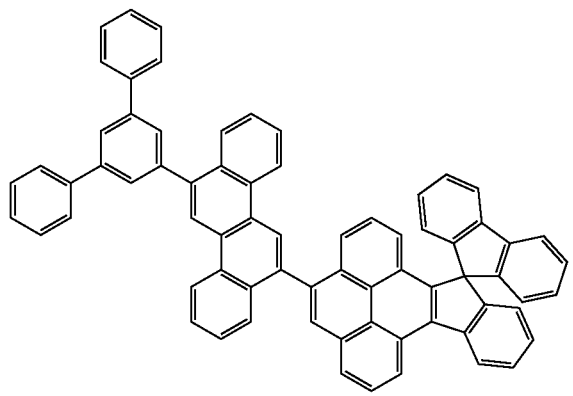
[Chemical Formula 4-38]
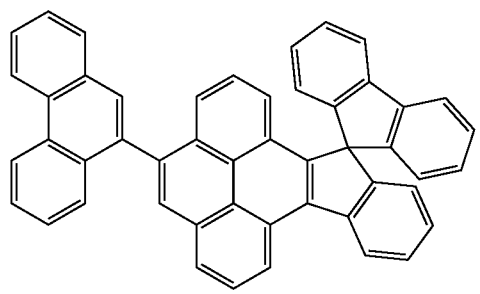
[Chemical Formula 5-1]
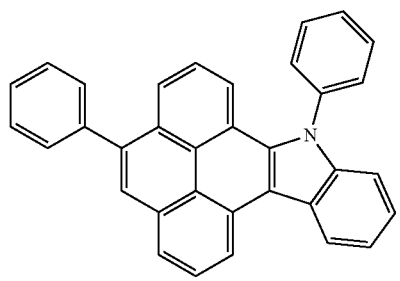
[Chemical Formula 5-2]
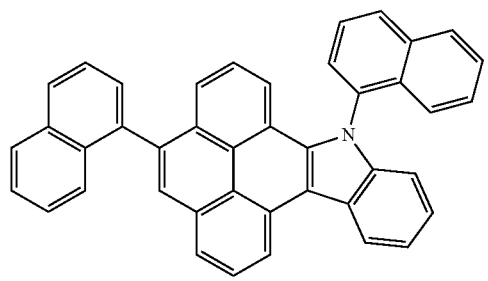
[Chemical Formula 5-3]
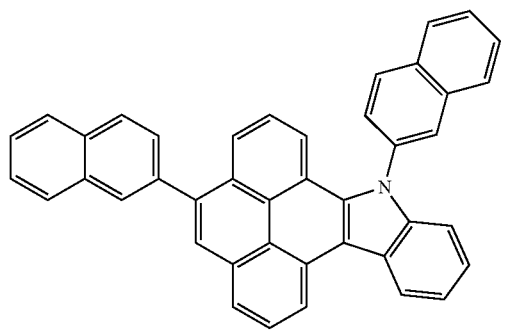
[Chemical Formula 5-4]
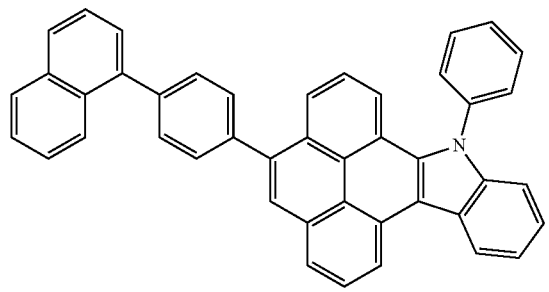
[Chemical Formula 5-5]
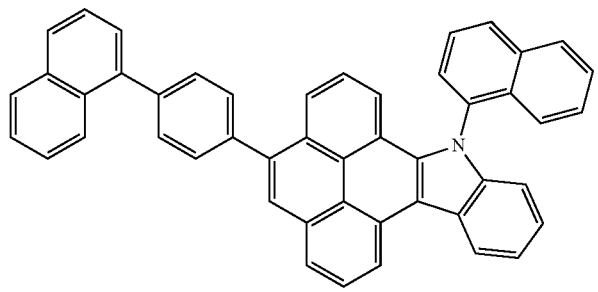

-continued
[Chemical Formula 5-6]
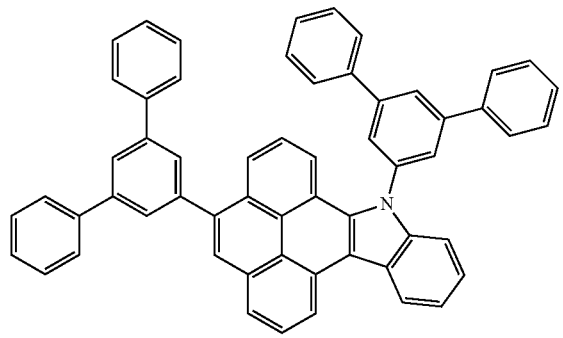
[Chemical Formula 5-7]
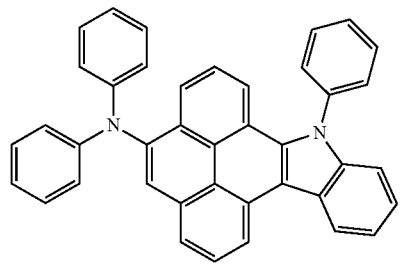
[Chemical Formula 5-8]
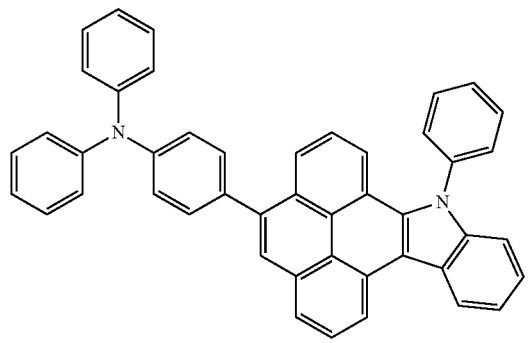
[Chemical Formula 5-9]
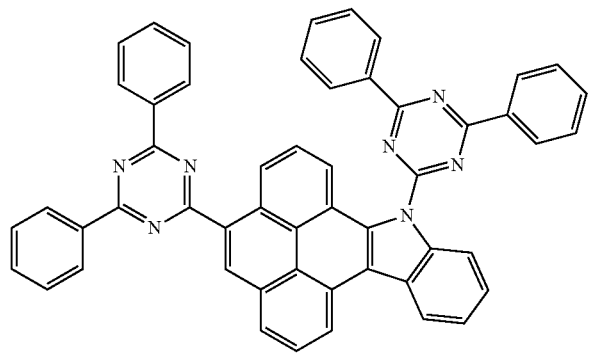
[Chemical Formula 5-10]
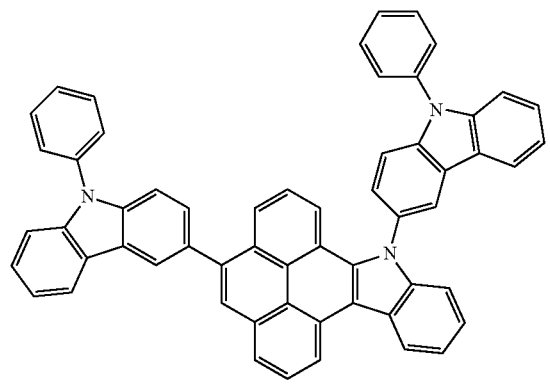
[Chemical Formula 5-11]
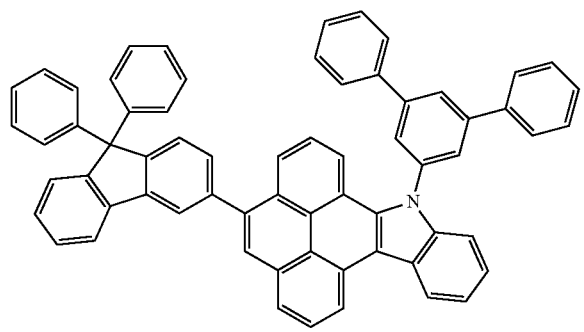
[Chemical Formula 5-12]
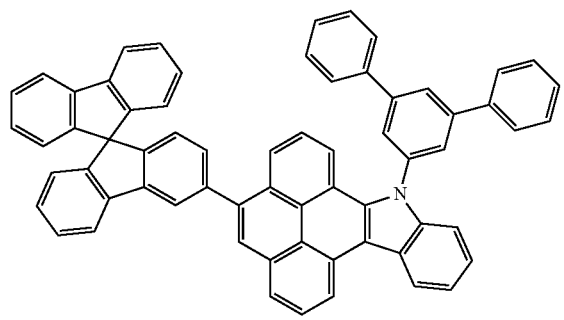
[Chemical Formula 5-13]
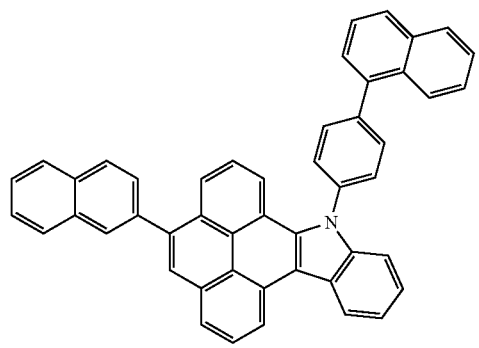

[Chemical Formula 5-14]
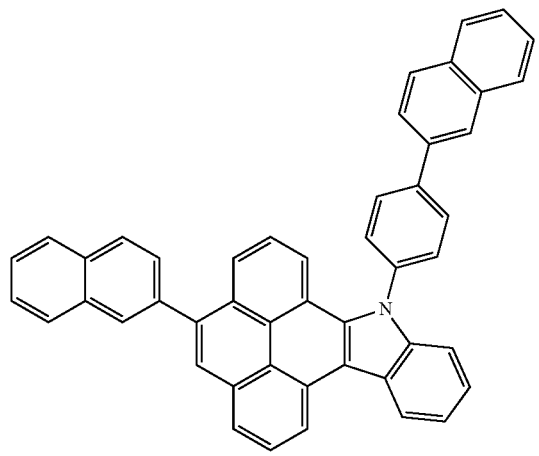
[Chemical Formula 5-15]
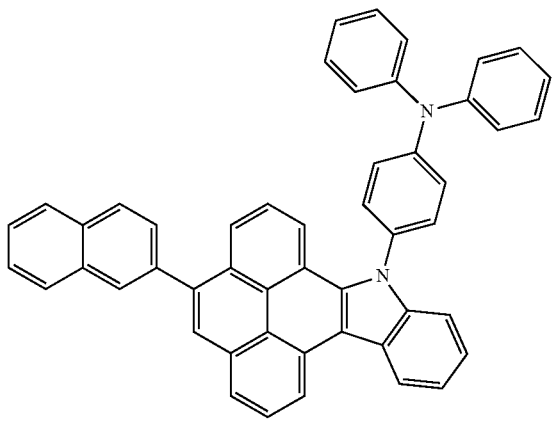
[Chemical Formula 5-16]
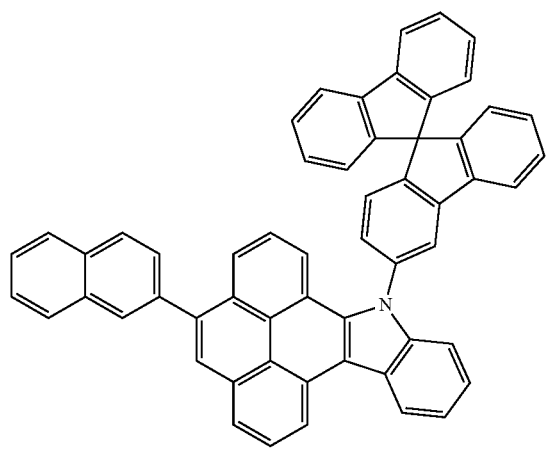
[Chemical Formula 5-17]
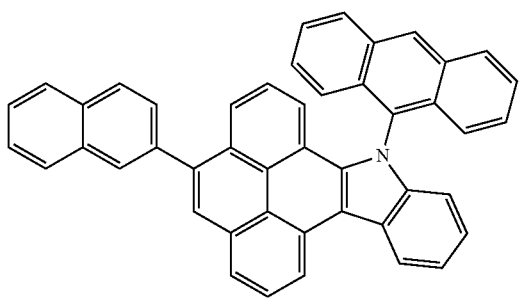
[Chemical Formula 5-18]
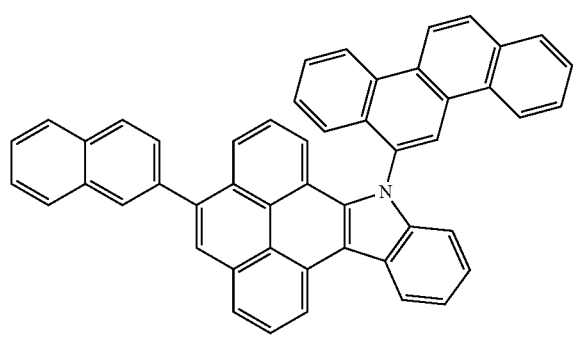
[Chemical Formula 5-19]
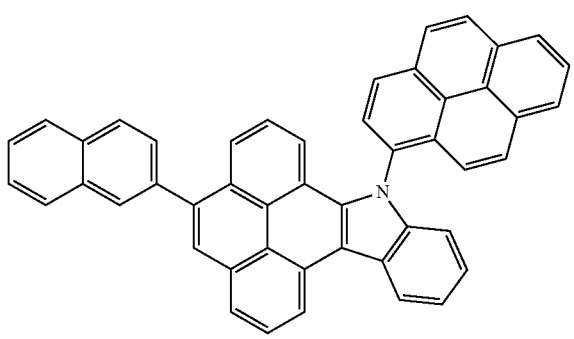
[Chemical Formula 5-20]
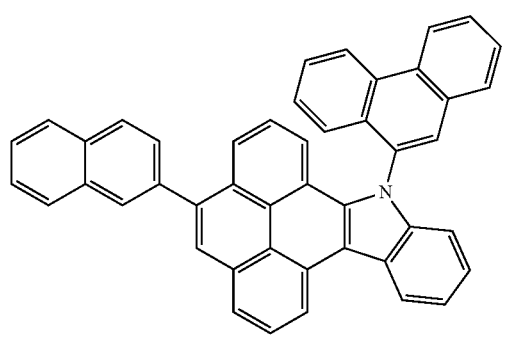
[Chemical Formula 5-21]

-continued
[Chemical Formula 5-22]
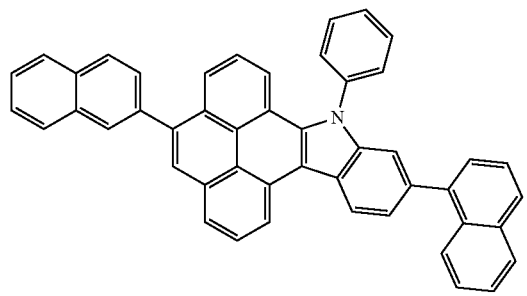
[Chemical Formula 5-23]
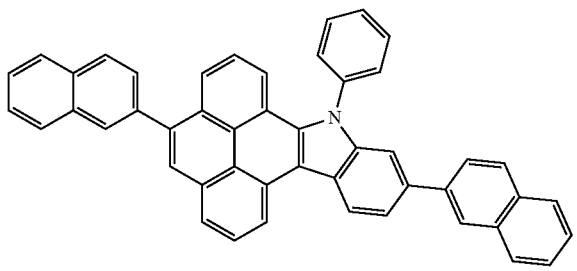
[Chemical Formula 5-24]
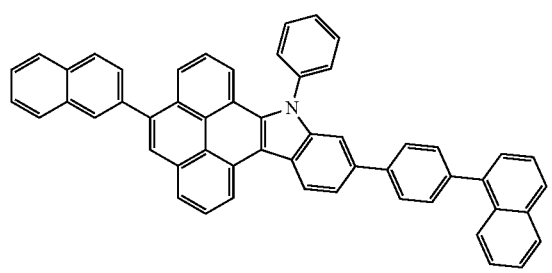
[Chemical Formula 5-25]
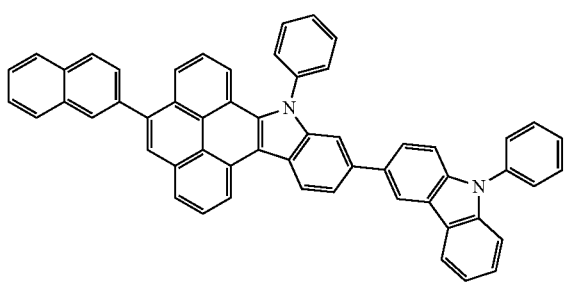
[Chemical Formula 5-26]
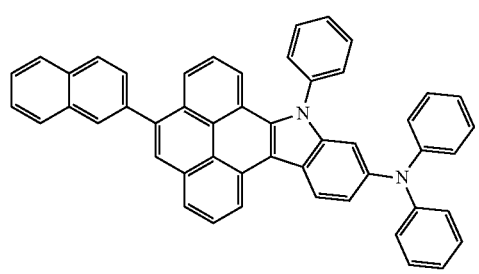
[Chemical Formula 5-27]
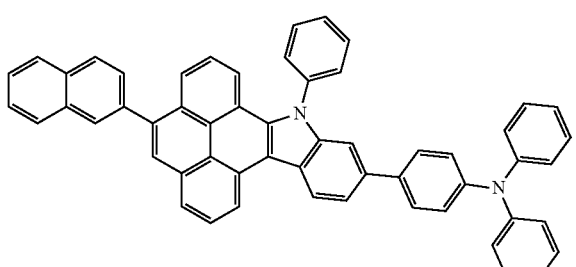
[Chemical Formula 5-28]
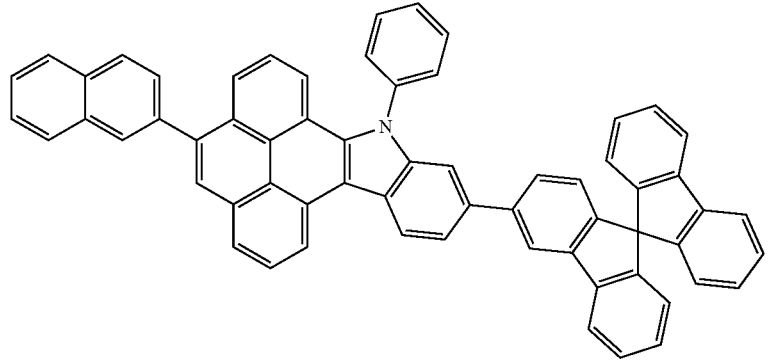
[Chemical Formula 5-29]
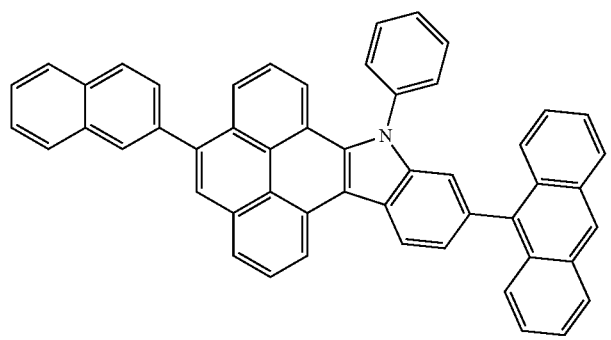

[Chemical Formula 5-30]
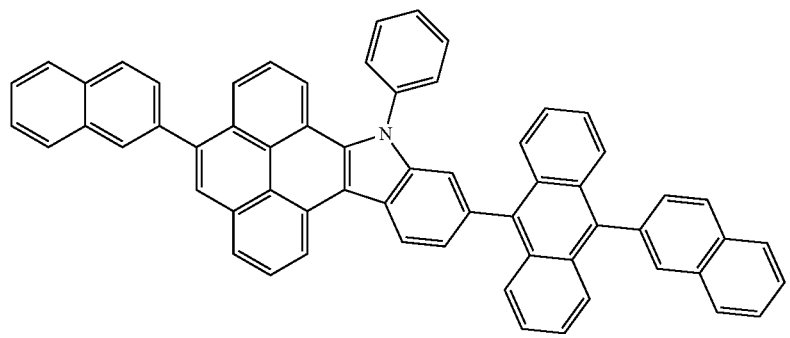
[Chemical Formula 5-31]
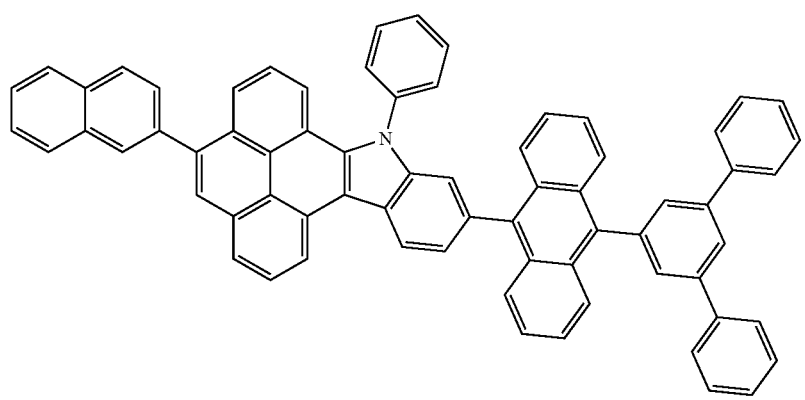
[Chemical Formula 5-32]
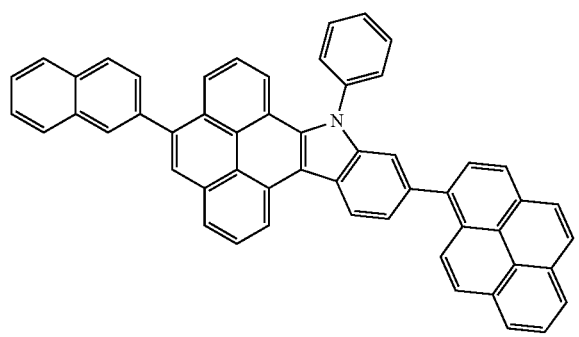
[Chemical Formula 5-33]
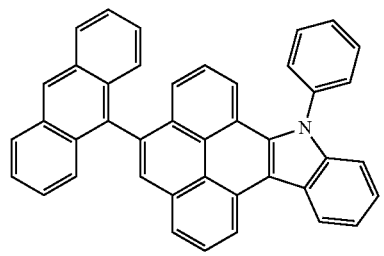
[Chemical Formula 5-34]
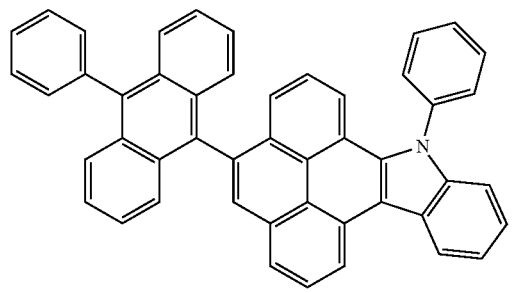
[Chemical Formula 5-35]
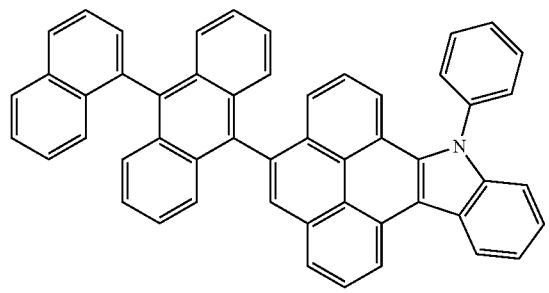

[Chemical Formula 5-36]
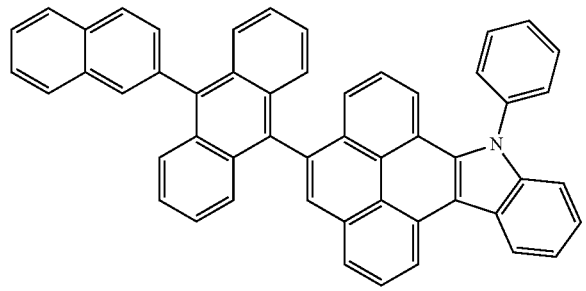
[Chemical Formula 5-37]
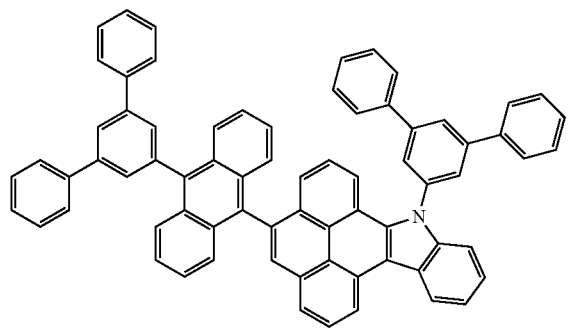
[Chemical Formula 5-38]
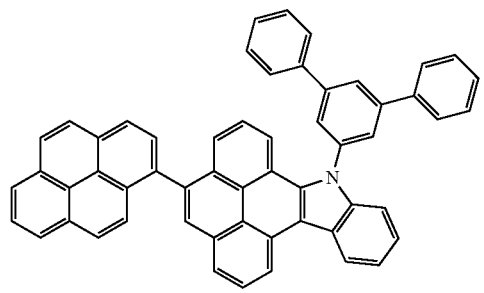
[Chemical Formula 5-39]
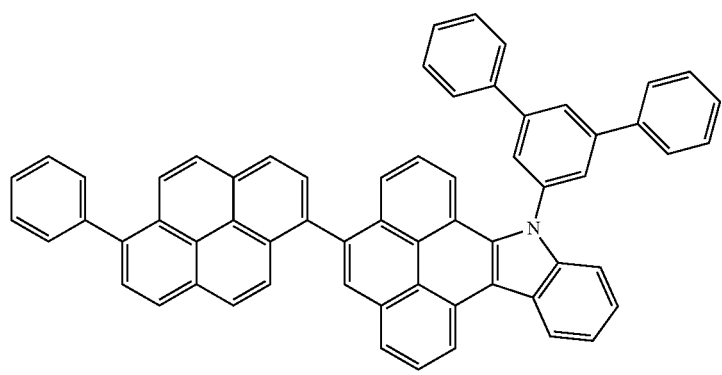
[Chemical Formula 5-40]
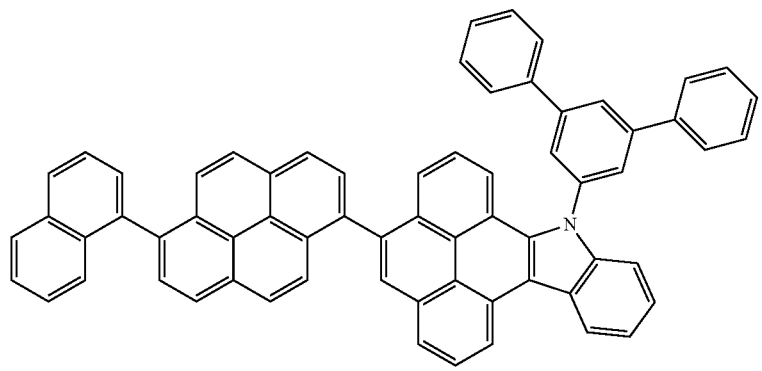

[Chemical Formula 5-41]
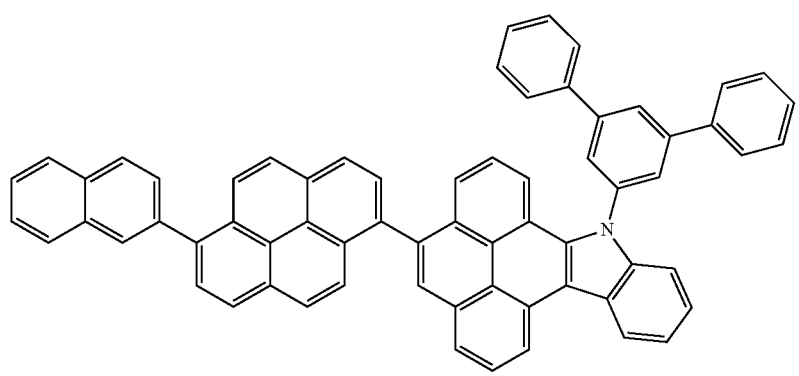
[Chemical Formula 5-42]
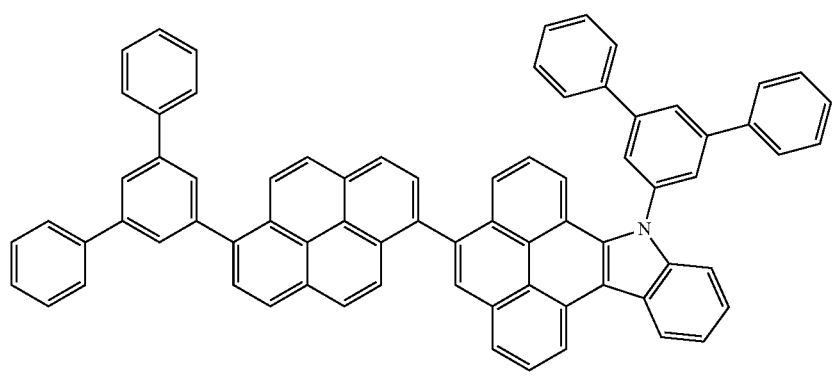
[Chemical Formula 5-43]
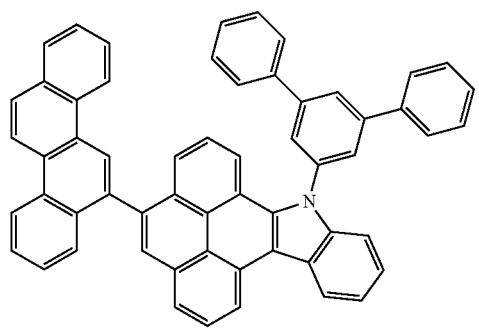
[Chemical Formula 5-44]
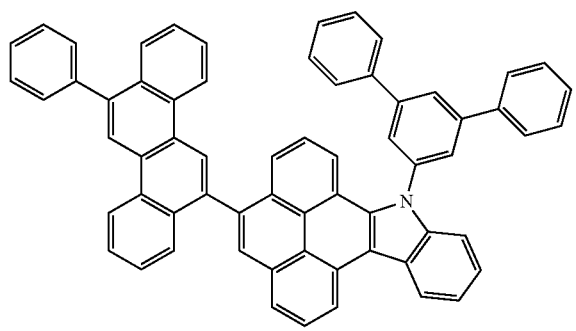
[Chemical Formula 5-45]
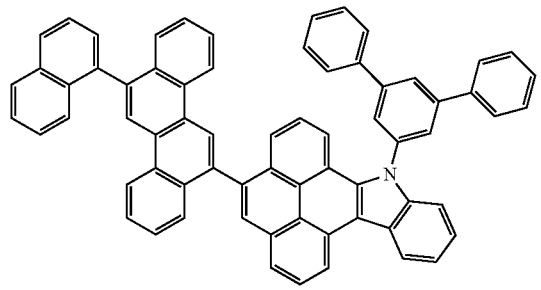
[Chemical Formula 5-46]
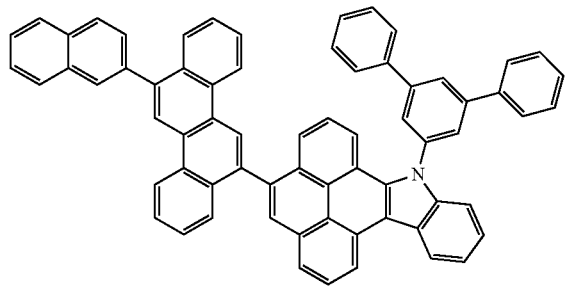

[Chemical Formula 5-47]
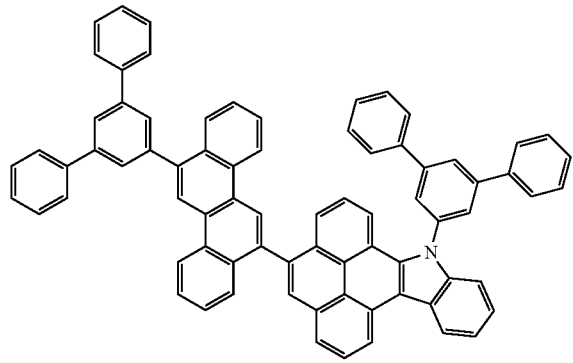
[Chemical Formula 5-48]
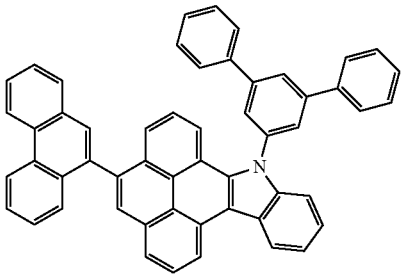
[Chemical Formula 5-49]
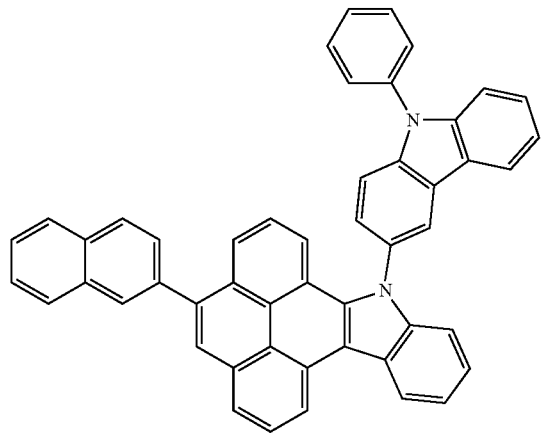
[Chemical Formula 6-1]
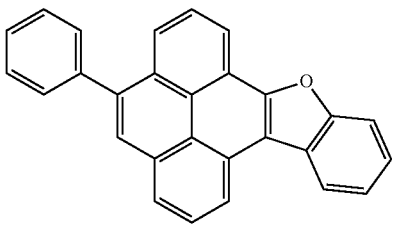
[Chemical Formula 6-2]
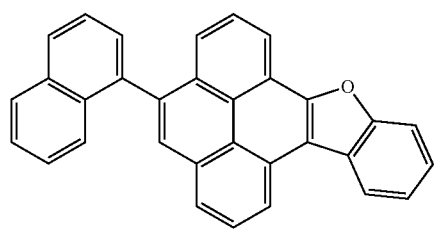
[Chemical Formula 6-3]
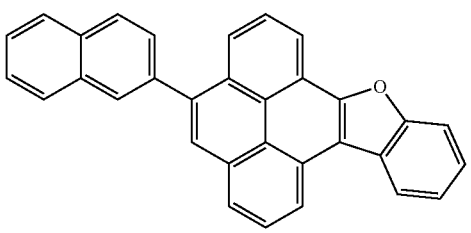
[Chemical Formula 6-4]
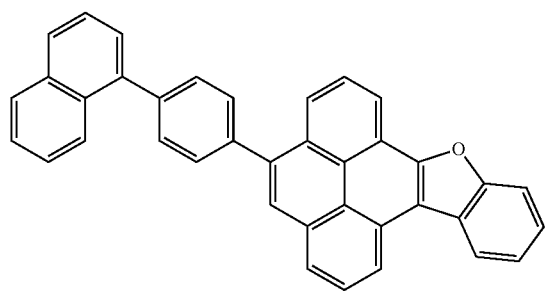
[Chemical Formula 6-5]
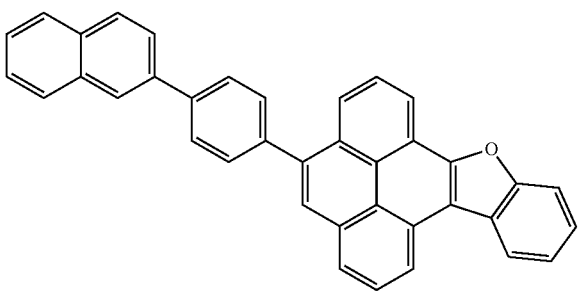

-continued
[Chemical Formula 6-6]
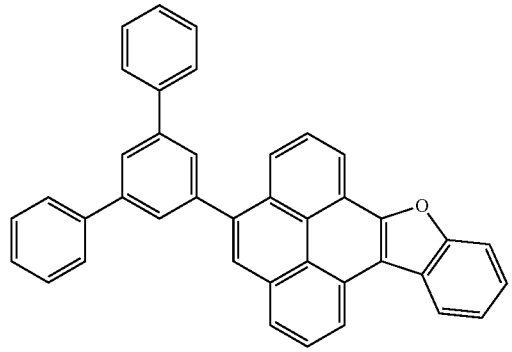
[Chemical Formula 6-7]
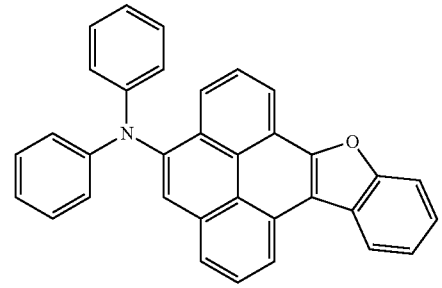
[Chemical Formula 6-8]
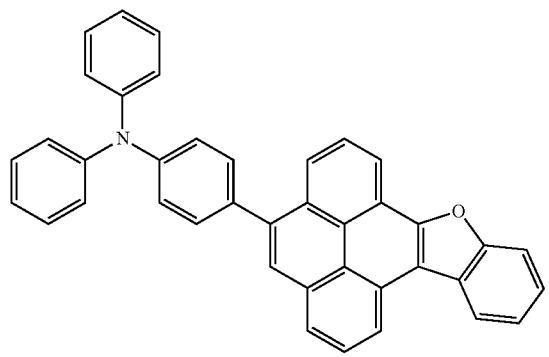
[Chemical Formula 6-9]
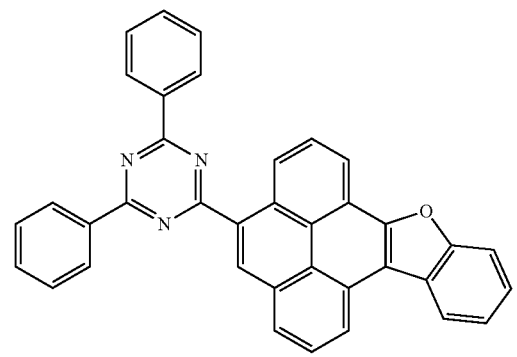
[Chemical Formula 6-10]
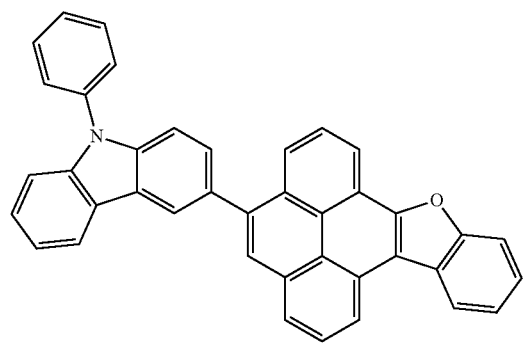
[Chemical Formula 6-11]
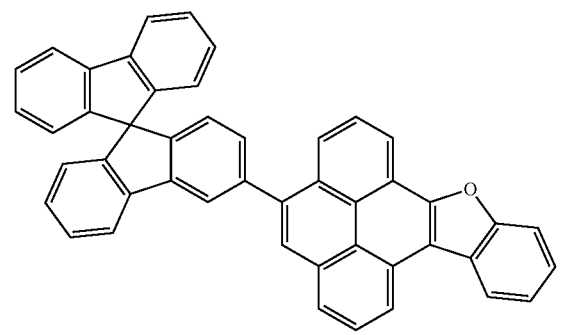
[Chemical Formula 6-12]
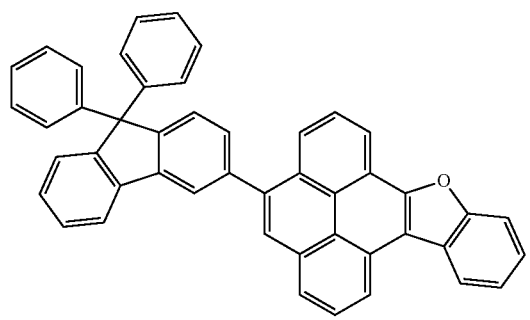
[Chemical Formula 6-13]
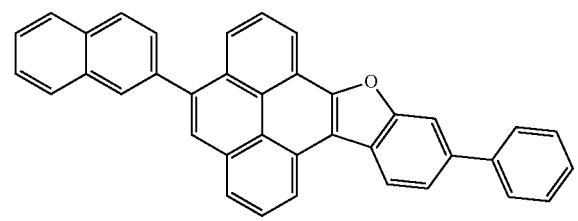

[Chemical Formula 6-14]
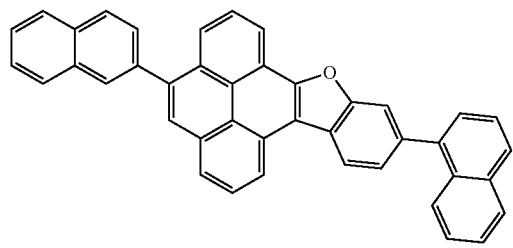
[Chemical Formula 6-15]
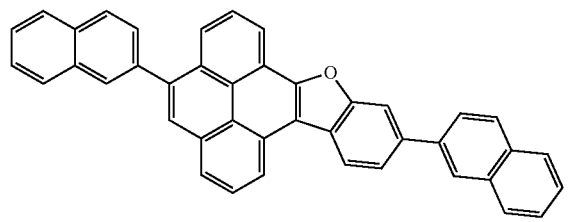
[Chemical Formula 6-16]
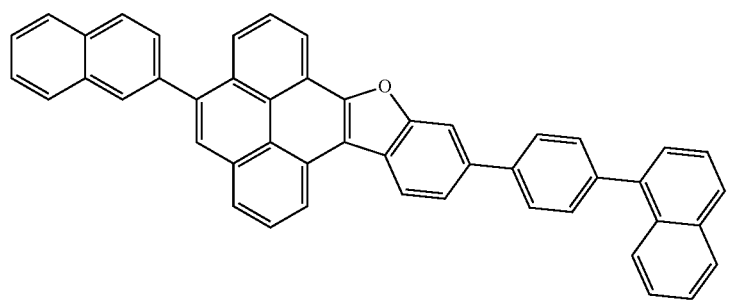
[Chemical Formula 6-17]
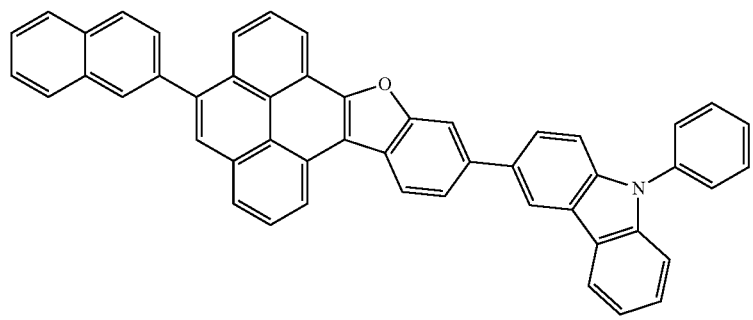
[Chemical Formula 6-18]
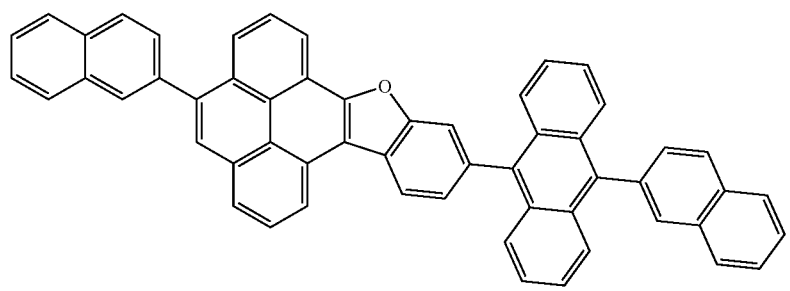
[Chemical Formula 6-19]
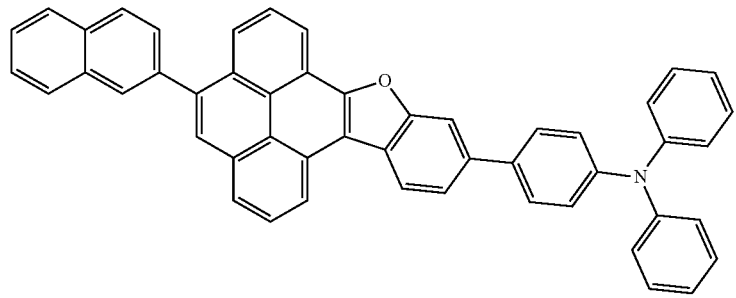

[Chemical Formula 6-20]
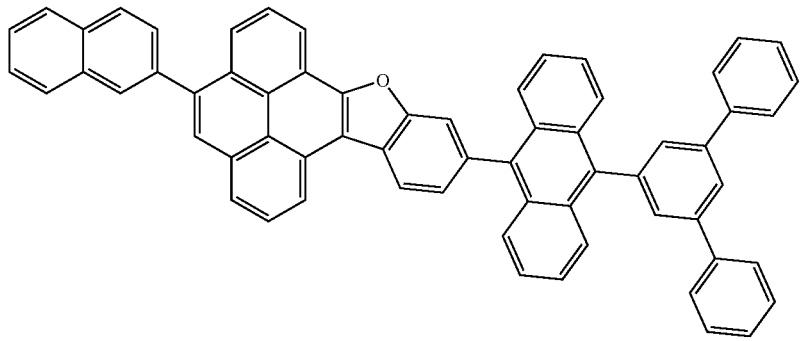
[Chemical Formula 6-21]
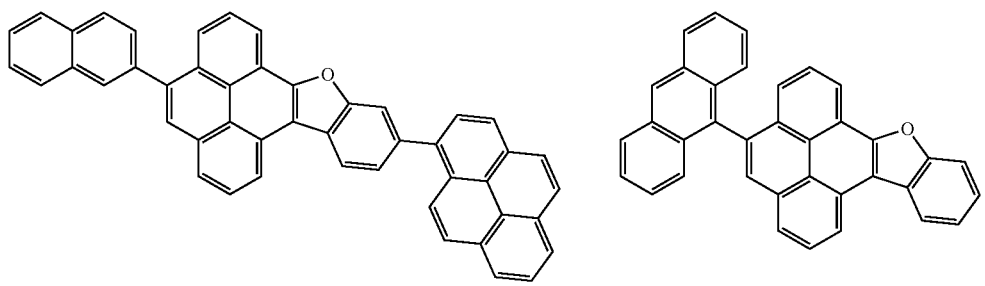
[Chemical Formula 6-22]
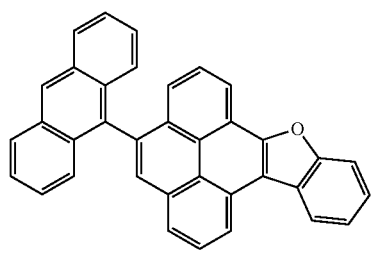
[Chemical Formula 6-23]
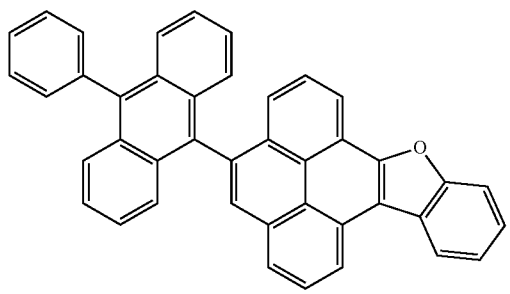
[Chemical Formula 6-24]
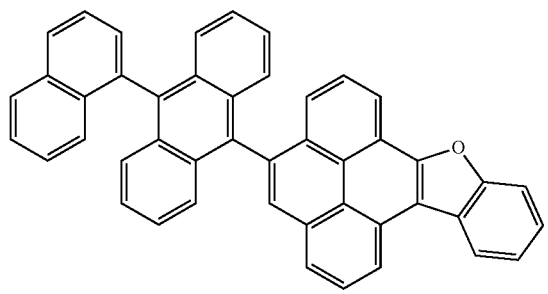
[Chemical Formula 6-25]
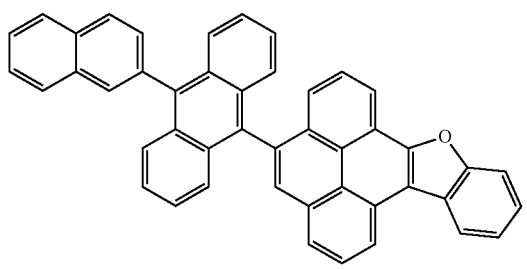
[Chemical Formula 6-26]
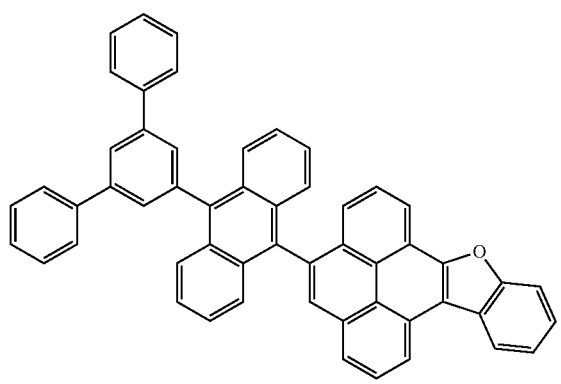
[Chemical Formula 6-27]
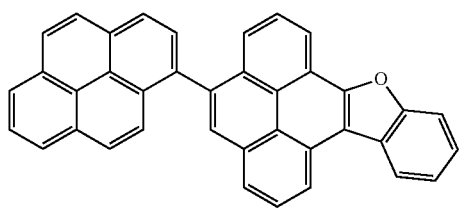
[Chemical Formula 6-28]
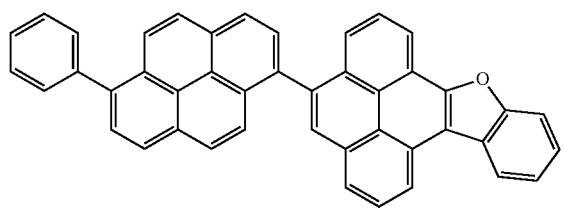

-continued
[Chemical Formula 6-29]
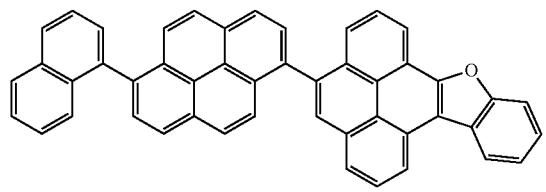
[Chemical Formula 6-30]
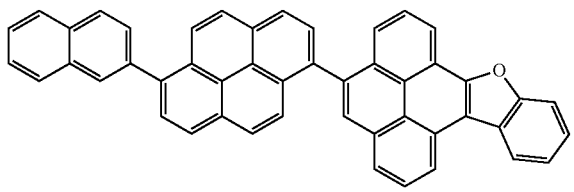
[Chemical Formula 6-31]
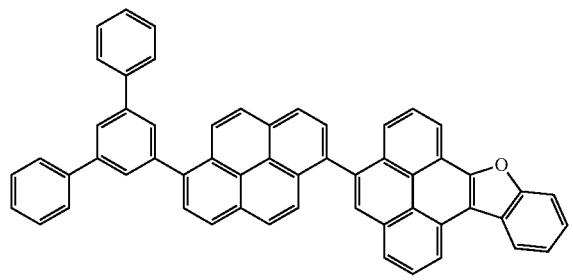
[Chemical Formula 6-32]
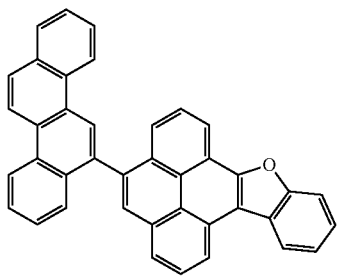
[Chemical Formula 6-33]
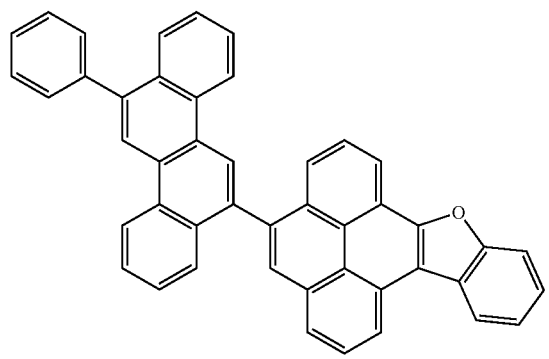
[Chemical Formula 6-34]
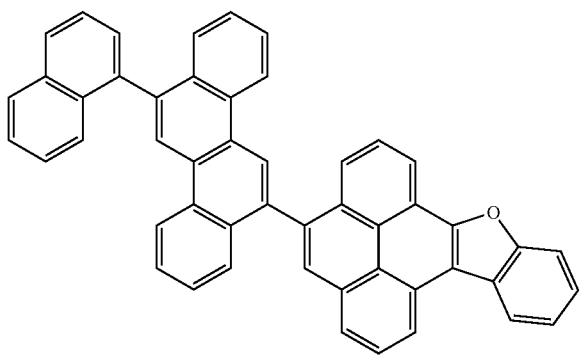
[Chemical Formula 6-35]
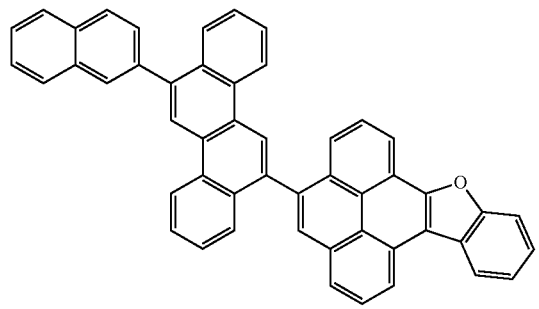
[Chemical Formula 6-36]
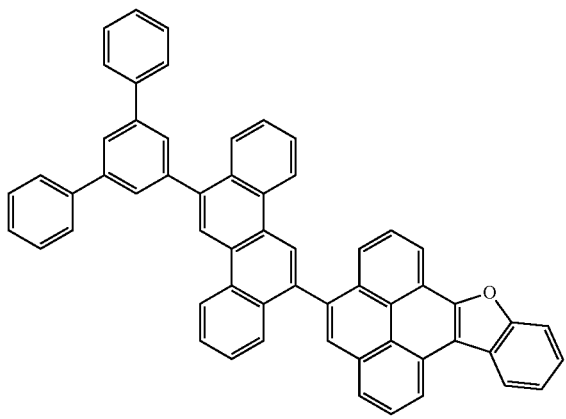
[Chemical Formula 6-37]
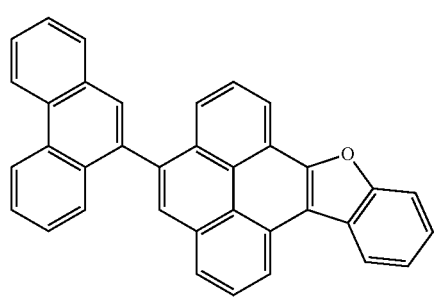
[Chemical Formula 7-1]
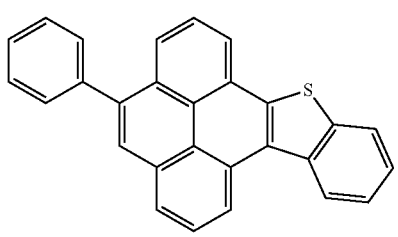

[Chemical Formula 7-2]
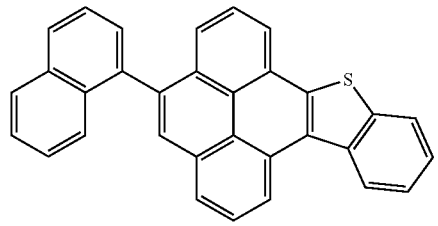
[Chemical Formula 7-3]
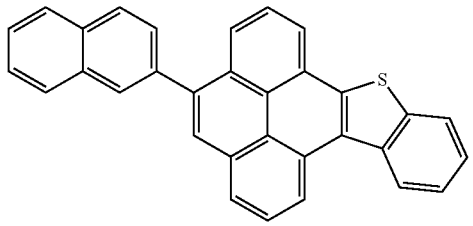
[Chemical Formula 7-4]
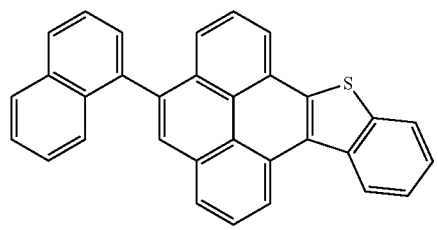
[Chemical Formula 7-5]
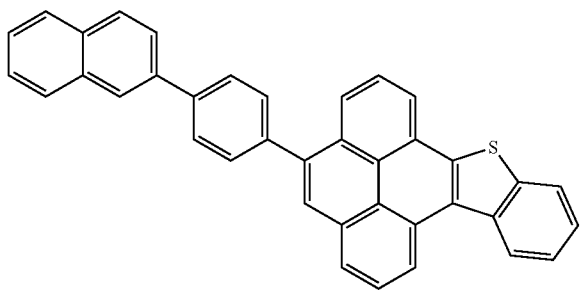
[Chemical Formula 7-6]
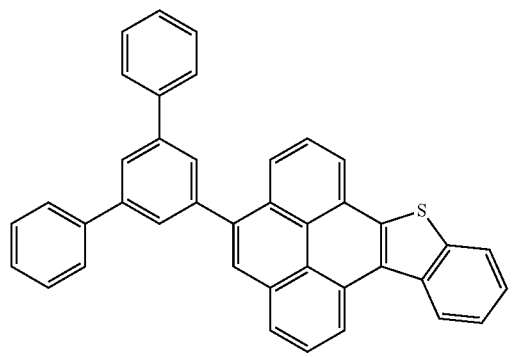
[Chemical Formula 7-7]
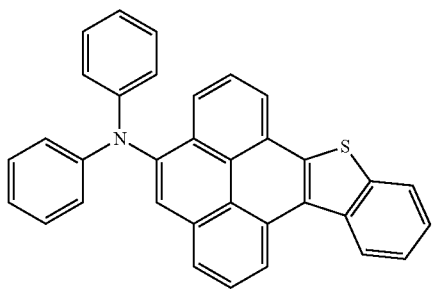
[Chemical Formula 7-8]
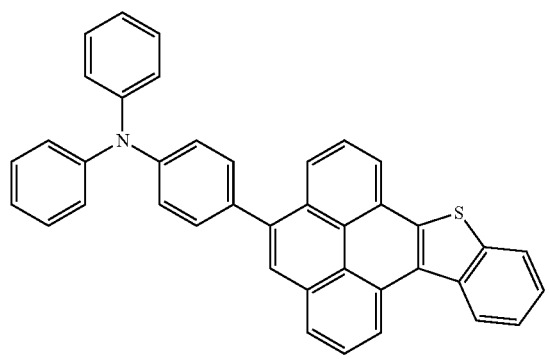
[Chemical Formula 7-9]
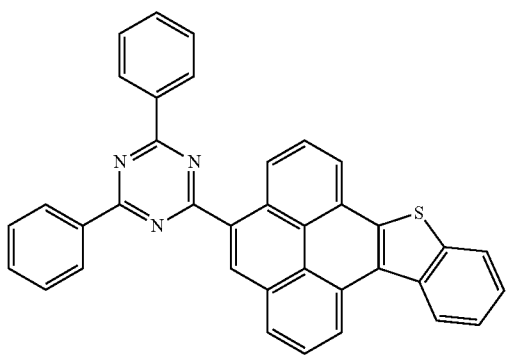

-continued
[Chemical Formula 7-10]
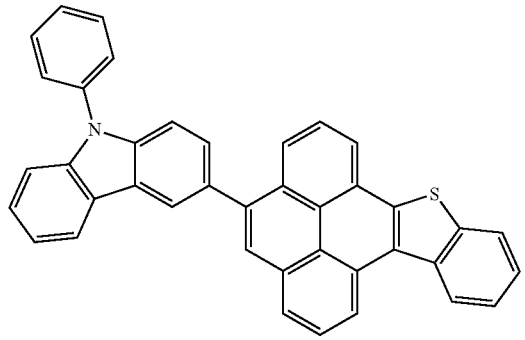
[Chemical Formula 7-11]
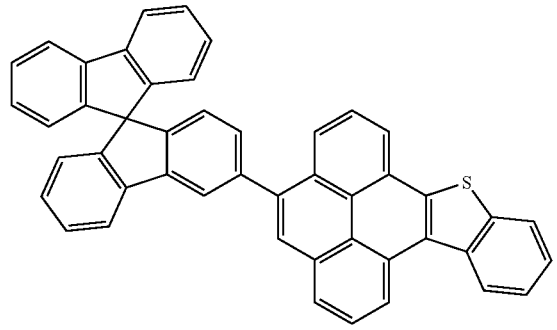
[Chemical Formula 7-12]
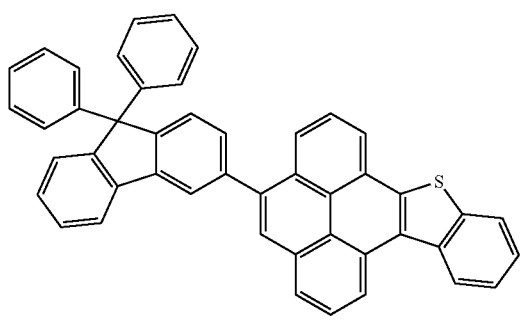
[Chemical Formula 7-13]
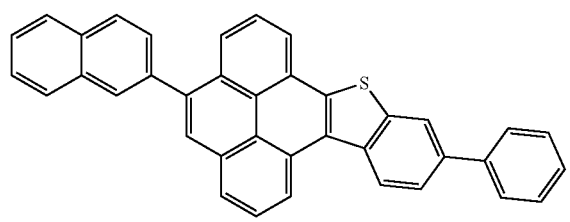
[Chemical Formula 7-14]
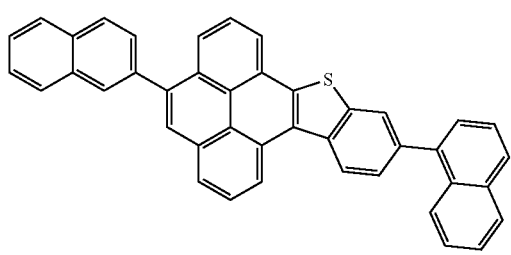
[Chemical Formula 7-15]
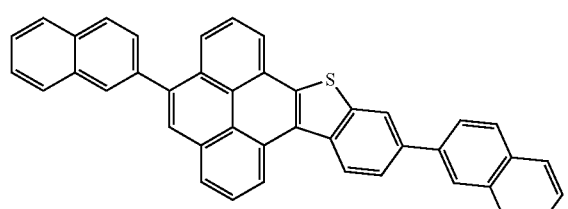
[Chemical Formula 7-16]
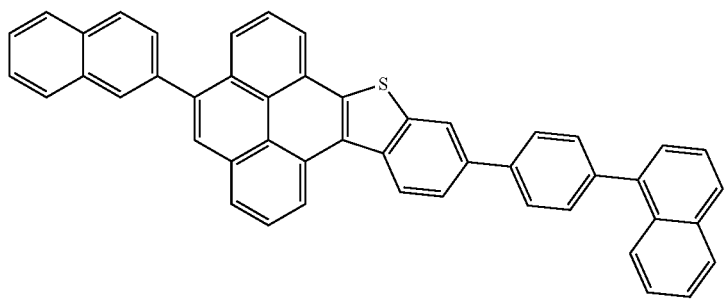
[Chemical Formula 7-17]
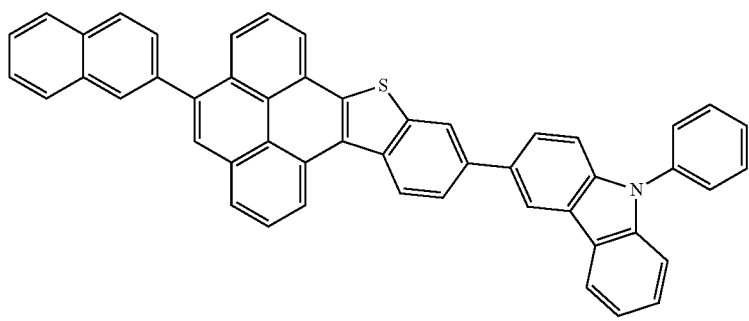

[Chemical Formula 7-18]
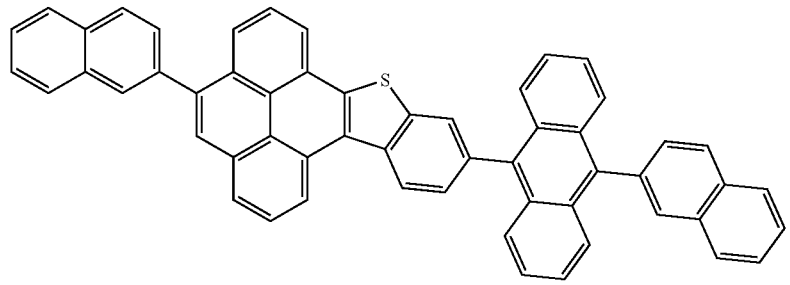
[Chemical Formula 7-19]
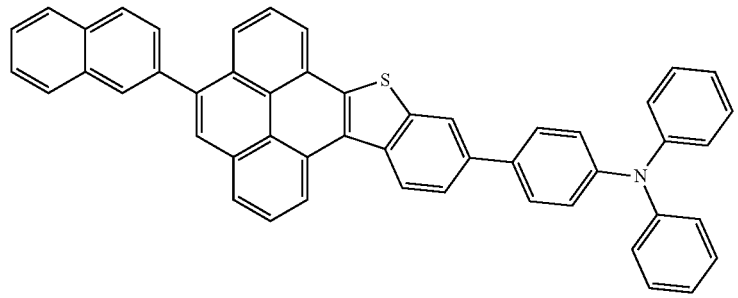
[Chemical Formula 7-20]
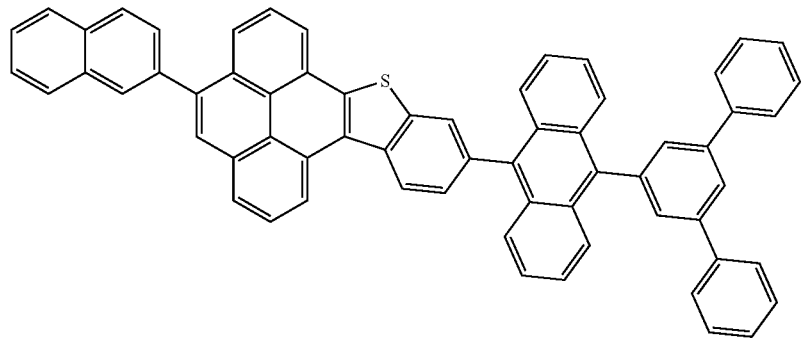
[Chemical Formula 7-21]
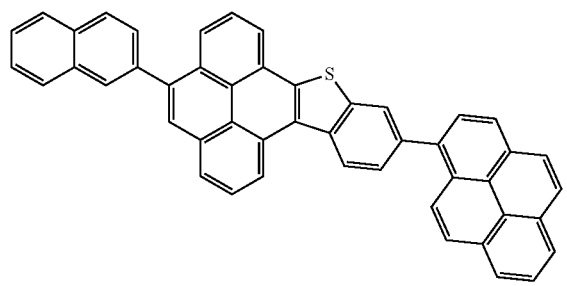
[Chemical Formula 7-22]
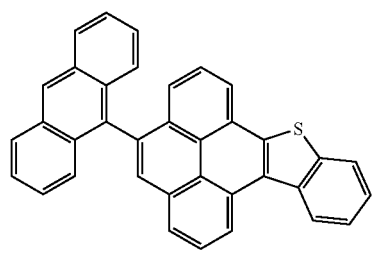
[Chemical Formula 7-23]
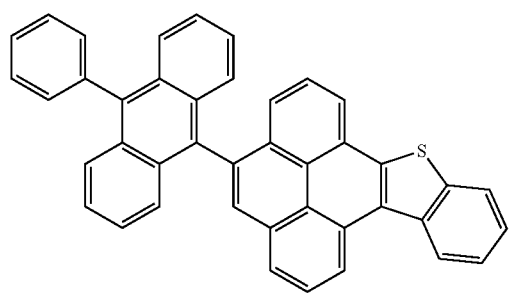
[Chemical Formula 7-24]
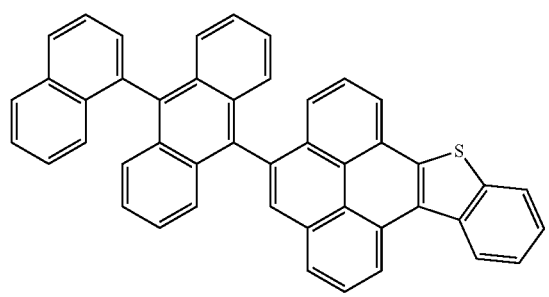

-continued
[Chemical Formula 7-25]
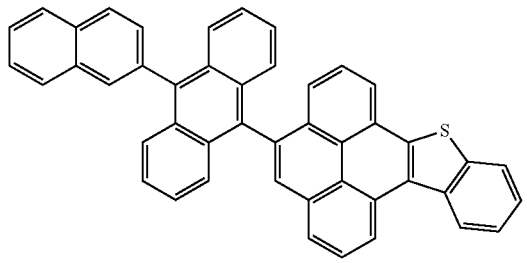
[Chemical Formula 7-26]
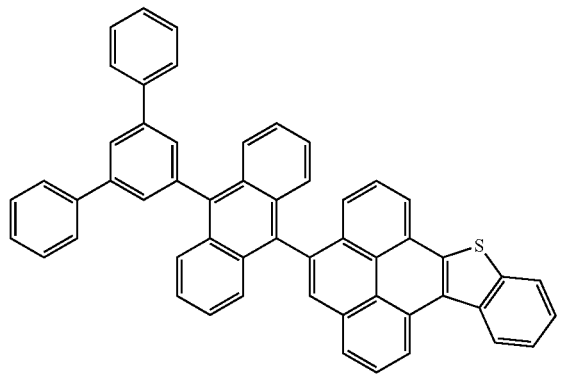
[Chemical Formula 7-27]
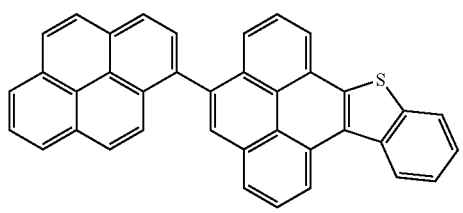
[Chemical Formula 7-28]
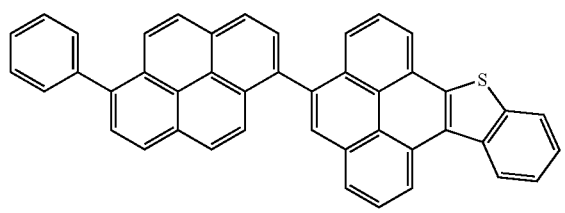
[Chemical Formula 7-29]
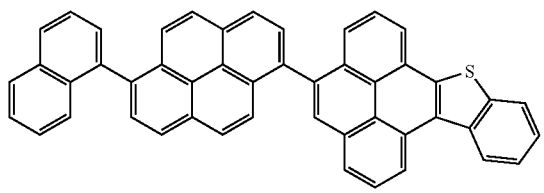
[Chemical Formula 7-30]
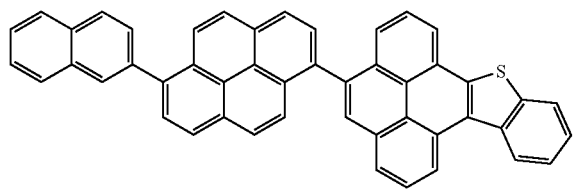
[Chemical Formula 7-31]
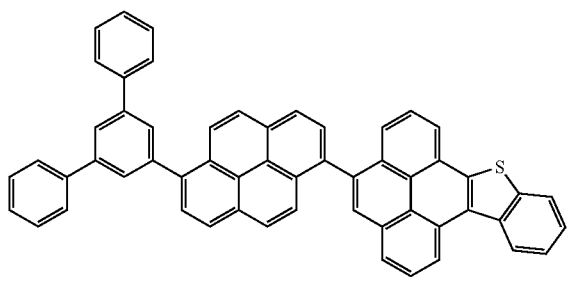
[Chemical Formula 7-32]
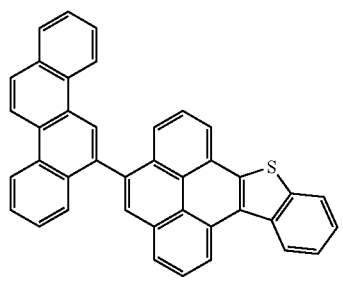
[Chemical Formula 7-33]
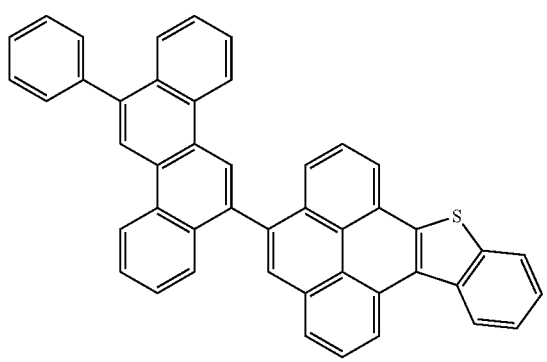
[Chemical Formula 7-34]
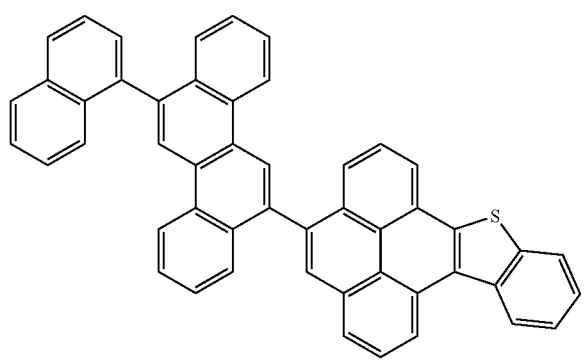

[Chemical Formula 7-35]

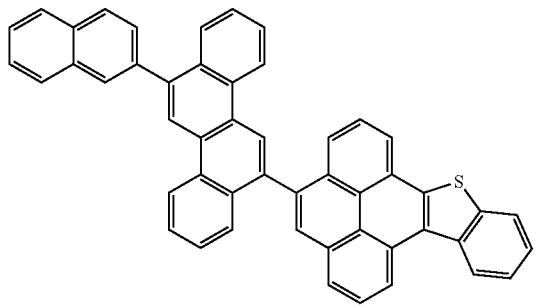

[Chemical Formula 7-36]

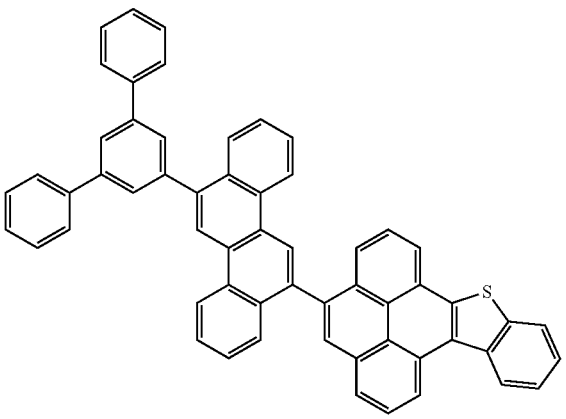

[Chemical Formula 7-37]

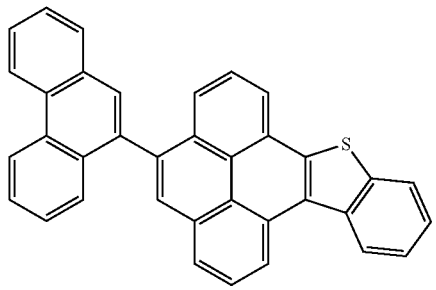

Another embodiment provides an organic optoelectronic device including an anode, a cathode, and at least one organic layer disposed between the anode and the cathode wherein at least one layer of the organic layer includes the organic compound.

The organic layer may be selected from a light emitting layer, a hole transport layer, a hole injection layer, an electron transport layer, an electron injection layer, a hole blocking layer, and a combination thereof.

The organic compound may be included in the light emitting layer.

The organic optoelectronic device may be selected from an organic photoelectric device, an organic light emitting diode, an organic solar cell, an organic transistor, an organic photo conductor drum, and an organic memory device.

The organic optoelectronic device may be an organic light emitting diode.

Yet another embodiment provides a display device including the organic light emitting diode.

Advantageous Effects

Sufficient electric characteristics, light emitting characteristics, color characteristics, and the like may be obtained by providing an organic compound including a novel core and applying it to an organic optoelectronic device such as an organic light emitting diode and the like.

DETAILED DESCRIPTION

Figure 1:
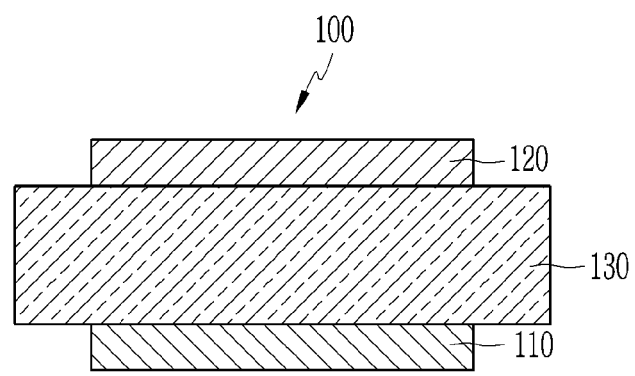
FIG. 1 is a cross-sectional view showing an organic light emitting diode according to an embodiment.

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to 010 alkylsilyl group, a C3 to C30 cycloalkyl group, a C3 to C30 heterocycloalkyl group, a C6 to C30 aryl group, a C3 to C30 heterocyclic, a C1 to C20 alkoxy group, a fluoro group, a C1 to C10 trifluoroalkyl group such as a trifluoromethyl group, and the like, or a cyano group.

Further, adjacent two substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as the trifluoromethyl group, and the like, or cyano group may be fused with each other to form a ring.

For example, in the present specification, the substituted fluorene group may include a fused ring formed by combining the aryl groups as well as a fluorene group substituted with an aryl group. For example, a compound represented by Chemical Formula A corresponds to a substituted fluorene compound.

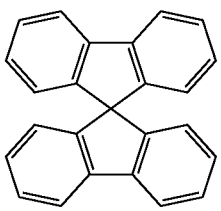

[Chemical Formula A]

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

"Alkenylene group" refers to a functional group consisting of at least one carbon-carbon double bond of at least two carbon atoms and "alkynylene group" refers to a functional group consisting of at least one carbon-carbon triple bond of at least two carbon atoms. Regardless of being saturated or unsaturated, the alkyl group may be branched, linear or cyclic.

An alkyl group may be a C1 to C20 alkyl group. More specifically, the alkyl group may be a C1 to C10 alkyl group or a C1 to C6 alkyl group.

For example, a C1 to C4 alkyl group may include may have 1 to 4 carbon atoms in an alkyl chain and the alkyl chain may be selected from the group consisting of methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are an aryl group and a heteroaryl group.

"Aryl group" may be monocyclic, polycyclic or fused ring polycyclic (i.e., rings sharing adjacent pairs of carbon atoms) functional group.

"Heteroaryl group" refers to an aryl group including 1 to 3 hetero atoms selected from the group consisting of N, O, S and P and remaining carbons. The heteroaryl group may be a fused ring where each ring may include 1 to 3 heteroatoms.

Hereinafter, an organic compound according to an embodiment is described.

An organic compound according to an embodiment is represented by a combination of Chemical Formulas 1 and 2.

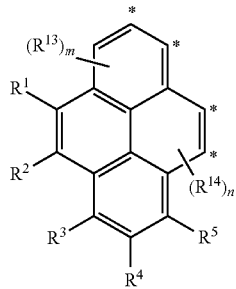

[Chemical Formula 1]

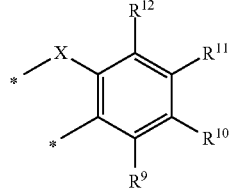

[Chemical Formula 2]

In Chemical Formulas 1 and 2, $R^1$ to $R^5$ and $R^9$ to $R^{14}$ are independently hydrogen, deuterium, a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, X is —$CR^aR^b$—, —$NR^c$—, —O—, —S—, —Si—, or —$PR^d$—, wherein $R^a$ to $R^d$ are independently hydrogen, deuterium, a substituted or unsubstituted amine group, a substituted or unsubstituted C1 to C30 alkyl group, a substituted or unsubstituted C6 to C30 aryl group or a substituted or unsubstituted C2 to C30 heteroaryl group or $R^a$ and $R^b$ are linked with each other to form a fused ring, m is an integer of 1 or 3, n is an integer of 0 or 2, and two *'s of Chemical Formula 2 are bound to adjacent two of four *'s of Chemical Formula 1 to form a fused ring.

The organic compound includes a novel fused ring formed by bonding a pyrene compound of Chemical Formula 1 with a cyclic compound Chemical Formula 2 as a core. Since the organic compound represented by a combination of Chemical Formulas 1 and 2 includes the novel fused ring as a core, an organic light emitting diode and the like including the organic compound may show excellent light emitting characteristics, long life-span characteristics, and satisfactory electron characteristics. In other words, the organic compound according to an embodiment includes a pyrene moiety of Chemical Formula 1 and thus may show long life-span characteristics, and as the cyclic compound of Chemical Formula 2 is bonded with the pyrene compound of Chemical Formula 1 and forms a fused ring, the organic compound includes a moiety such as a fluorene-based moiety, a carbazole-based moiety, and the like and thus may increase a charge balance in a device and cause excellent luminous efficiency, thermal stability, and long life-span characteristics.

The organic compound represented by a combination of Chemical Formulas 1 and 2 may be represented by Chemical Formula 3.

[Chemical Formula 3]

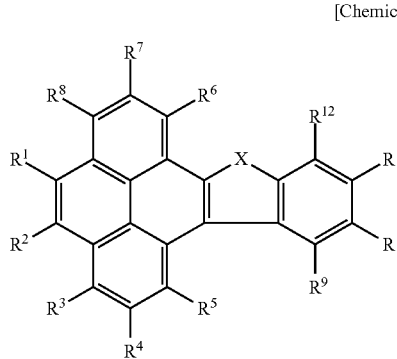

In Chemical Formula 3, $R^1$ to $R^{12}$ are independently hydrogen, deuterium, a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, provided that R6 to R8 are the same, and X is —$CR^aR^b$—, —$NR^c$—, —O—, —S—, —Si—, or —$PR^d$—, wherein $R^a$ to $R^d$ are independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heteroaryl group or $R^a$ and $R^b$ are linked with each other to form a fused ring.

When X is —$CR^aR^b$—, —$NR^c$—, —O—, —S—, —Si—, or —$PR^d$—, charge and electron transport properties are improved.

For example, in Chemical Formula 3, at least one of $R^1$ and $R^2$ may be substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, at least one of $R^9$ to $R^{12}$ may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, and X may be —$CR^aR^b$—, —$NR^c$—, —O—, or —S—, wherein $R^a$ to $R^c$ may independently be hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heteroaryl group, or $R^a$ and $R^b$ may be linked with each other to form a fused ring.

For example, one of $R^1$ and $R^2$ may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof and the other may be hydrogen, and one of $R^9$ to $R^{12}$ may be a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof and the other three may be hydrogen.

More specifically, the organic compound may be represented by one of Chemical Formulas 4-1 to 4-38, 5-1 to 5-49, 6-1 to 6-37, and 7-1 to 7-37.

[Chemical Formula 4-1]

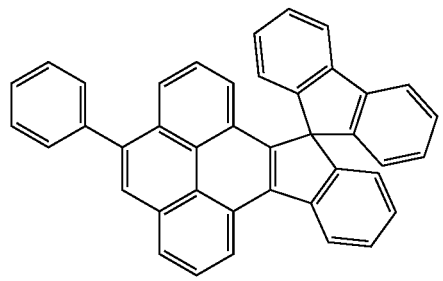

[Chemical Formula 4-2]

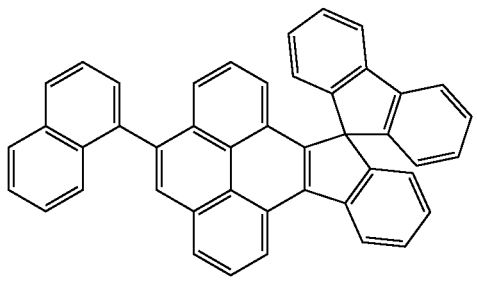

-continued
[Chemical Formula 4-3]
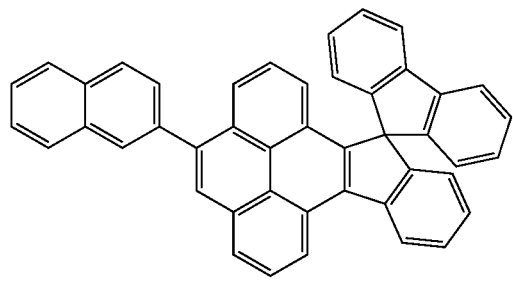
[Chemical Formula 4-4]
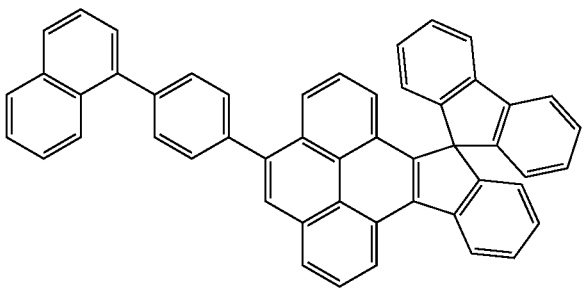
[Chemical Formula 4-5]
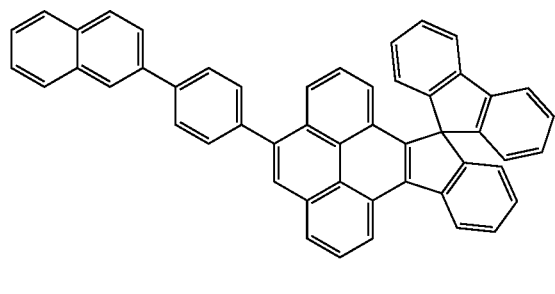
[Chemical Formula 4-6]
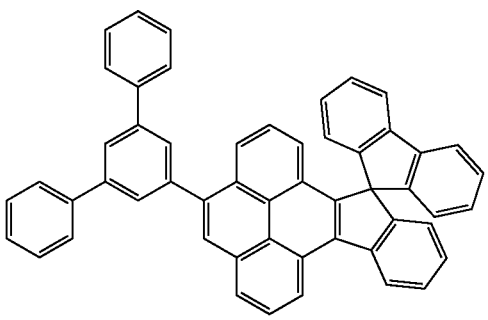
[Chemical Formula 4-7]
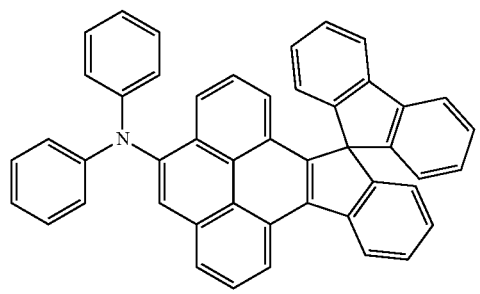
[Chemical Formula 4-8]
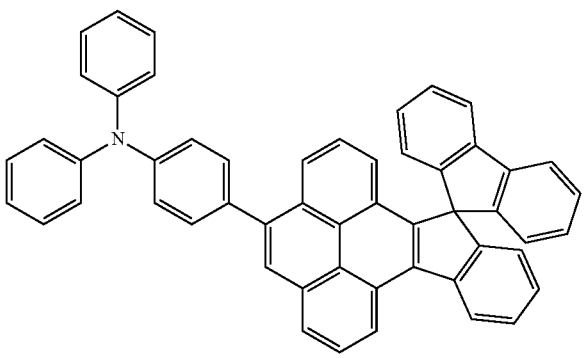
[Chemical Formula 4-9]
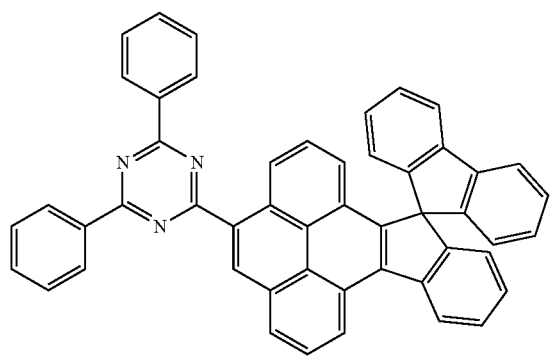
[Chemical Formula 4-10]
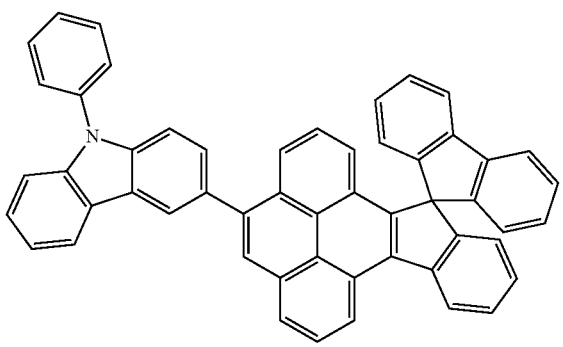

-continued
[Chemical Formula 4-11]
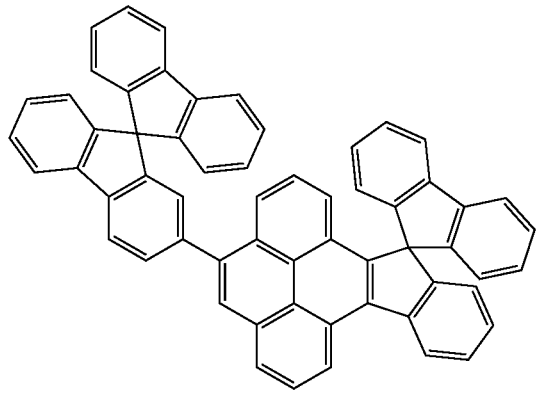
[Chemical Formula 4-12]
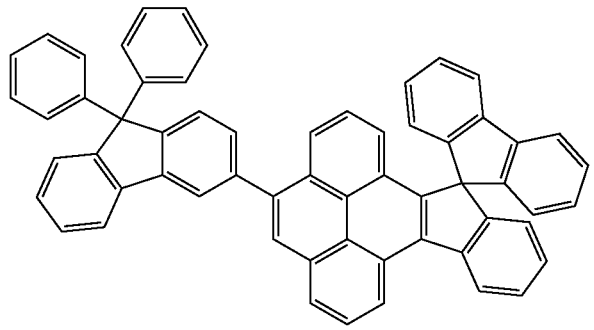
[Chemical Formula 4-13]
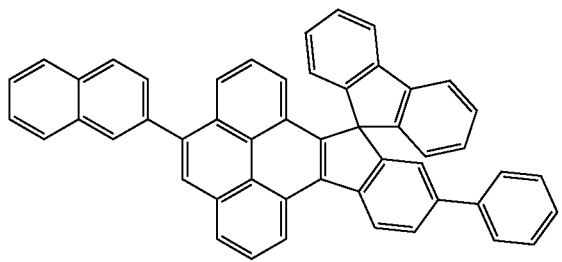
[Chemical Formula 4-14]
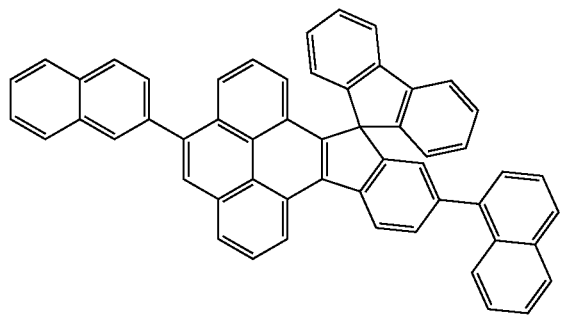
[Chemical Formula 4-15]
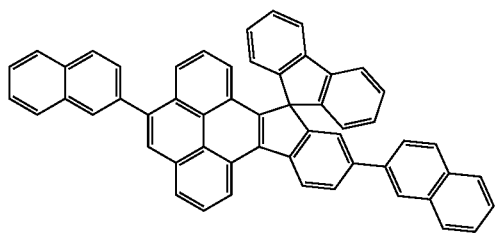
[Chemical Formula 4-16]
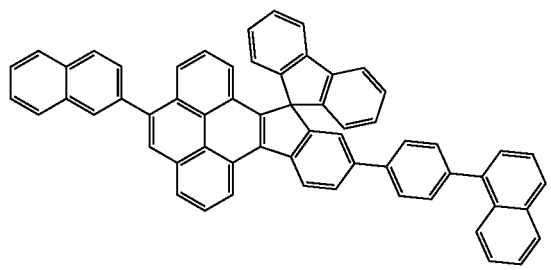
[Chemical Formula 4-17]
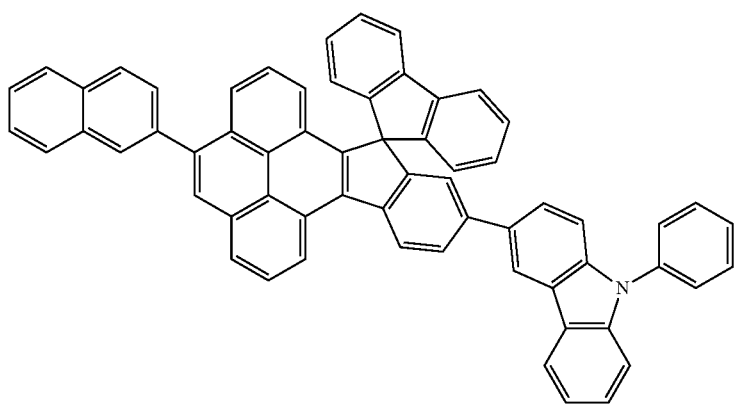

[Chemical Formula 4-18]
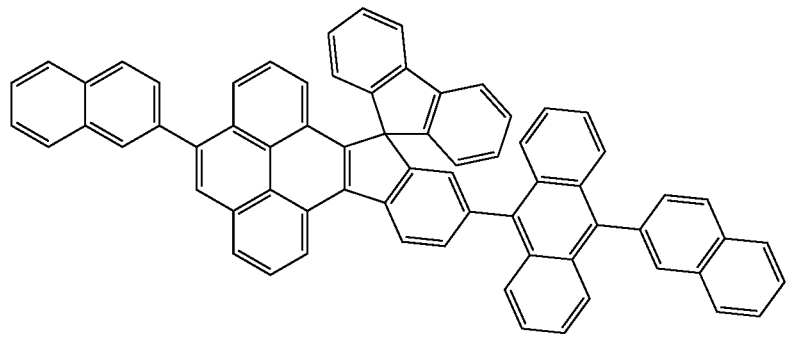
[Chemical Formula 4-19]
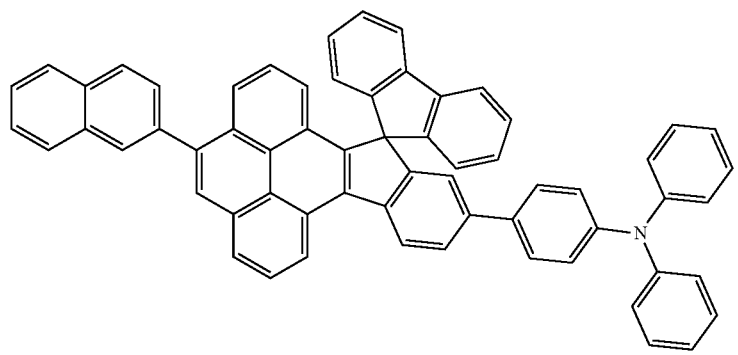
[Chemical Formula 4-20]
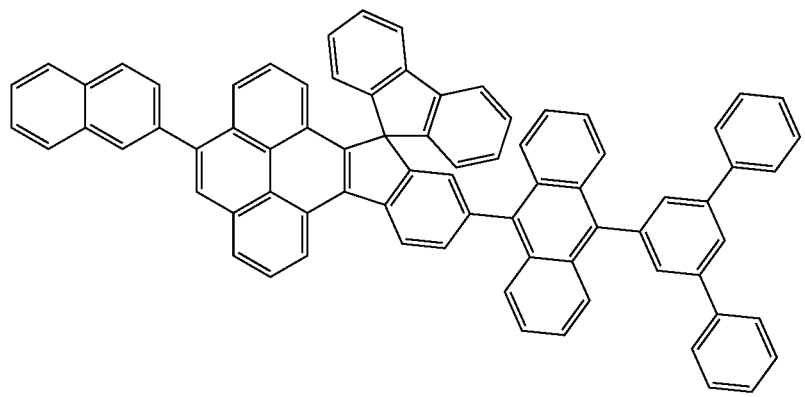
[Chemical Formula 4-21]
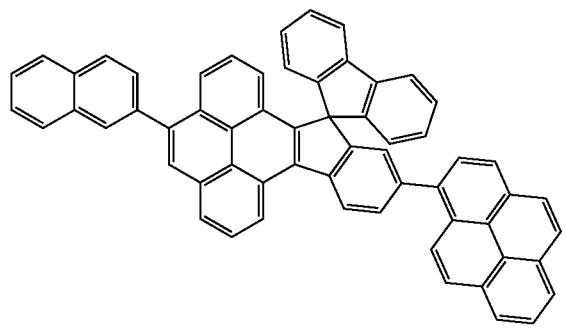
[Chemical Formula 4-22]
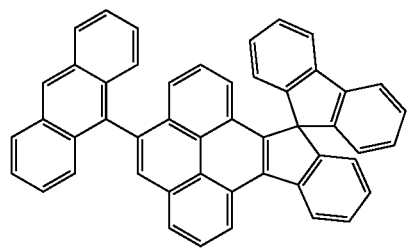

[Chemical Formula 4-23]
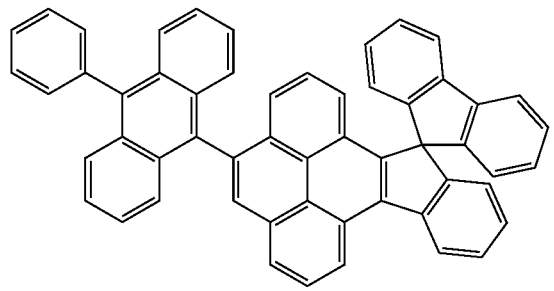
[Chemical Formula 4-24]
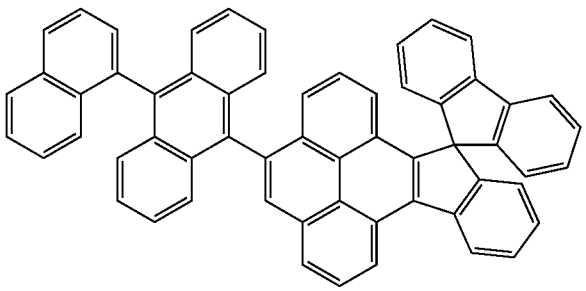
[Chemical Formula 4-25]
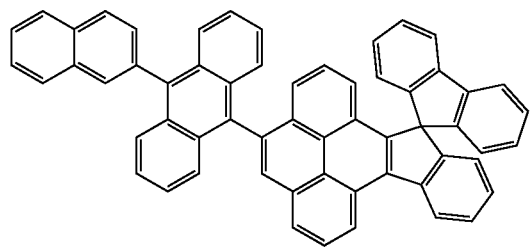
[Chemical Formula 4-26]
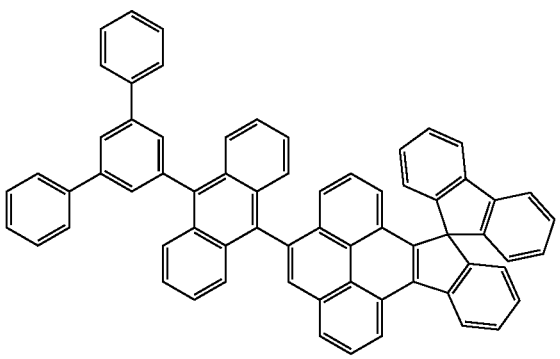
[Chemical Formula 4-27]
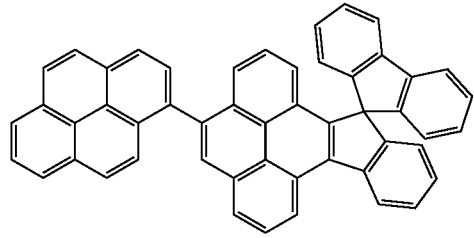
[Chemical Formula 4-28]
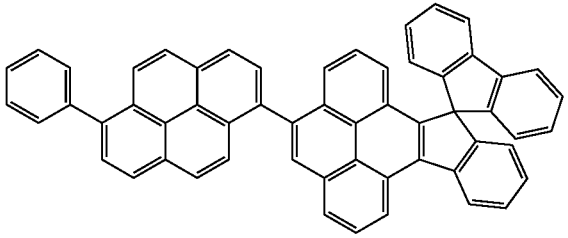
[Chemical Formula 4-29]
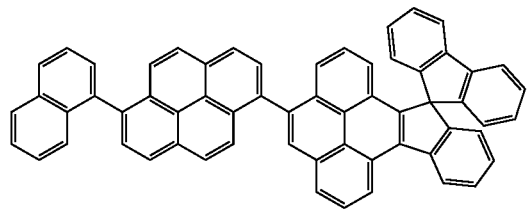
[Chemical Formula 4-30]
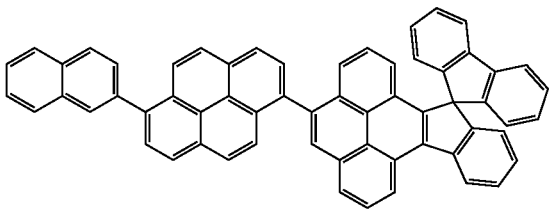
[Chemical Formula 4-31]
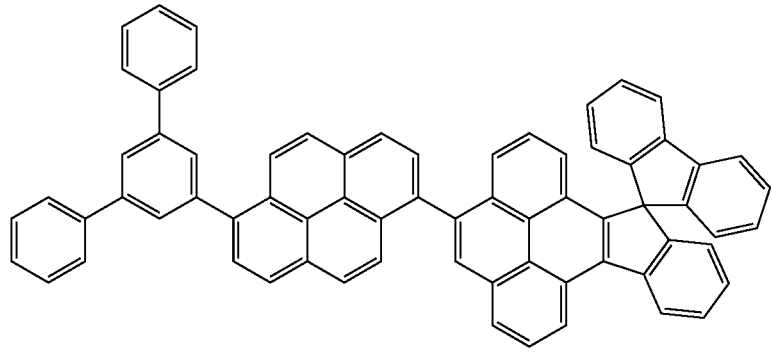

-continued
[Chemical Formula 4-32]
[Chemical Formula 4-33]
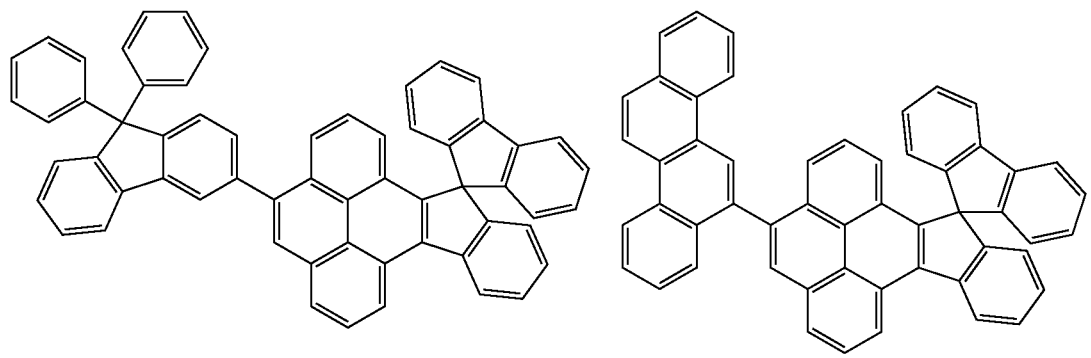
[Chemical Formula 4-34]
[Chemical Formula 4-35]
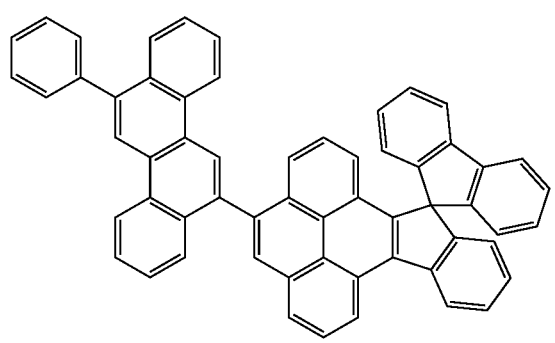
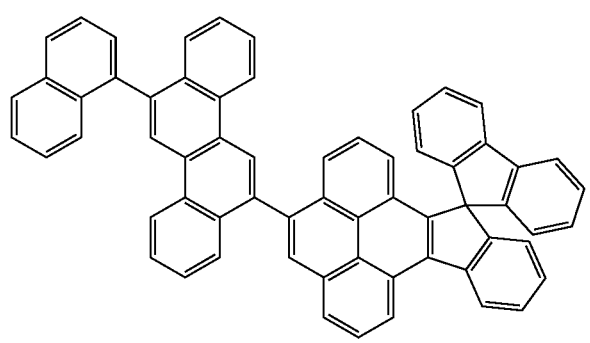
[Chemical Formula 4-36]
[Chemical Formula 4-37]
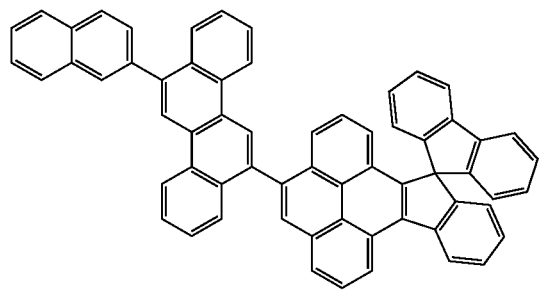
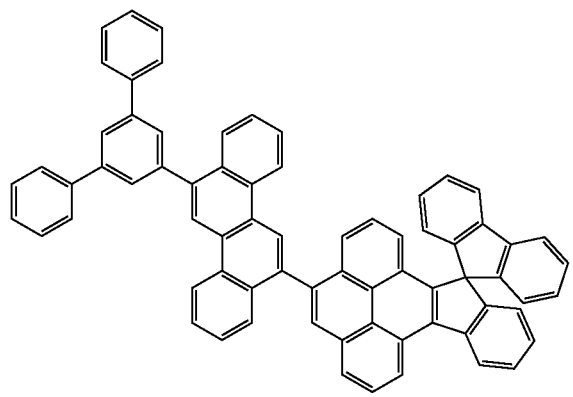
[Chemical Formula 4-38]
[Chemical Formula 5-1]
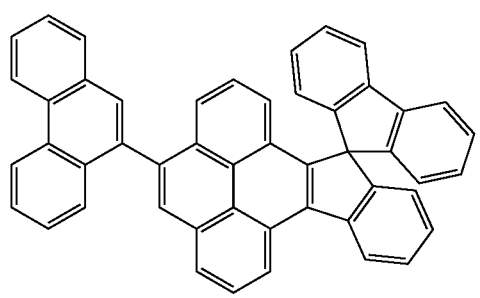
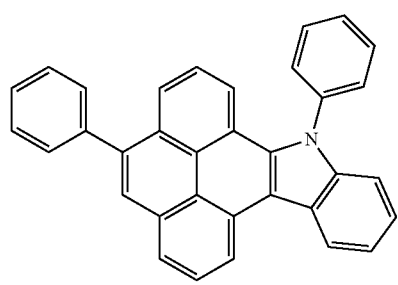

-continued
[Chemical Formula 5-2]
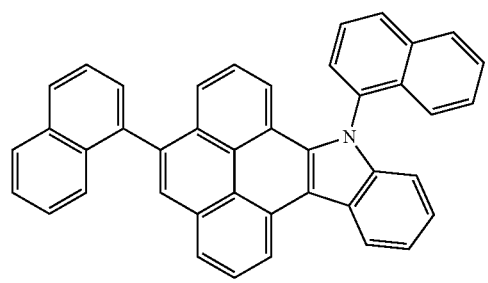
[Chemical Formula 5-3]
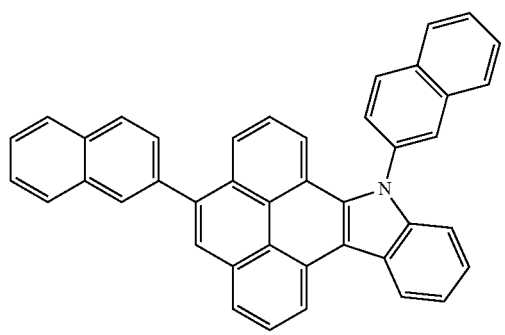
[Chemical Formula 5-4]
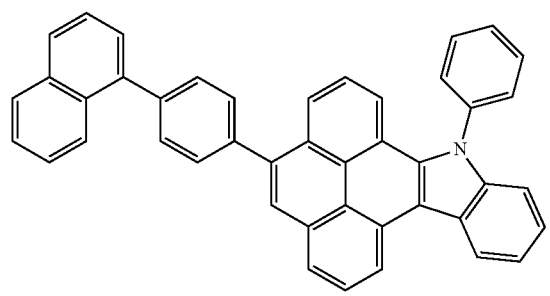
[Chemical Formula 5-5]
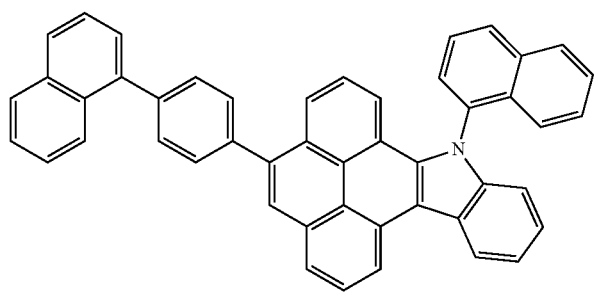
[Chemical Formula 5-6]
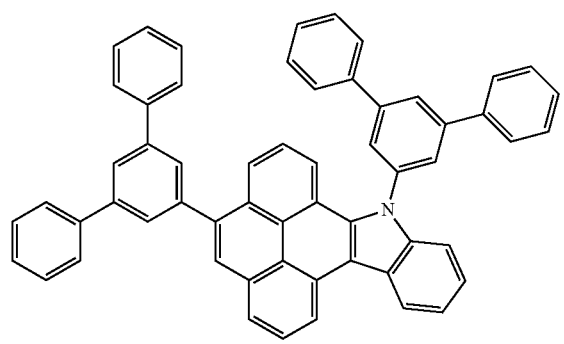
[Chemical Formula 5-7]
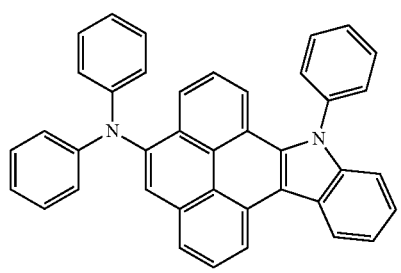
[Chemical Formula 5-8]
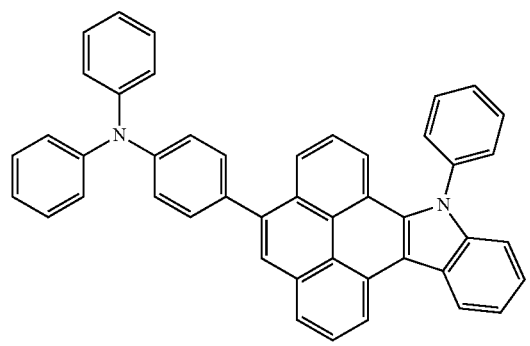
[Chemical Formula 5-9]
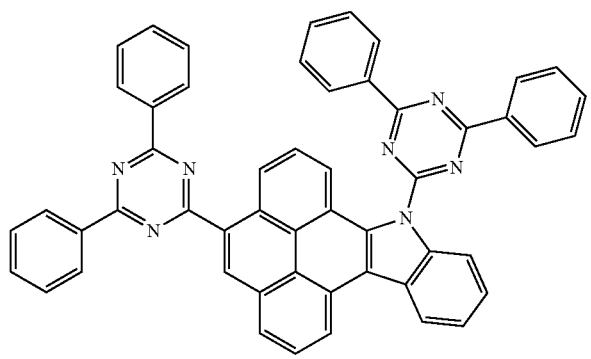

[Chemical Formula 5-10]
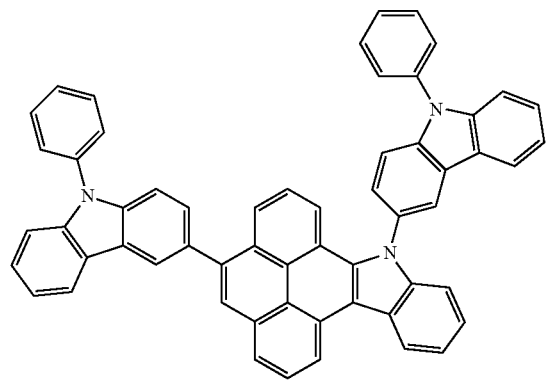
[Chemical Formula 5-11]
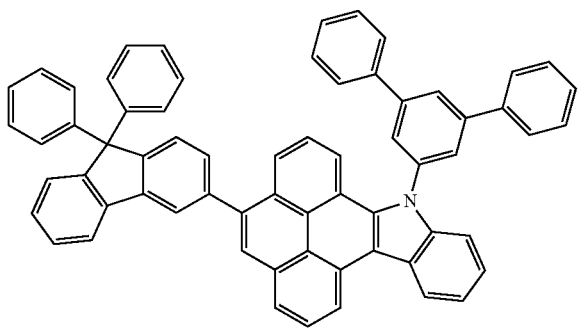
[Chemical Formula 5-12]
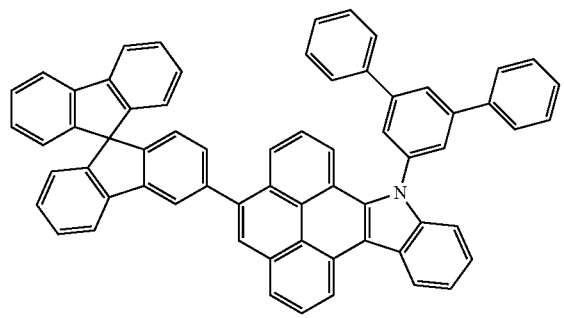
[Chemical Formula 5-13]
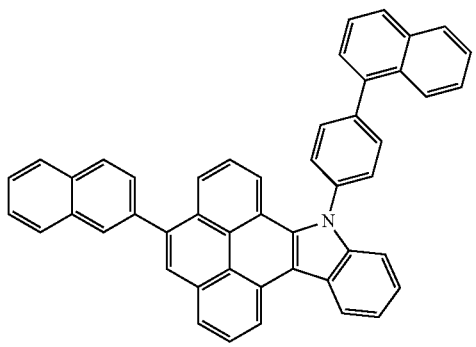
[Chemical Formula 5-14]
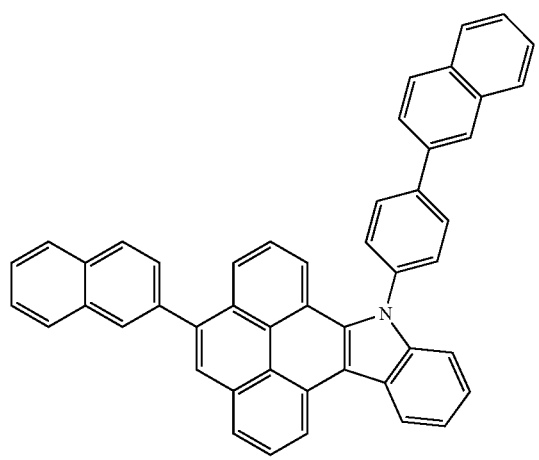
[Chemical Formula 5-15]
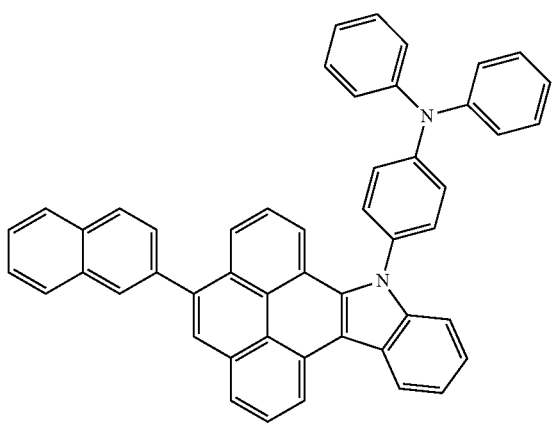

[Chemical Formula 5-16]
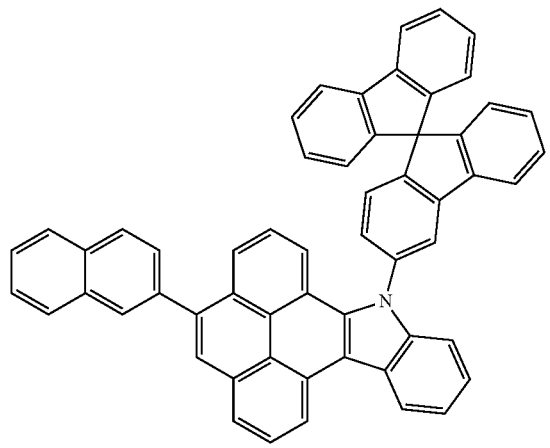
[Chemical Formula 5-17]
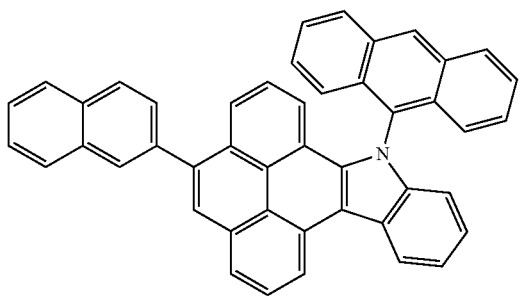
[Chemical Formula 5-18]
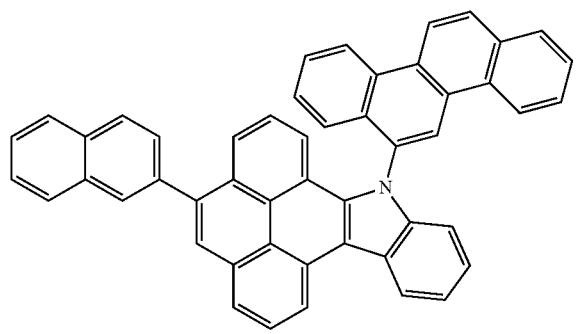
[Chemical Formula 5-19]
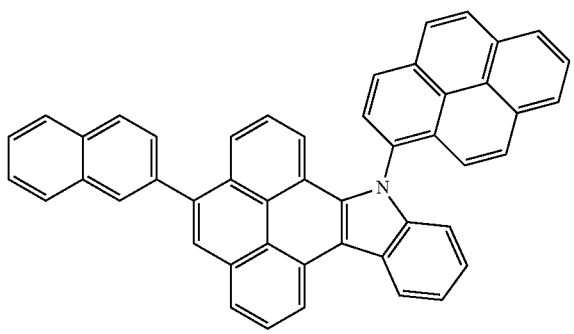
[Chemical Formula 5-20]
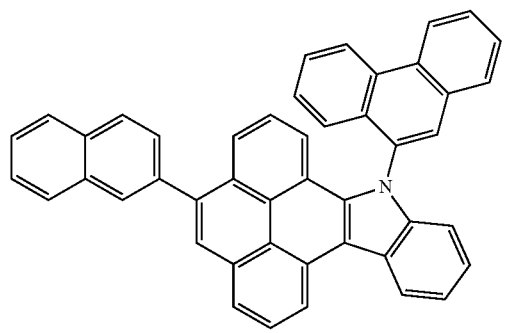
[Chemical Formula 5-21]
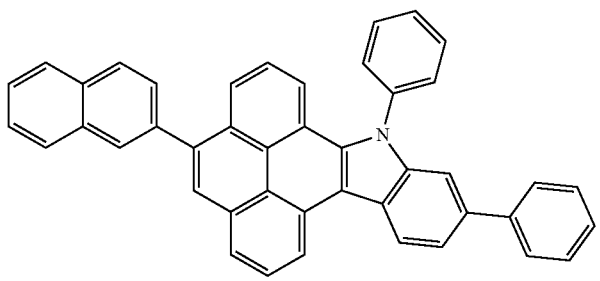
[Chemical Formula 5-22]
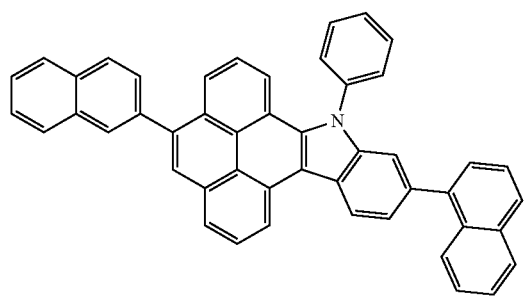
[Chemical Formula 5-23]
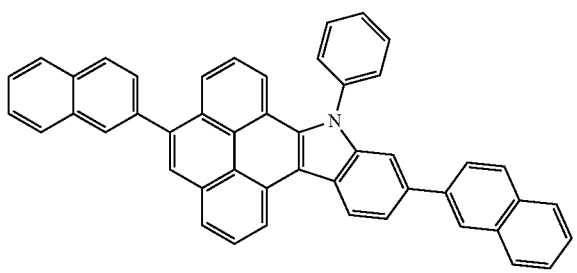

[Chemical Formula 5-24]
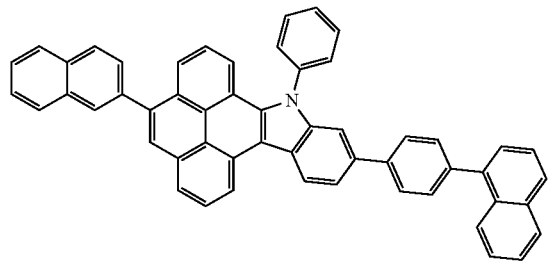
[Chemical Formula 5-25]
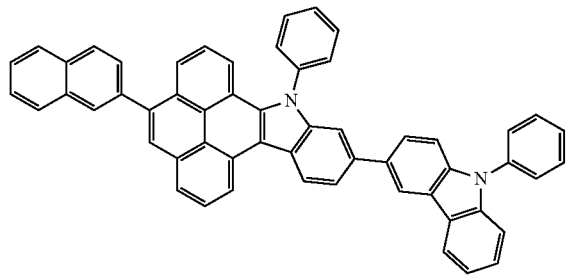
[Chemical Formula 5-26]
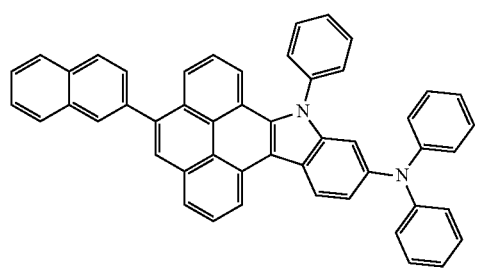
[Chemical Formula 5-27]
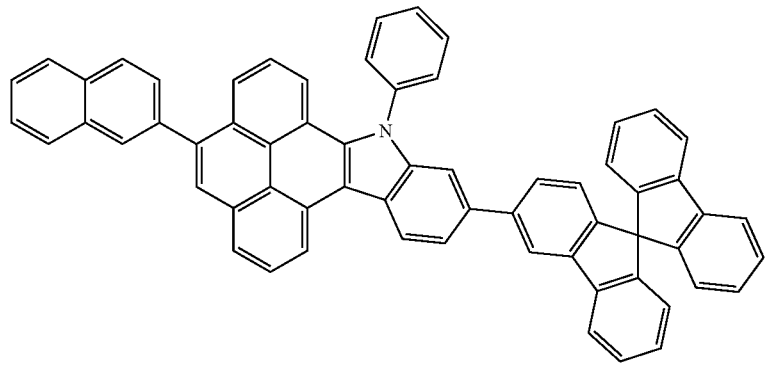
[Chemical Formula 5-28]
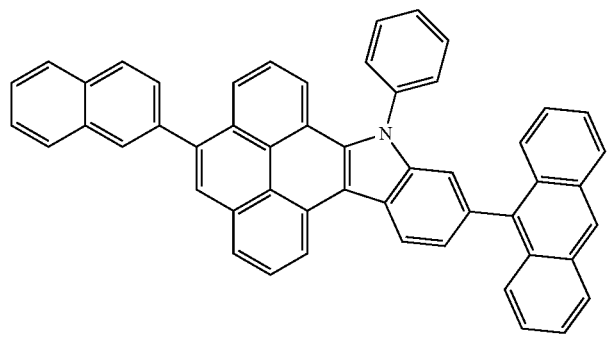
[Chemical Formula 5-29]
[Chemical Formula 5-30]
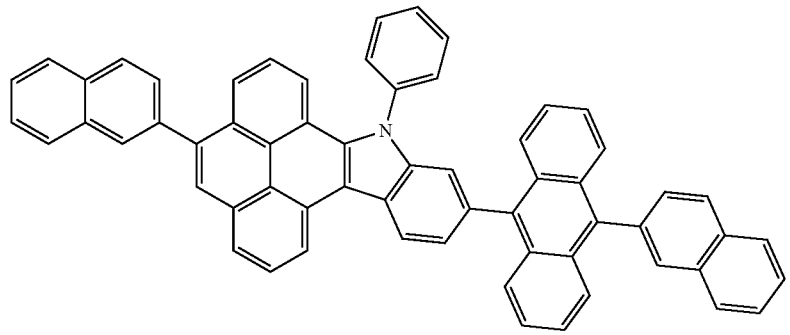

-continued
[Chemical Formula 5-31]
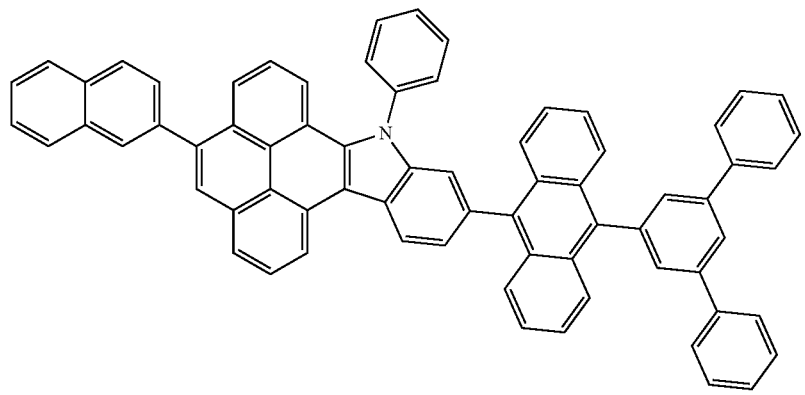
[Chemical Formula 5-32]
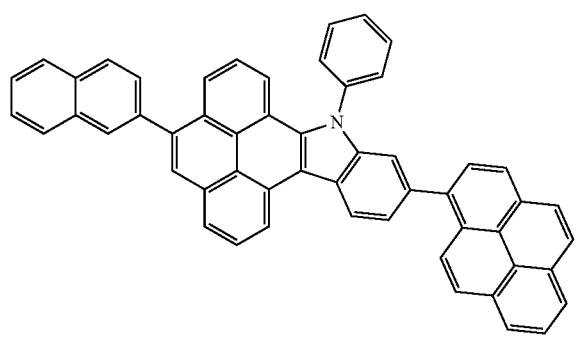
[Chemical Formula 5-33]
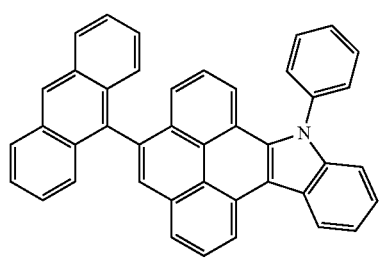
[Chemical Formula 5-34]
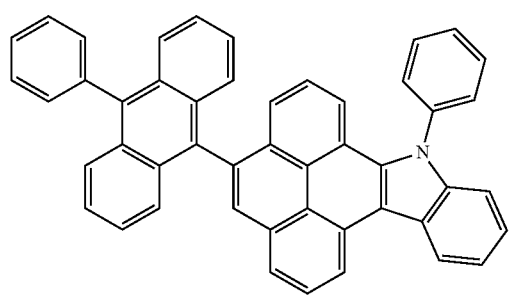
[Chemical Formula 5-35]
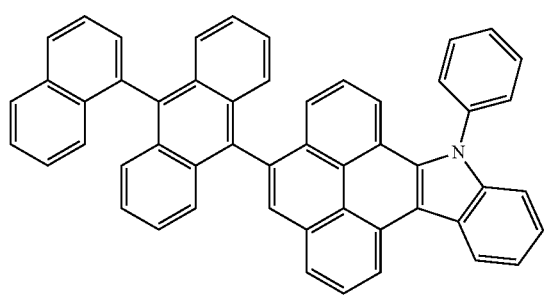
[Chemical Formula 5-36]
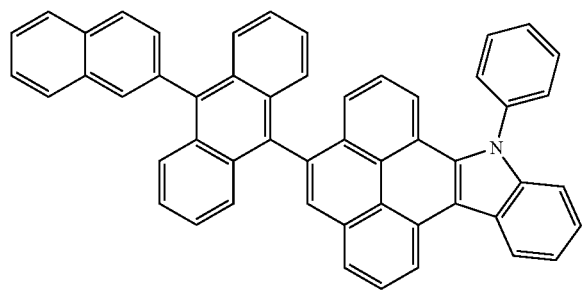

-continued
[Chemical Formula 5-37]
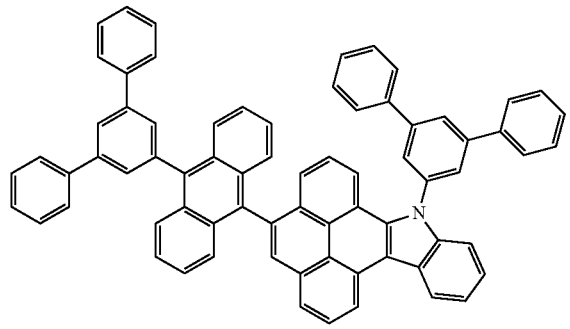
[Chemical Formula 5-38]
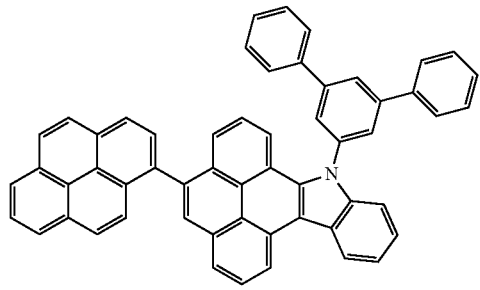
[Chemical Formula 5-39]
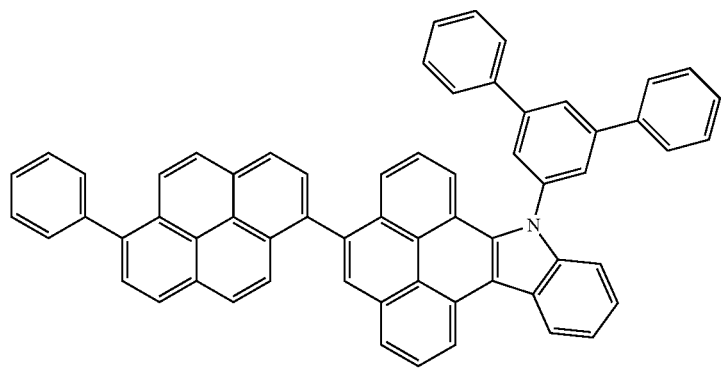
[Chemical Formula 5-40]
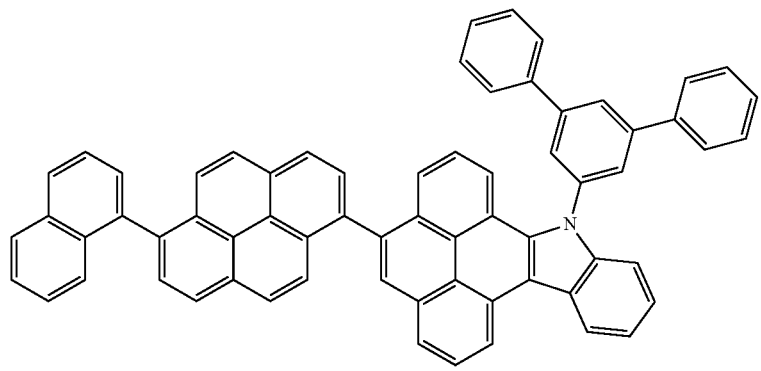
[Chemical Formula 5-41]
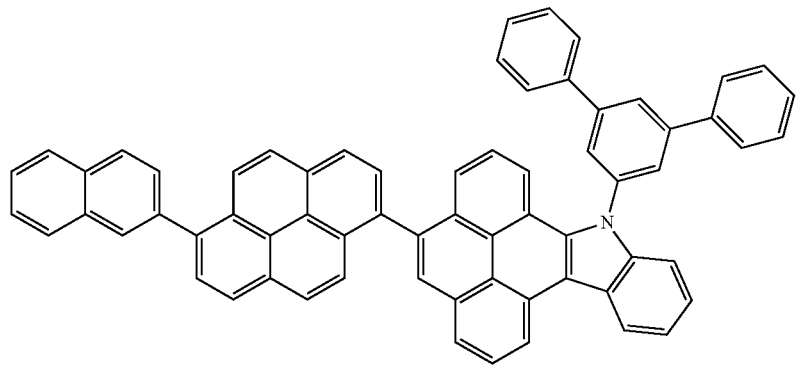

-continued
[Chemical Formula 5-42]
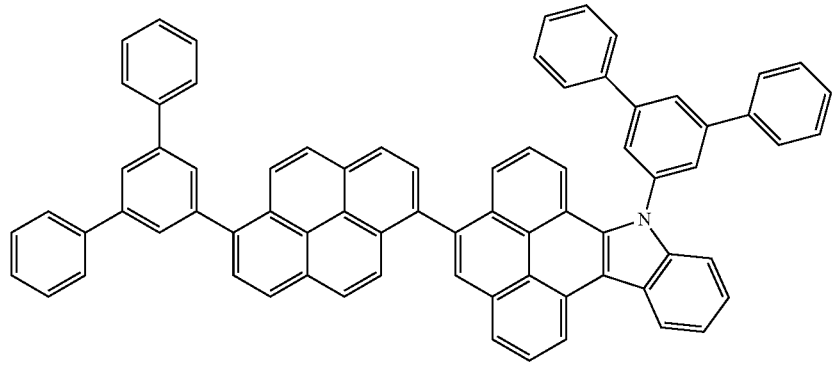
[Chemical Formula 5-43]
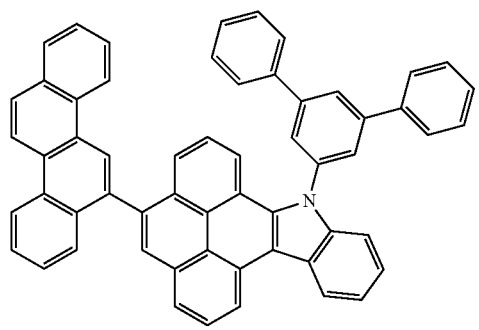
[Chemical Formula 5-44]
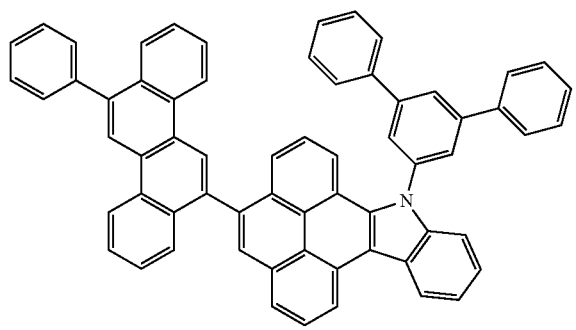
[Chemical Formula 5-45]
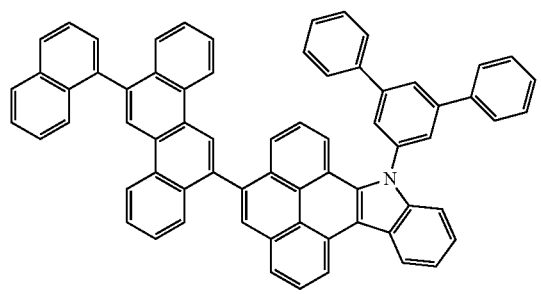
[Chemical Formula 5-46]
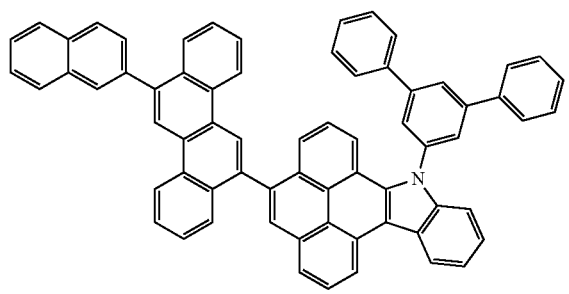
[Chemical Formula 5-47]
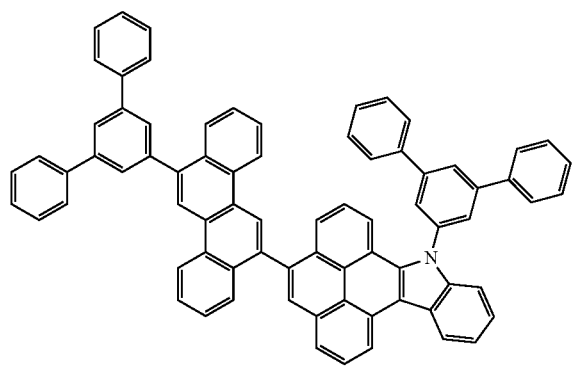
[Chemical Formula 5-48]
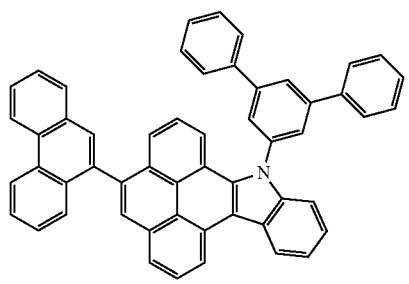

[Chemical Formula 5-49]
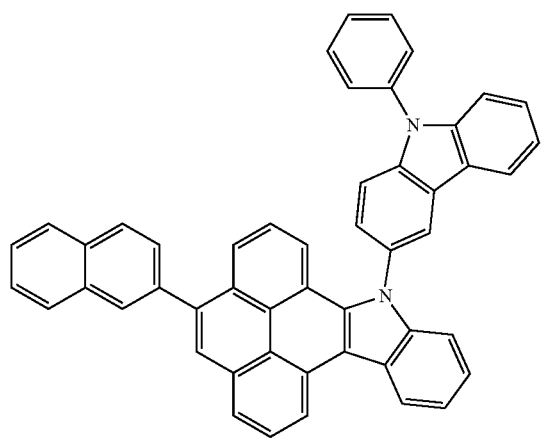
[Chemical Formula 6-1]
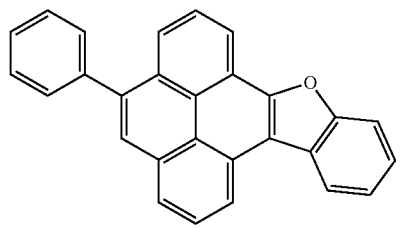
[Chemical Formula 6-2]
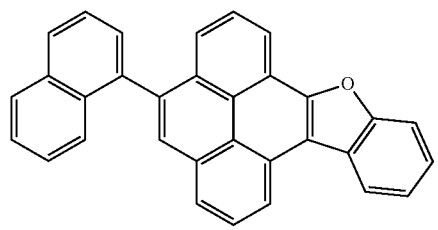
[Chemical Formula 6-3]
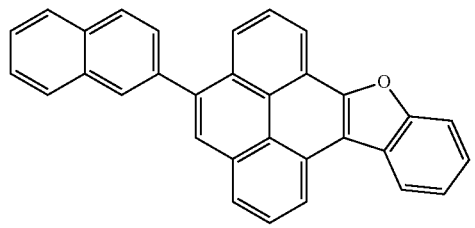
[Chemical Formula 6-4]
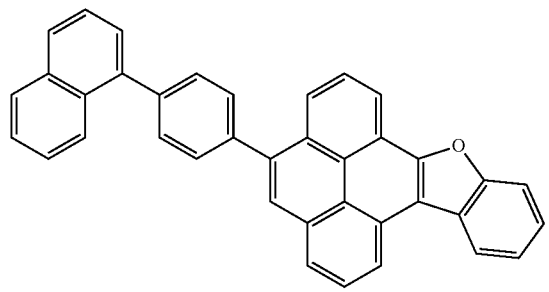
[Chemical Formula 6-5]
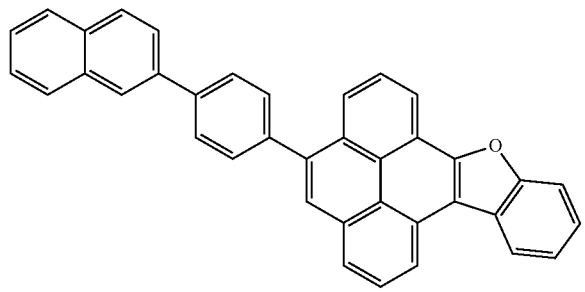
[Chemical Formula 6-6]
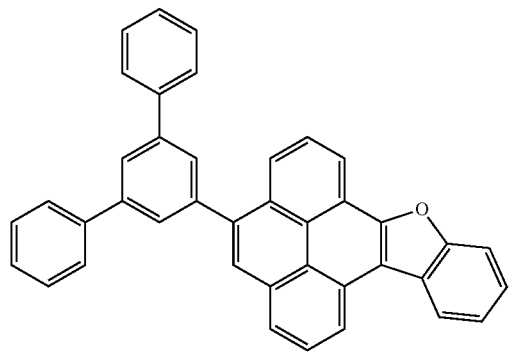
[Chemical Formula 6-7]
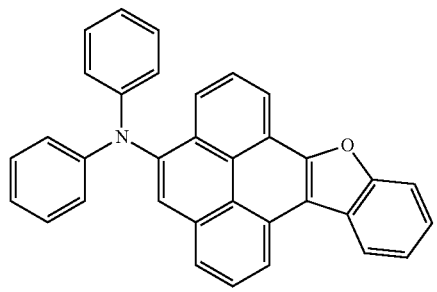

[Chemical Formula 6-8]
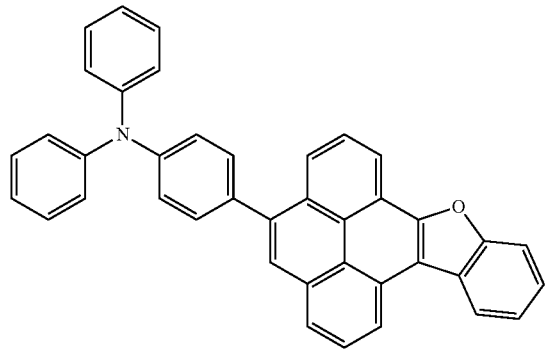
[Chemical Formula 6-9]
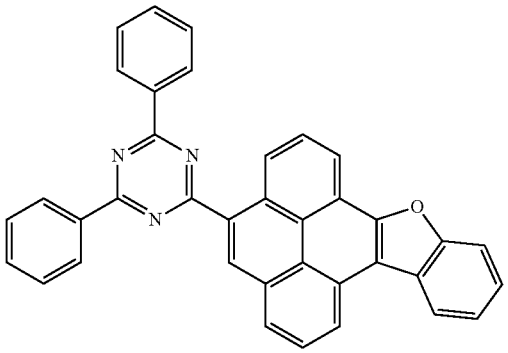
[Chemical Formula 6-10]
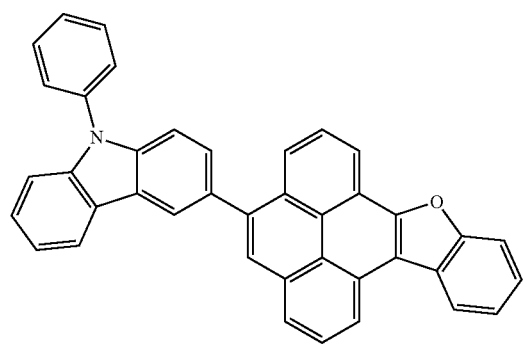
[Chemical Formula 6-11]
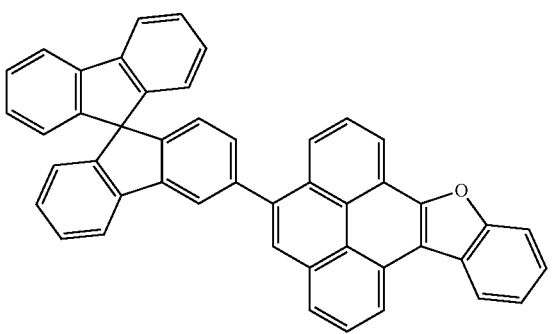
[Chemical Formula 6-12]
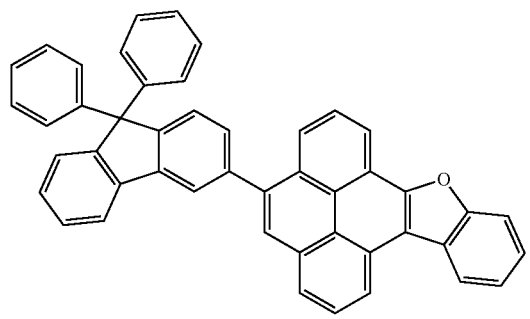
[Chemical Formula 6-13]
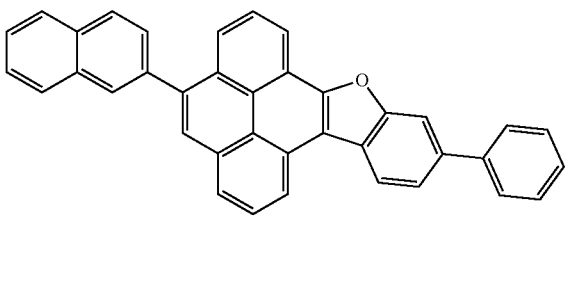
[Chemical Formula 6-14]
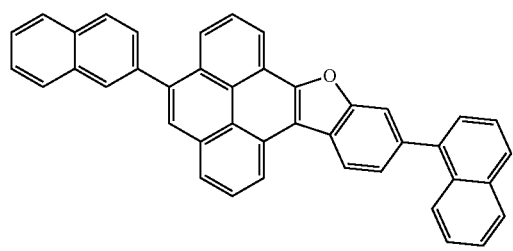
[Chemical Formula 6-15]
[Chemical Formula 6-16]
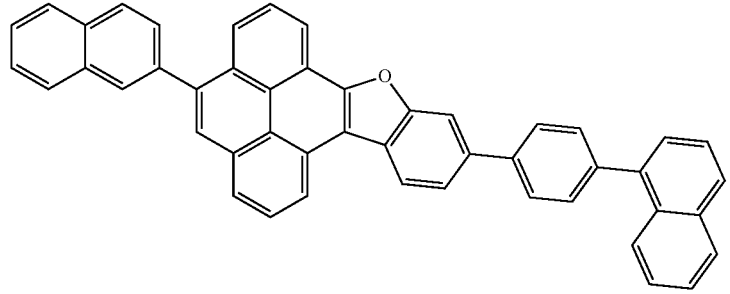

[Chemical Formula 6-17]
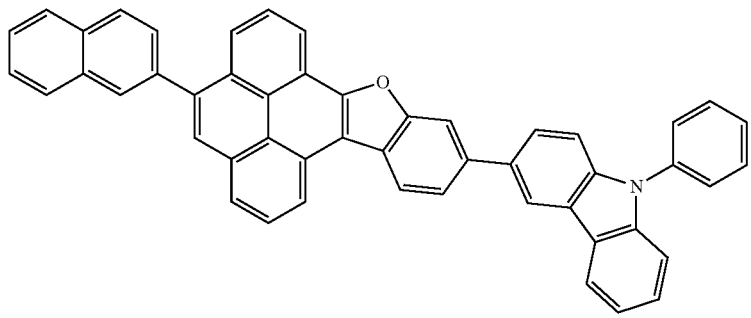
[Chemical Formula 6-18]
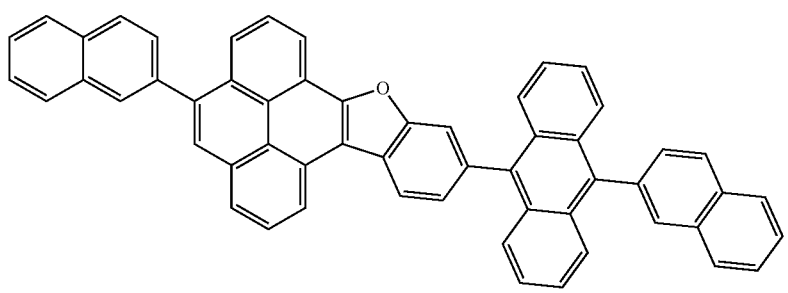
[Chemical Formula 6-19]
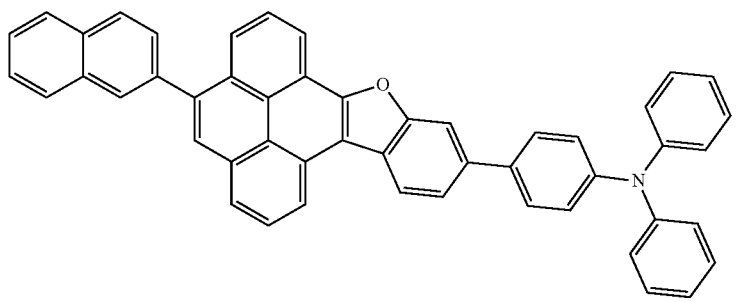
[Chemical Formula 6-20]
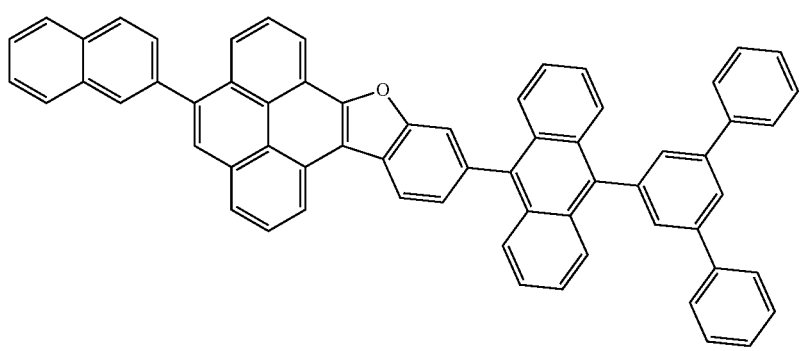
[Chemical Formula 6-21]
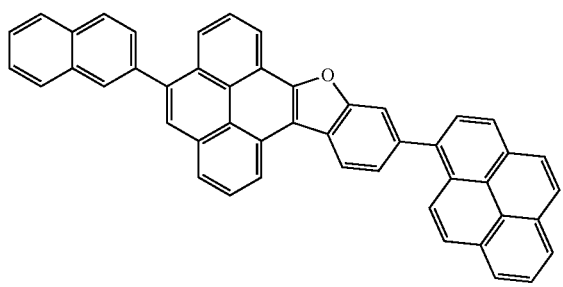
[Chemical Formula 6-22]
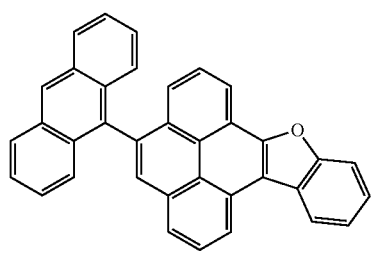

-continued
[Chemical Formula 6-23]
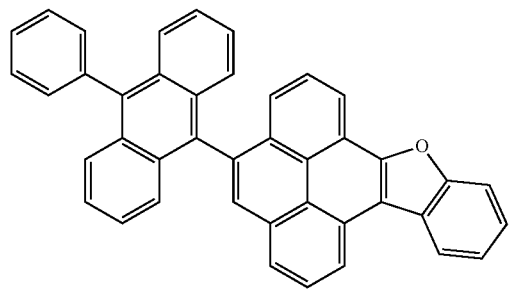
[Chemical Formula 6-24]
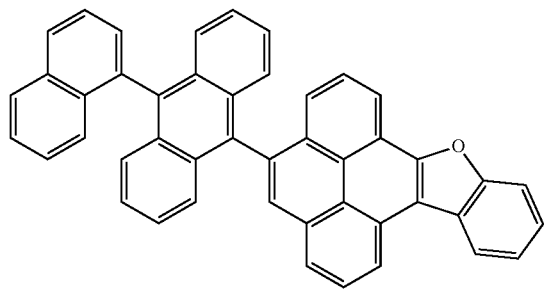
[Chemical Formula 6-25]
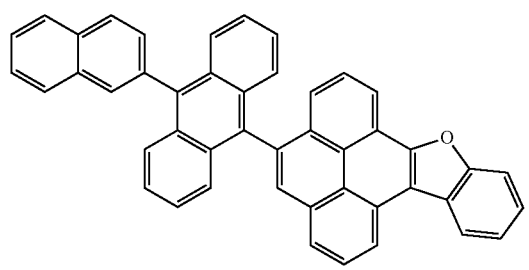
[Chemical Formula 6-26]
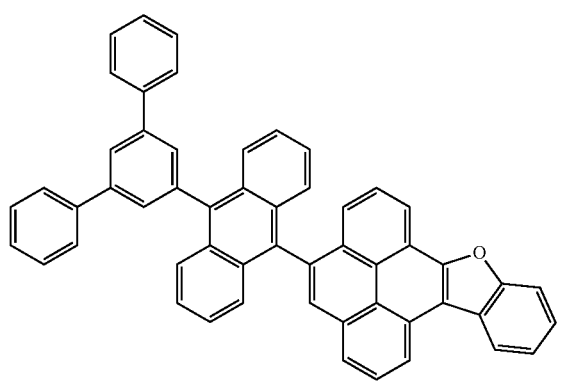
[Chemical Formula 6-27]
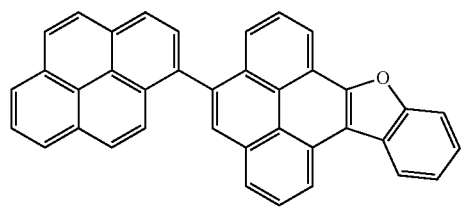
[Chemical Formula 6-28]
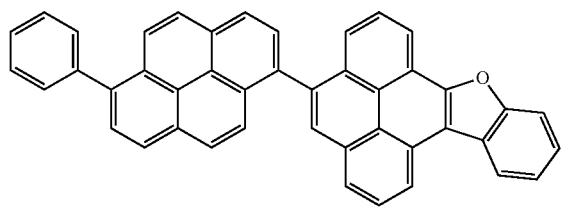
[Chemical Formula 6-29]
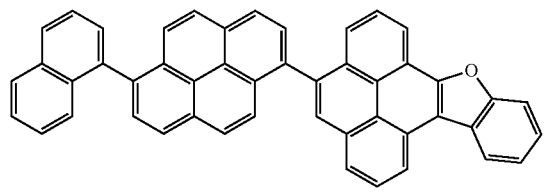
[Chemical Formula 6-30]
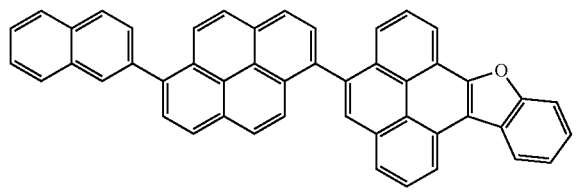
[Chemical Formula 6-31]
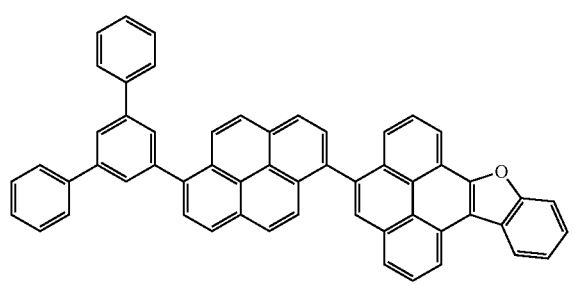
[Chemical Formula 6-32]
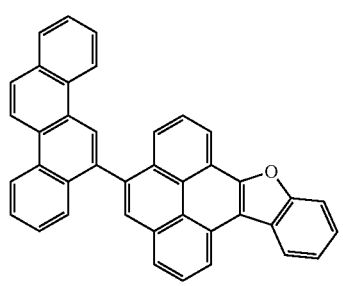

[Chemical Formula 6-33]
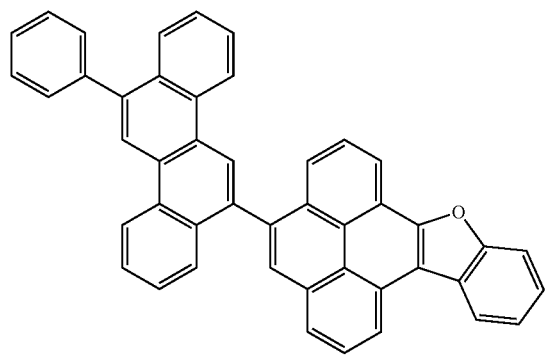
[Chemical Formula 6-34]
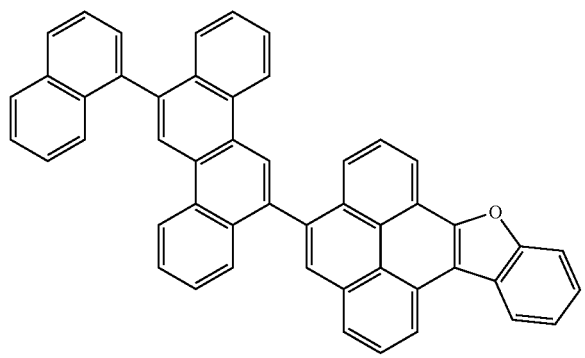
[Chemical Formula 6-35]
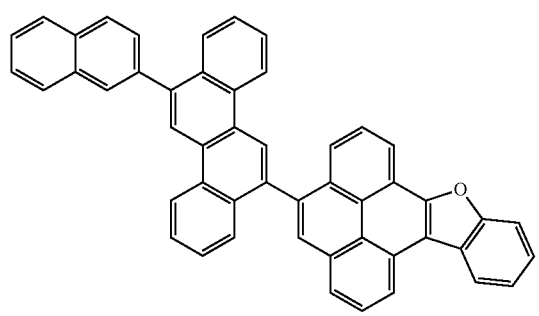
[Chemical Formula 6-36]
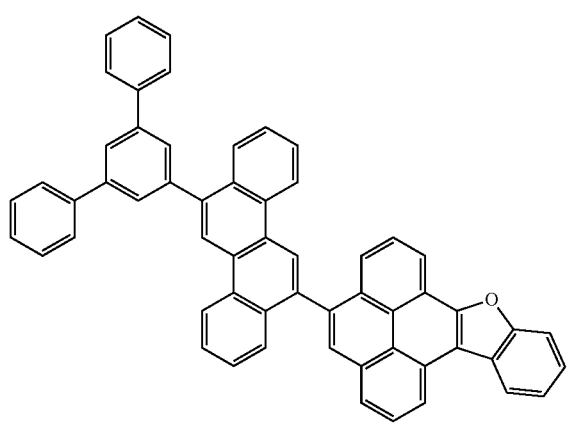
[Chemical Formula 6-37]
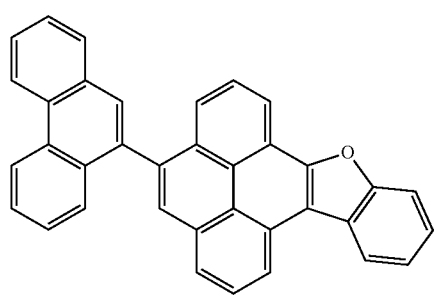
[Chemical Formula 7-1]
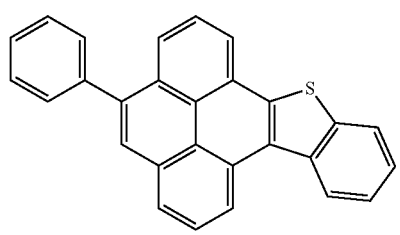
[Chemical Formula 7-2]
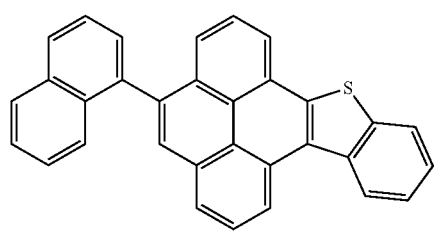
[Chemical Formula 7-3]
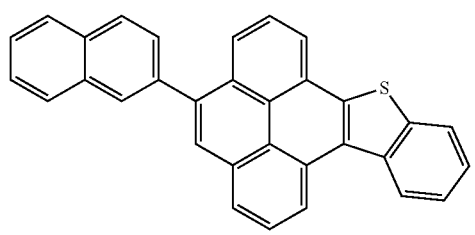

[Chemical Formula 7-4]
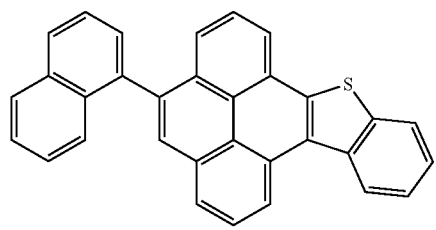
[Chemical Formula 7-5]
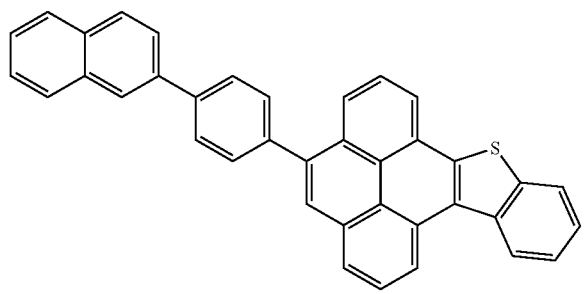
[Chemical Formula 7-6]
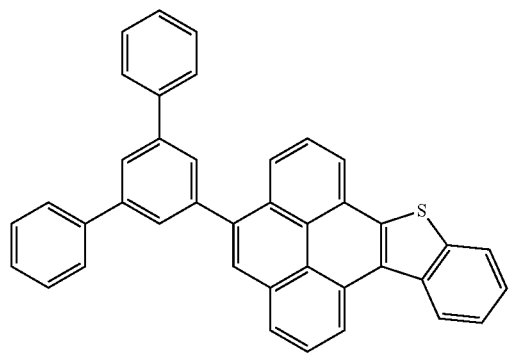
[Chemical Formula 7-7]
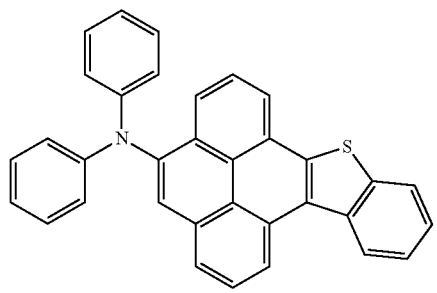
[Chemical Formula 7-8]
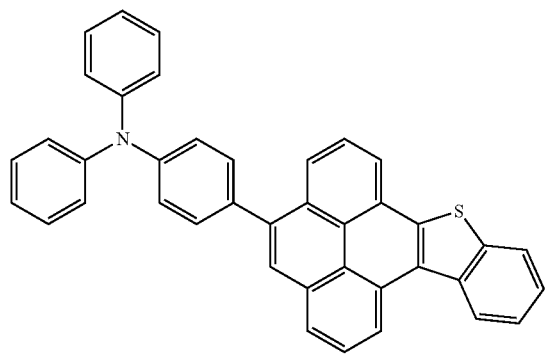
[Chemical Formula 7-9]
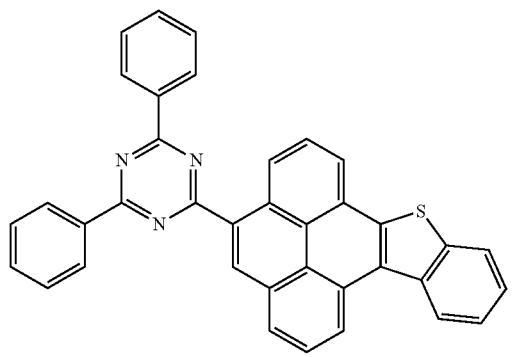
[Chemical Formula 7-10]
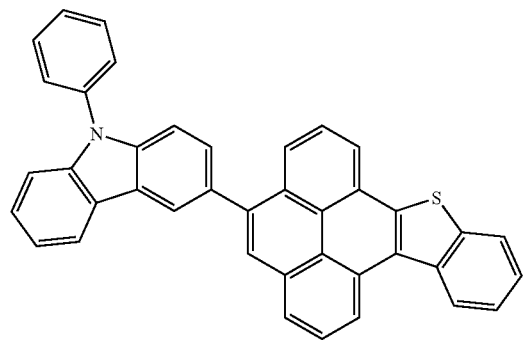
[Chemical Formula 7-11]
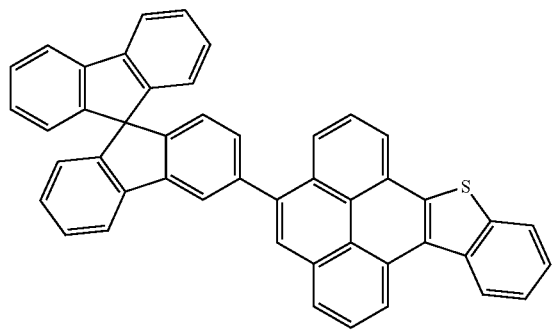

[Chemical Formula 7-12]
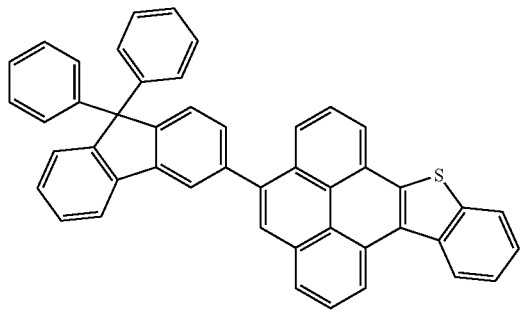
[Chemical Formula 7-13]
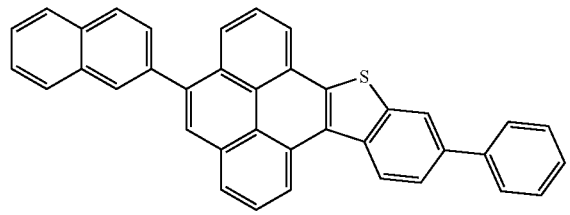
[Chemical Formula 7-14]
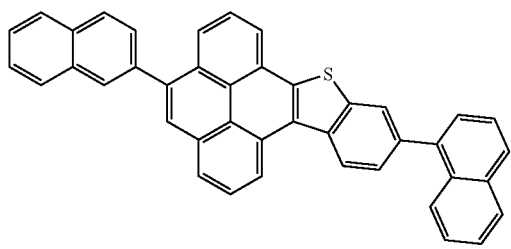
[Chemical Formula 7-15]
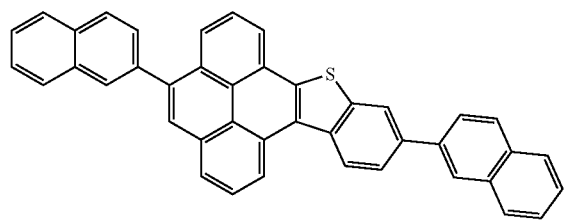
[Chemical Formula 7-16]
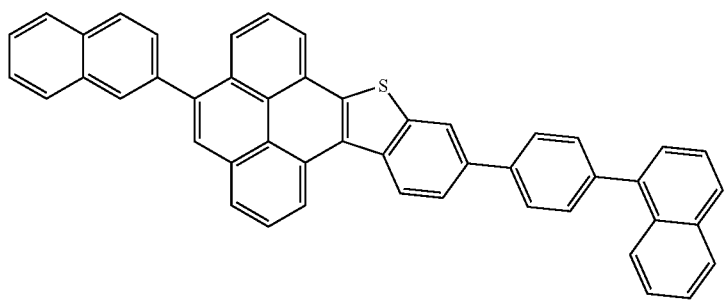
[Chemical Formula 7-17]
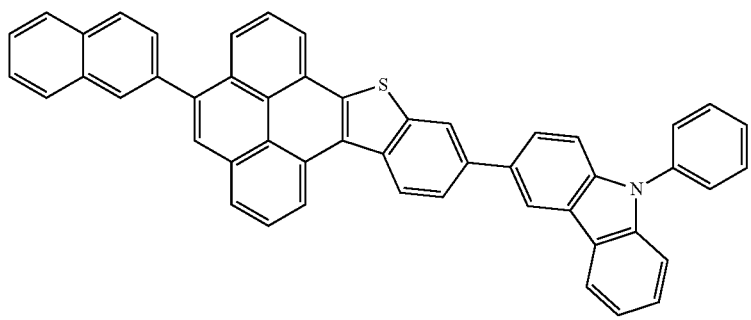
[Chemical Formula 7-18]
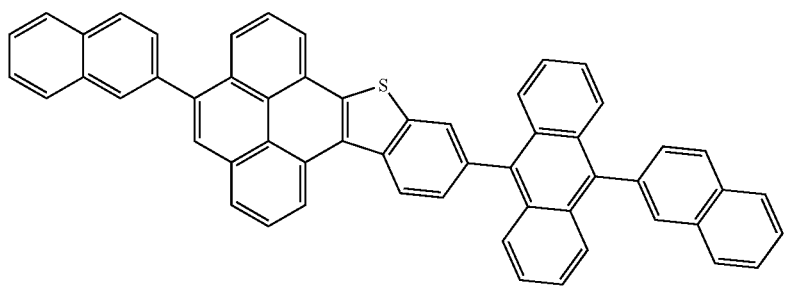

[Chemical Formula 7-19]
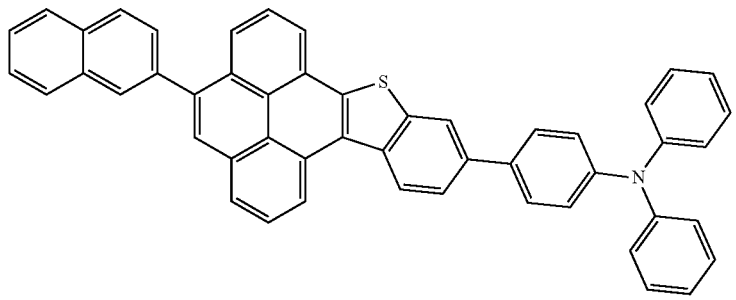
[Chemical Formula 7-20]
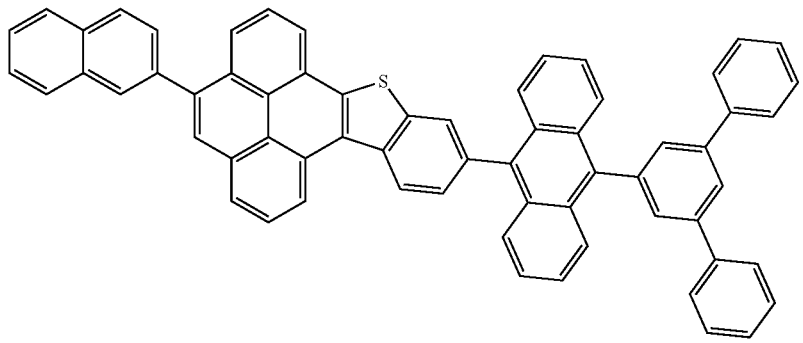
[Chemical Formula 7-21]
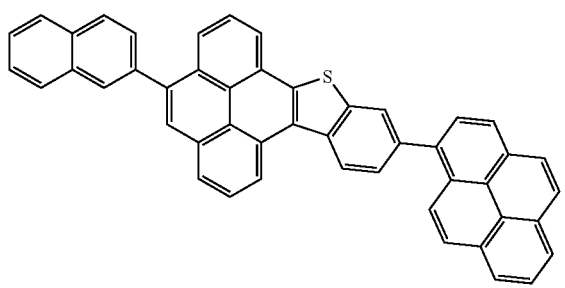
[Chemical Formula 7-22]
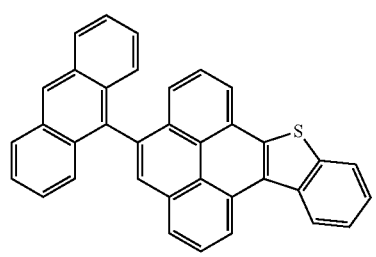
[Chemical Formula 7-23]
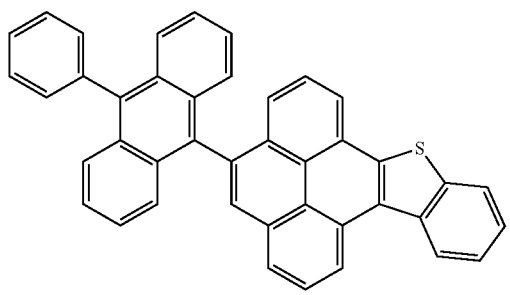
[Chemical Formula 7-24]
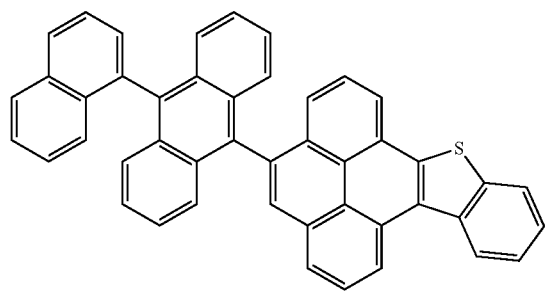
[Chemical Formula 7-25]
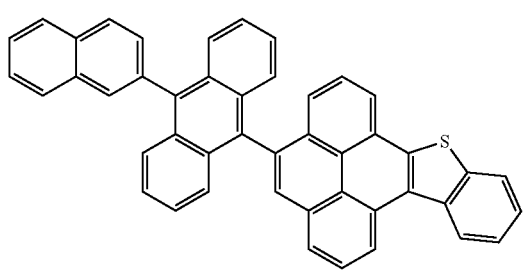
[Chemical Formula 7-26]
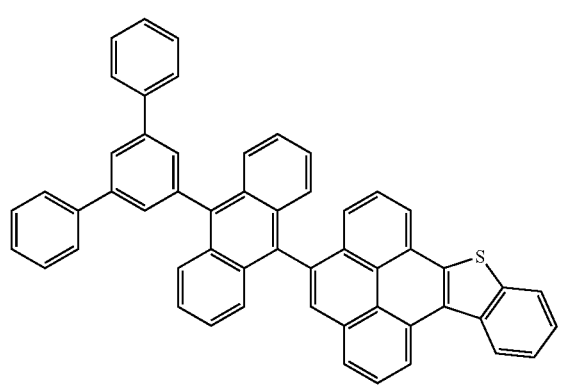

-continued
[Chemical Formula 7-27]
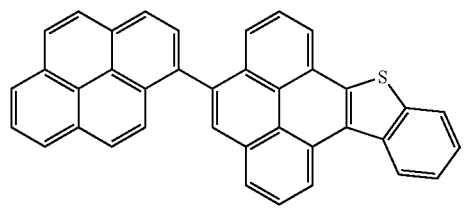
[Chemical Formula 7-28]
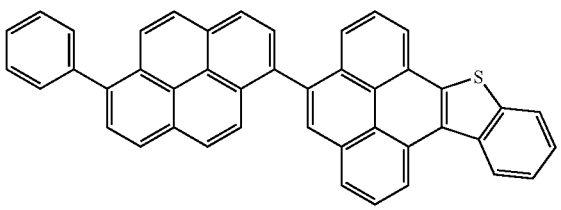
[Chemical Formula 7-29]
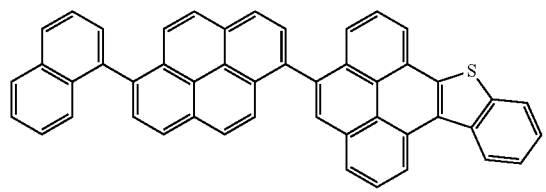
[Chemical Formula 7-30]
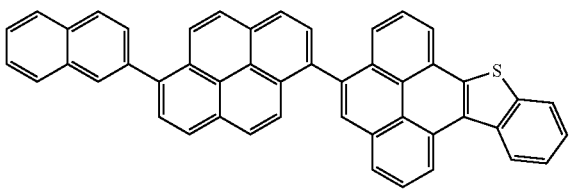
[Chemical Formula 7-31]
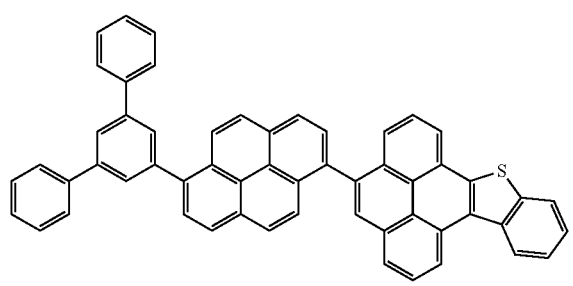
[Chemical Formula 7-32]
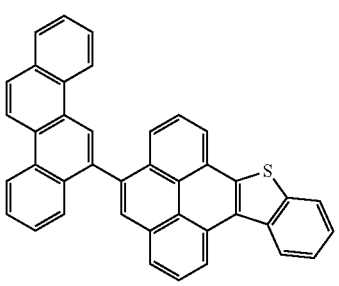
[Chemical Formula 7-33]
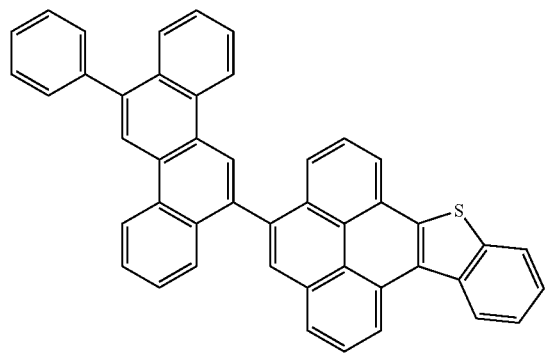
[Chemical Formula 7-34]
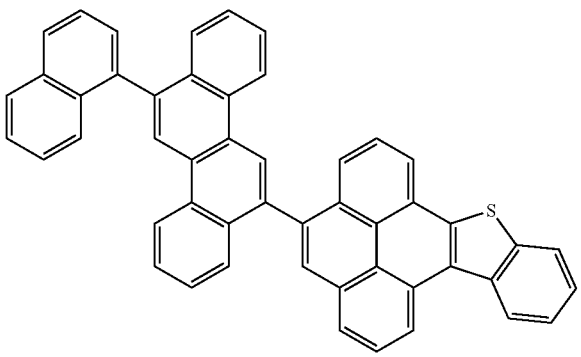
[Chemical Formula 7-35]
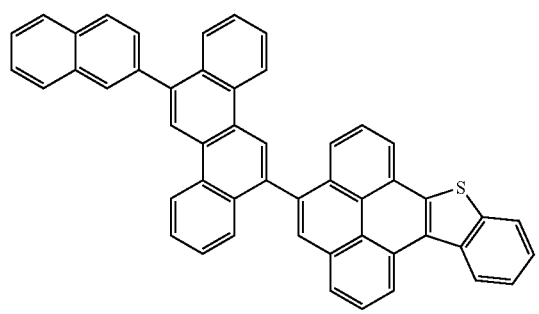
[Chemical Formula 7-36]
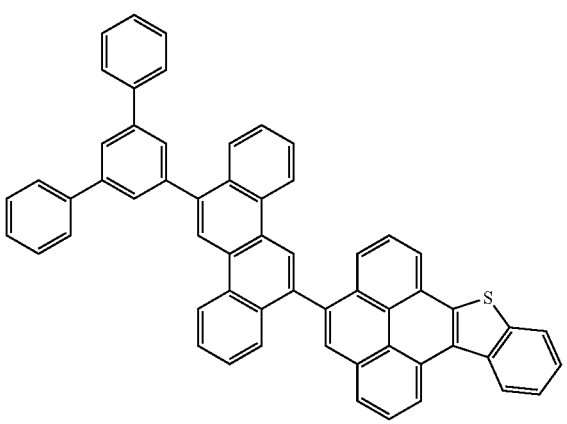

-continued

[Chemical Formula 7-37]

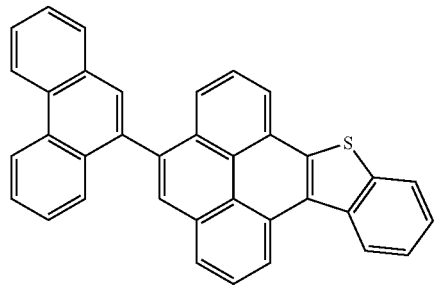

The organic compound may be applicable to various organic optoelectronic devices, for example as a host. The organic compound may be formed using a dry film forming method such as a chemical vapor deposition (CVD) or a solution process.

Hereinafter, an organic optoelectronic device including the organic compound is described.

The organic optoelectronic device may be any device that converts electrical energy into photoenergy and vice versa without particular limitation, and may be, for example, an organic photoelectric device, an organic light emitting diode, an organic solar cell, an organic transistor, an organic photo conductor drum, an organic memory device, and the like.

The organic optoelectronic device may include an anode and a cathode facing each other, and at least one organic layer between the anode and the cathode, wherein the organic layer includes the organic compound.

Herein, an organic light emitting diode as one example of an organic optoelectronic device is described referring to drawings.

FIG. 1 is a cross-sectional view of an organic light emitting diode according to an embodiment.

Referring to FIG. 1, an organic light emitting diode 100 according to an embodiment includes a first electrode 110 and a second electrode 120 facing each other, and an organic layer 105 between the first electrode 110 and the second electrode 120.

One of the first electrode 110 and the second electrode 120 is a cathode and the other is an anode.

At least one of the first electrode 110 and the second electrode 120 may be a transparent electrode, and when the first electrode 110 is a transparent electrode, a bottom emission type in which light is emitted toward the first electrode 110 is realized, while when the second electrode 120 is a transparent electrode, a top emission type in which light is emitted toward the second electrode 120 is realized. In addition, when the first electrode 110 and the second electrode 120 are both transparent electrodes, both-side emission is realized.

The organic layer 105 may include the organic compound. The organic layer 105 may include at least one layer, and may include a light emitting layer, an auxiliary layer, or a combination thereof.

The emission layer may include the compound, for example the compound alone, a mixture of at least two kinds of the compound, or a mixture of the compound and another compound.

The organic layer 105 may further include an auxiliary layer in addition to the light emitting layer. The auxiliary layer may improve luminous efficiency, and may be disposed at at least one of between the first electrode 110 and the light emitting layer and between the second electrode 120 and the light emitting layer. The auxiliary layer may include at least one layer of an electron transport layer and a hole transport layer for balancing between electrons and holes, and an electron injection layer and a hole injection layer for reinforcing injection of electrons and holes.

The organic light emitting diode may be applied to an organic light emitting display device.

Hereinafter, the embodiments are illustrated in more detail with reference to examples. These examples, however, are not in any sense to be interpreted as limiting the scope of the invention.

Synthesis of Organic Compounds

Comparative Synthesis Example 1: Synthesis of Chemical Formula 8

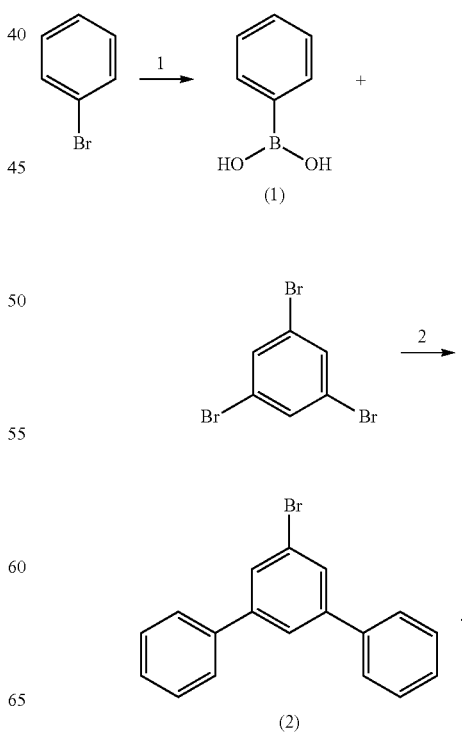

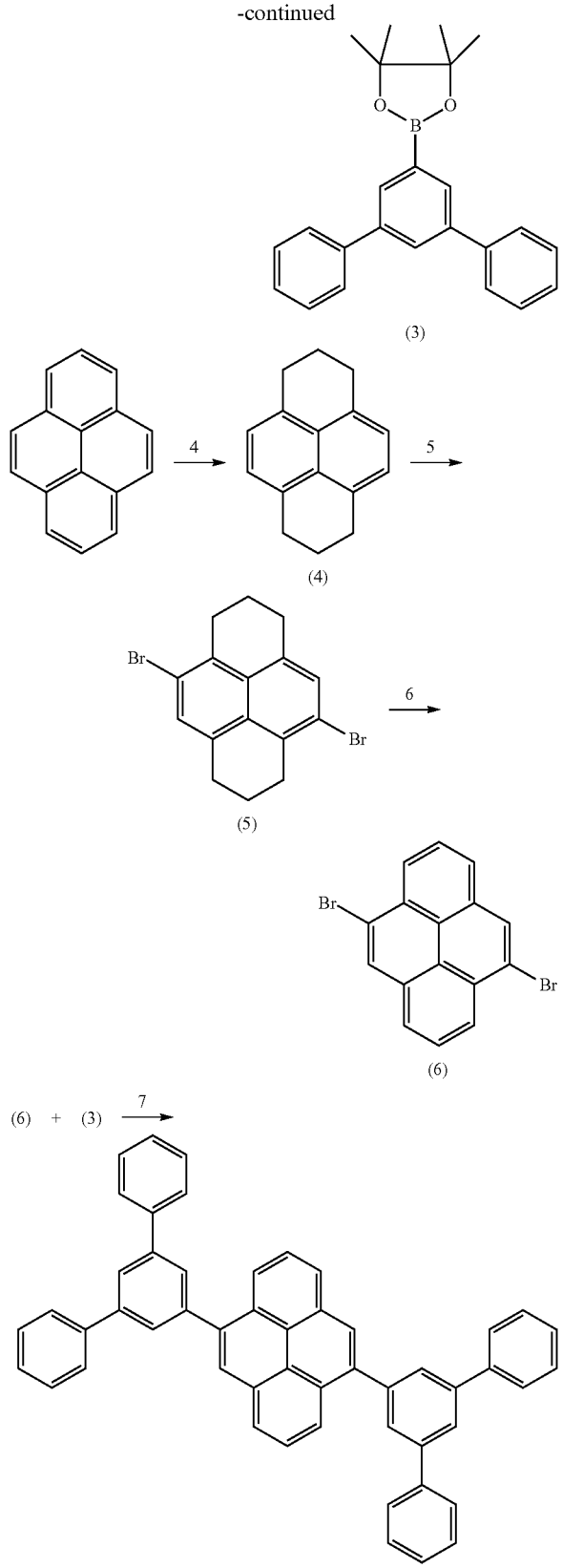

Chemical Formula 8

(1) 10 ml (0.0933 mol) of bromobenzene was put in a flask, and 100 ml of anhydrous THF was added thereto under a nitrogen condition. 55.98 ml of 2 M n-BuLi was slowly added thereto, while the flask was maintained at −78° C. 22.20 ml of triethyl borate was added thereto at −78° C., and the obtained mixture was reacted. When the reaction was complete, 16.33 ml of HCl was added thereto after increasing the temperature up to room temperature, and ethyl acetate (EA) and water was used for an extraction. After removing a solvent therein with an evaporator, 9.410 g of a white solid compound (Intermediate (1)) (a yield of 82.72%), a product in the ethyl acetate (EA) layer, was obtained.

(2) 4.85 g (19.88 mmol) of Intermediate (1), 5.0 g (15.90 mmol) of 1,3,5-tribromobenzene, and 0.92 g of Pd(pph$_3$)$_4$ were put in a flask, 100 ml of anhydrous toluene was added thereto under a nitrogen condition, and the mixture was stirred. Subsequently, 10.0 ml of 2 M K$_2$CO$_3$ was added thereto. Herein, the obtained mixture was stirred, while maintained at about 80° C. When a reaction was complete, chloroform and water were used for an extraction. After removing a solvent by using an evaporator, the resultant was separated and purified with chloroform:hexane=a mixing ratio (a volume ratio) of 1:10 through column chromatography to obtain 2.702 g of a white solid compound, a product in a chloroform layer (Intermediate (2), a yield of 55.3%).

(3) 1.5 g (4.85 mmol) of Intermediate (2) was put in a flask, 100 ml of anhydrous THF was added thereto under a nitrogen condition, and the mixture was stirred. 2.91 ml (5.82 mol) of 2 M n-BuLi was slowly added thereto, while maintained at −78° C. At −78° C., 3.48 ml of 2-isopropoxy-4,4,5,5-tetramethyl-[1,3,2]dioxaborolane was added thereto. When a reaction was complete, ethyl acetate (EA) and water were used for an extraction. A solvent was evaporated therefrom to obtain 1.369 g of a white solid compound, a product in an ethyl acetate (EA) layer (Intermediate (3), a yield of 79.2%).

(4) 20 g (98.8 mmol) of pyrene was put in a flask, 500 ml of 1-pentenol was added thereto, and the mixture was stirred while refluxed. 32 g of sodium was slowly added thereto for one hour, and the obtained mixture was further stirred for 2 hours. After cooled down to room temperature, water was used for an extraction. A solvent was evaporated therefrom, and ethanol was used for a recrystallization to obtain 7.86 g of a white solid compound (Intermediate (4), a yield of 38.2%).

(5) 30 g (144 mmol) of Intermediate (4) was put in a flask, 100 ml of methyl chloride (MC) was added thereto, and the mixture was stirred. 15 ml of Br$_2$ was added to 30 ml of methyl chloride (MC), and this mixed solution was slowly dropped thereto. After reacting the obtained mixture for 30 minutes, a precipitate therein was filtered to obtain 16.9 g of a white solid compound (Intermediate (5), a yield of 32.7%).

(6) 12 g (32.8 mmol) of Intermediate (5) was put in a flask, 22.3 g of 2,3-dichloro-5,6-dicyanobenzoquinone (DDQ) and 240 ml of anhydrous toluene were added thereto under a nitrogen condition, and the mixture was stirred and refluxed. After reacted for 3 hours, the temperature was decreased down to room temperature. The resultant was purified with chloroform through column chromatography and after evaporating a solvent therefrom, recrystallized with chloroform to obtain 4.51 g of a yellow solid compound (Intermediate (6), a yield of 38.2%).

(7) 0.8 g (2.22 mmol) of Intermediate (6), 1.7416 g (4.89 mmol) of Intermediate (3), 0.182 g of Pd(OAc)$_2$, and 0.187 g of tricyclohexylphosphine were put in a flask, 60 ml of anhydrous THF was added thereto under a nitrogen condition, and the mixture was stirred. 20 ml of 20 wt % (Et)$_4$NOH was added thereto, and the obtained mixture was stirred for 6 hours while refluxed. When a reaction was complete, the resultant was extracted by using chloroform and water and then, purified with chloroform:hexane=a mixing ratio (a volume ratio) of 1:5 through column chromatography. Subsequently, the obtained liquid was treated by using an evaporator to obtain 0.309 g of an ivory solid compound (Chemical Formula 8, a yield of 21.1%). [HRMS (FAB+, m/z): calcd. For $C_{52}H_{34}$, 658.2661; found, 658.2656].

Synthesis Example 1: Synthesis of Chemical Formula 4-6

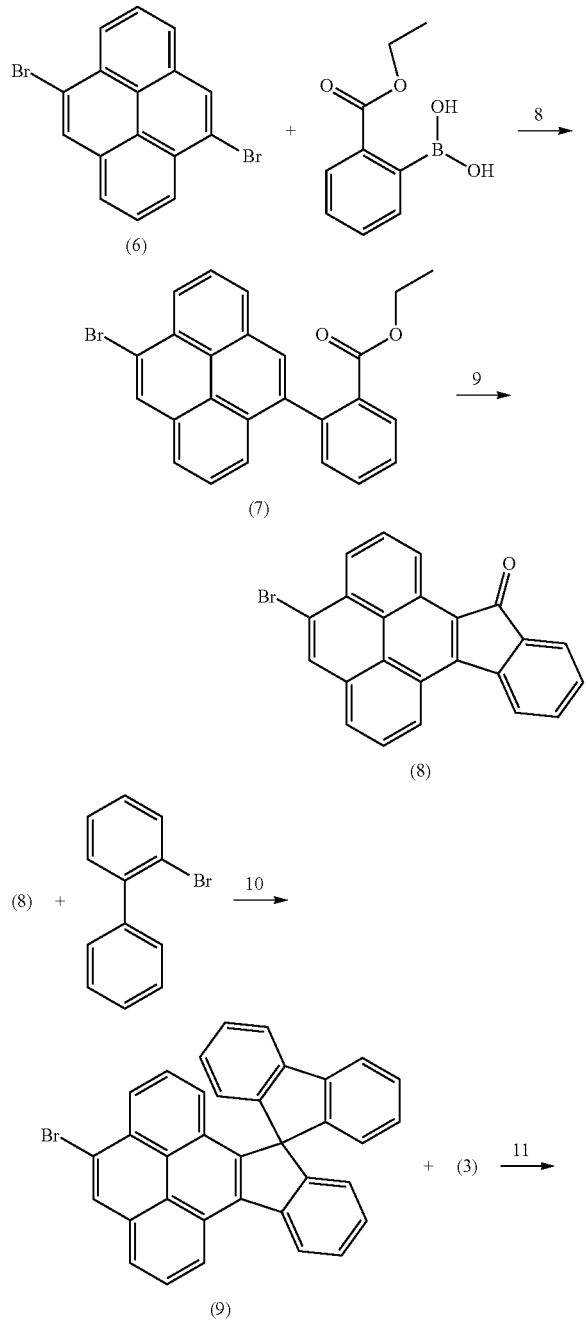

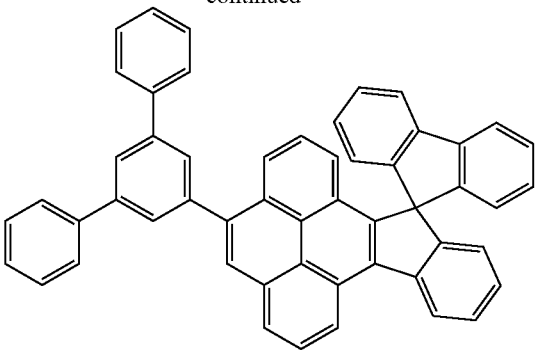

Chemical Formula 4-6

(8) 2.5 g (6.95 mmol) of Intermediate (6), 1.75 g (9.03 mmol) of 2-epoxycarbonylphenyl boronic acid, and 0.4 g of $Pd(pph_3)_4$ were put in a flask, and 50 ml of anhydrous THF was added thereto under a nitrogen condition. 20 ml of 2 M $K_2CO_3$ was added thereto, and the obtained mixture was stirred for 6 hours while refluxed. When a reaction was complete, chloroform and water were used for an extraction. The resultant was purified with ethyl acetate (EA):hexane=a mixing ratio (a volume ratio) of 1:10 through column chromatography. Subsequently, a solvent was evaporated from the obtained liquid with an evaporator to obtain 0.621 g of Intermediate (7) (a yield of 20.2%).

(9) 0.62 g (1.44 mmol) of Intermediate (7) and 10 ml of methane sulfonic acid were put in a flask and then, stirred while maintained at 70° C. After reacted for 4 hours, chloroform and water were used for an extraction. A solvent was evaporated therefrom by using an evaporator to obtain 0.521 g of a yellow solid compound, a product in a chloroform layer (Intermediate (8), a yield of 98.1%).

(10) 0.56 ml (3.27 mmol) of 2-bromobiphenyl and 20 ml of anhydrous THF were put in a flask and cooled down to −78° C. Subsequently, 2.04 ml of 1.6 M t-BuLi was added thereto. A solution obtained by dissolving 0.4 g (1.09 mmol) of intermediate (8) in anhydrous THF was slowly added to the flask in a dropwise fashion. Ethyl acetate (EA) and water were used for an extraction, and a solvent was evaporated therefrom. 20 ml of HCl and 40 ml of acetic acid were added thereto, and the obtained mixture was refluxed for 5 hours. When a reaction was complete, the resultant was extracted with chloroform and then, purified with chloroform:hexane=a mixing ratio (a volume ratio) of 1:10 through column chromatography. Subsequently, a solvent was evaporated from the obtained liquid by using an evaporator to obtain 0.1763 g of a white solid compound (Intermediate (9), a yield of 31.1%).

(11) 0.35 g (0.674 mmol) of Intermediate (9), 0.2641 g (0.741 mmol) of Intermediate (3), 0.0276 g of $Pd(OAc)_2$, and 0.283 g of tricyclohexylphosphine were put in a flask, 30 ml of anhydrous THF was added hereto, and the mixture was stirred under a nitrogen condition. 15 ml of 20 wt % $(Et)_4NOH$ was added thereto, and the obtained mixture was stirred for 6 hours while refluxed. When a reaction was complete, the resultant was extracted with chloroform and water and then, purified with chloroform:hexane=a mixing ratio (a volume ratio) of 1:10 through column chromatography. Subsequently, a solvent was evaporated from the obtained liquid by using an evaporator to obtain 0.362 g of a white solid compound (Chemical Formula 4-6, a yield of 80.4%). [HRMS (FAB+, m/z): calcd. For $C_{53}H_{32}$, 668.2504; found, 668.2504].

Synthesis Example 2: Synthesis of Chemical Formula 5-6

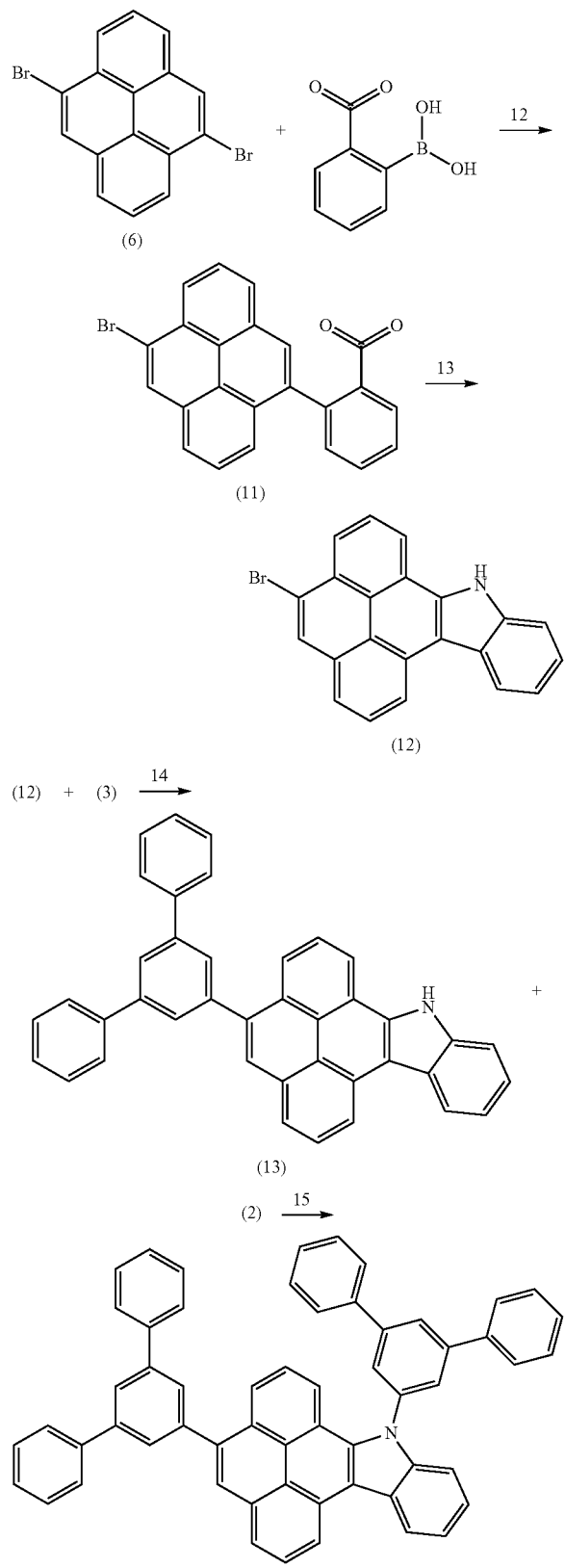

Chemical Formula 5-6

(12) 4.5 g (12.5 mmol) of Intermediate (6), 2.71 g (16.3 mmol) of 2-nitrophenylboronic acid, and 0.722 g of Pd(pph$_3$)$_4$ were put in a flask, and 240 ml of anhydrous THF was added thereto under a nitrogen condition. 100 ml of 2 M K$_2$CO$_3$ was added thereto, and the obtained mixture was stirred for 6 hours while refluxed. When a reaction was complete, chloroform and water were used for an extraction. The resultant was purified with ethyl acetate (EA):hexane=a mixing ratio (a volume ratio) of 1:10 through column chromatography. Subsequently, a solvent was evaporated from the obtained liquid by using an evaporator to obtain 1.578 g of Intermediate (11) (yield of 20.2%).

(13) 1.2 g (3.73 mmol) of Intermediate (11), 6.5 ml of triethylphosphite, and 1,2-dichlorobenzene were put in a flask and then, stirred while refluxed. After reacted for 24 hours, the resultant was purified with ethyl acetate (EA): hexane=a mixing ratio (a volume ratio) of 1:10 through column chromatography. A solvent was evaporated therefrom by using an evaporator to obtain 0.5975 g of a yellow solid compound (Intermediate (12), a yield of 43.3%).

(14) 0.8 g (2.16 mmol) of Intermediate (12), 0.924 g (2.59 mmol) of Intermediate (3), 0.0888 g of Pd(OAc)$_2$, and 0.912 g of tricyclohexylphosphine were put in a flask, 30 ml of anhydrous THF was added thereto, and the mixture was stirred under a nitrogen condition. 15 ml of 2 M K$_2$CO$_3$ was added thereto, and the obtained mixture was stirred for 6 hours while refluxed. When a reaction was complete, the resultant was extracted with chloroform and water and then, purified with ethyl acetate (EA):hexane=a mixing ratio (a volume ratio) of 1:10 through column chromatography. Subsequently, a solvent was removed from the obtained liquid by using an evaporator to obtain 0.6455 g of a yellow solid compound (Intermediate (13), a yield of 57.5%).

(15) 0.4 g (0.770 mmol) of Intermediate (13), 0.75 g of Intermediate (2), 0.0276 g of CuI, 0.203 g of 18-crown-6, and 0.319 g of K$_2$CO$_3$ were put in a flask, 20 ml of anhydrous N,N-dimethyl acetamide was added thereto under a nitrogen condition, and the mixture was stirred. The mixture was stirred for 48 hours while refluxed. When a reaction was complete, the resultant was extracted with chloroform and water and then, purified with chloroform: hexane=a mixing ratio (a volume ratio) of 1:10 through column chromatography. Subsequently, a solvent was evaporated from the obtained liquid to obtain 0.2013 g of a yellow solid compound (Chemical Formula 5-6, a yield of 35.0%). [HRMS (FAB+, m/z): calcd. For C$_{58}$H$_{37}$N, 747.2926; found, 747.2936].

Evaluation 1: Light Absorption Characteristics

Light absorption characteristics of the compounds according to Synthesis Examples 1 and 2 and Comparative Synthesis Example 1 in a solution state and in a thin film state were evaluated.

The light absorption characteristics of the compounds according to Synthesis Examples 1 and 2 and Comparative Synthesis Example 1 in a solution state were evaluated by respectively dissolving the compounds in THF with a concentration of 10-5 M and using a UV-Vis spectrometer (Lambda 1050 UV-Vis.-NIR spectrometer, PerkinElmer), and the light absorption characteristics in a thin film state were evaluated by respectively vacuum-depositing the compounds according to Synthesis Examples 1 and 2 and Comparative Synthesis Example 1 on a glass substrate to form each 50 nm-thick thin film and using the UV-Vis spectrometer (Lambda 1050 UV-Vis.-NIR spectrometer, PerkinElmer).

Figure 2:
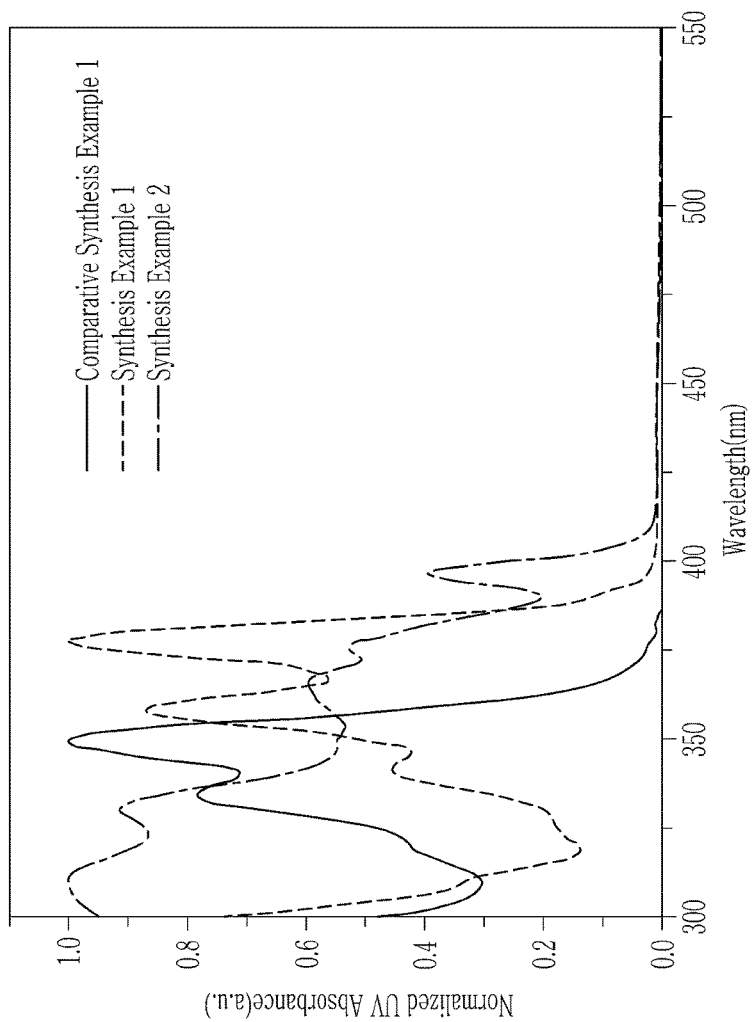
FIG. 2 is a graph showing light absorption characteristics of the compounds obtained in Synthesis Example 1, Synthesis Example 2, and Comparative Synthesis Example 1 in each solution.
Figure 3:
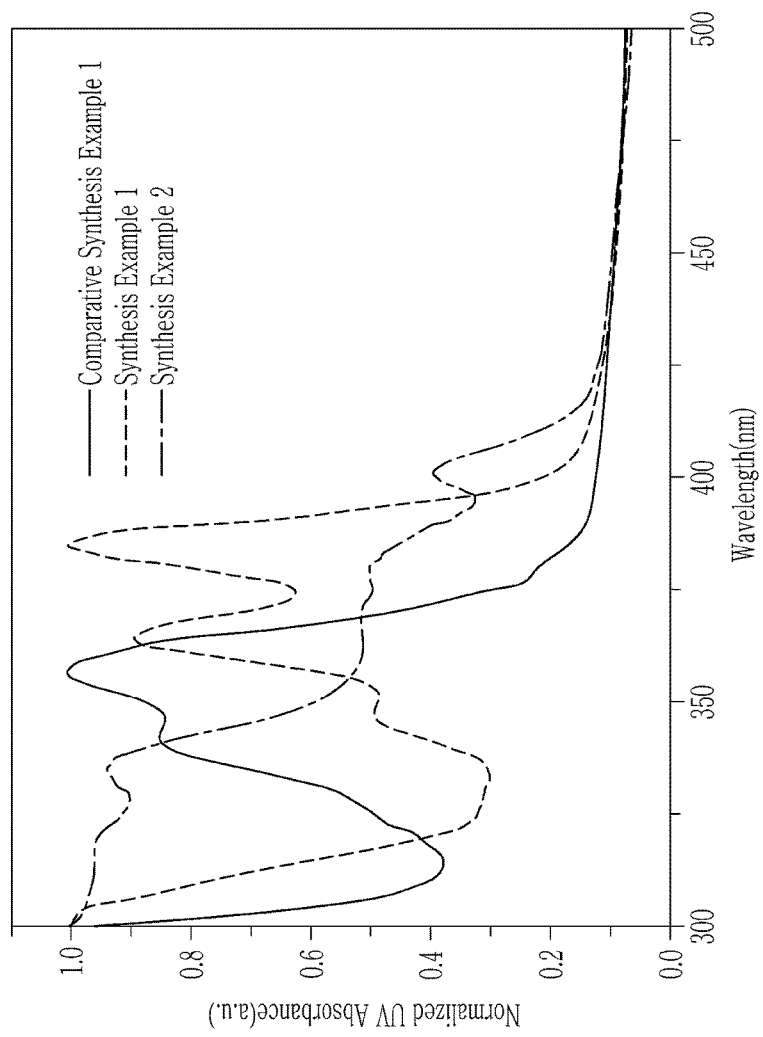
FIG. 3 is a graph showing light absorption characteristics of the compounds obtained in Synthesis Example 1, Synthesis Example 2, and Comparative Synthesis Example 1 in each thin film.

The results are shown in FIGS. 2 and 3.

FIG. 2 is a graph showing light absorption characteristics of the compounds obtained in Synthesis Example 1, Synthesis Example 2, and Comparative Synthesis Example 1 in each solution, and FIG. 3 is a graph showing light absorption characteristics of the compounds obtained in Synthesis Example 1, Synthesis Example 2, and Comparative Synthesis Example 1 in each thin film.

Referring to FIGS. 2 and 3, the compounds according to Synthesis Examples 1 and 2 and Comparative Synthesis Example 1 all showed satisfactory light absorption characteristics.

Evaluation 2: PL Characteristics

PL characteristics of the compounds according to Synthesis Examples 1 and 2 and Comparative Synthesis Example 1 in a solution state and in a thin film state were evaluated.

The PL characteristics of the compounds according to Synthesis Examples 1 and 2 and Comparative Synthesis Example 1 in a solution state were evaluated by respectively dissolving the compounds in THF with a concentration of 10-5 M and using a PL spectrometer (Perkin-Elmer luminescence spectrometer LS50 (Xenon flash tube)), and the light absorption characteristics of the compounds in a thin film state were evaluated by respectively vacuum-depositing the compounds on a glass substrate and using a PL spectrometer (Perkin-Elmer luminescence spectrometer LS50 (Xenon flash tube)).

Figure 4:
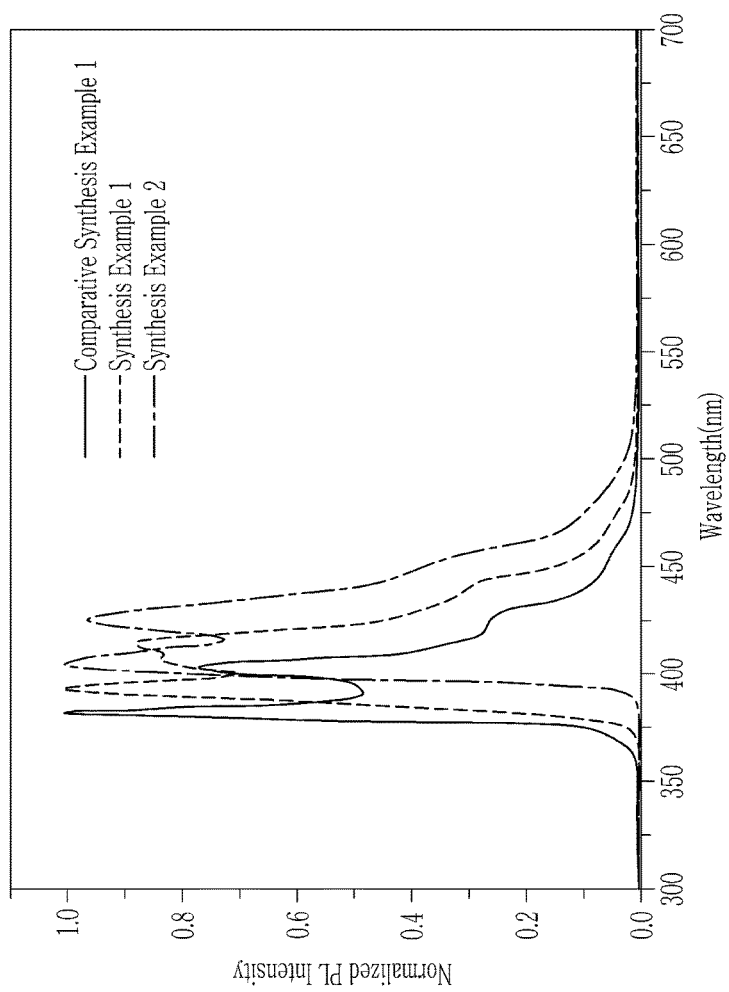
FIG. 4 is a graph showing PL characteristics of the compounds obtained in Synthesis Example 1, Synthesis Example 2, and Comparative Synthesis Example 1 in each solution.
Figure 5:
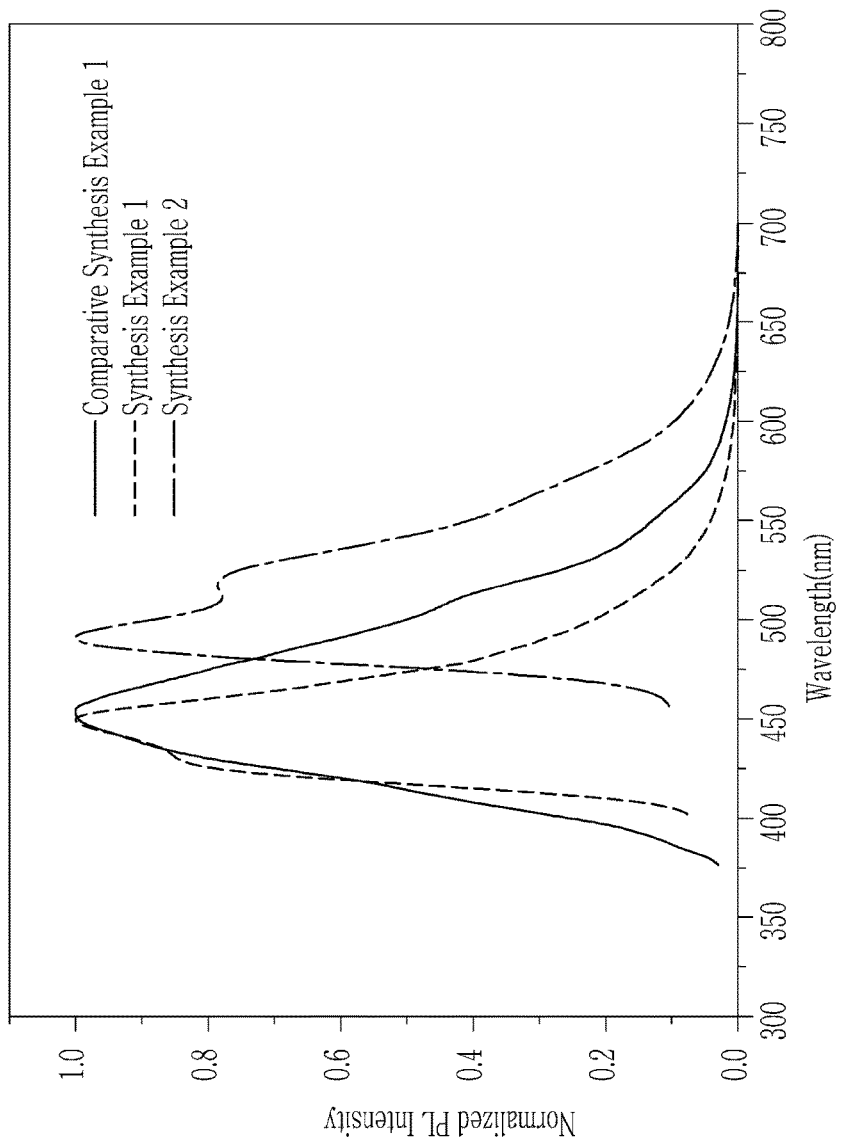
FIG. 5 is a graph showing PL characteristics of the compounds obtained in Synthesis Example 1, Synthesis Example 2, and Comparative Synthesis Example 1 each thin film.

The results are shown in FIGS. 4 and 5.

FIG. 4 is a graph showing PL characteristics of the compounds obtained in Synthesis Example 1, Synthesis Example 2, and Comparative Synthesis Example 1 in each solution, and FIG. 5 is a graph showing PL characteristics of the compounds obtained in Synthesis Example 1, Synthesis Example 2, and Comparative Synthesis Example 1 each thin film.

Referring to FIGS. 4 and 5, the compounds according to Synthesis Examples 1 and 2 and Comparative Synthesis Example 1 emitted light of a particular wavelength in a visible ray region. In particular, referring to FIG. 5, the compounds according to Synthesis Example 1 and Comparative Synthesis Example 1 emitted light in a blue region, the compound according to Synthesis Example 2 emitted light in a light blue (sky blue) region, and accordingly, as the compounds emitted light of a different wavelength depending on a hetero atom included in the core.

Manufacture of Organic Light Emitting Diode

Example 1

A hole auxiliary layer was formed by sputtering ITO to be 500 nm thick on a glass substrate and sequentially depositing 2-TNATA to be 60 nm thick and NPB to be 15 nm thick thereon. Subsequently, a 35 nm-thick light emitting layer was formed on the hole auxiliary layer by depositing the compound according to Synthesis Example 1. On the light emitting layer, an electron auxiliary layer was formed by sequentially depositing Alq3 to be 15 nm thick and LiF to be 1 nm thick. Subsequently, on the electron auxiliary layer, Al was deposited to be 200 nm thick to manufacture an organic light emitting diode.

Example 2

An organic light emitting diode was manufactured according to the same method as Example 1 except for using TPBi instead of Alq3.

Example 3

An organic light emitting diode was manufactured according to the same method as Example 1 except for using the compound according to Synthesis Example 2 instead of the compound according to Synthesis Example 1.

Comparative Example 1

An organic light emitting diode was manufactured according to the same method as Example 1 except for using the compound according to Comparative Synthesis Example 1 instead of the compound according to Synthesis Example 1.

Evaluation 3: Diode Evaluation

Electric characteristics, light emitting characteristics, and color characteristics of the organic light emitting diodes according to Examples 1 to 3 and Comparative Example 1 were evaluated.

Table 1 shows electric characteristics, light emitting characteristics, and color characteristics of the organic light emitting diodes according to Examples 1 to 3 and Comparative Example 1 (current density: 10 mA/cm$^2$).

TABLE 1

| | Driving voltage (Operating Voltage) (V) | Turn-on voltage (Turn-on Voltage) (V) | Luminous efficiency (cd/A) | Power efficiency (lm/W) | External quantum efficiency (%) | Color coordinate (x, y) | Thin film EL$_{max}$ (nm) |
|---|---|---|---|---|---|---|---|
| Example 1 | 7.9 | 4.5 | 3.24 | 1.41 | 3.21 | 0.15, 0.13 | 457 |
| Example 2 | 7.5 | 4.4 | 3.53 | 1.65 | 3.94 | 0.15, 0.12 | 453 |
| Example 3 | 6.5 | 3.1 | 3.99 | 2.18 | 1.64 | 0.23, 0.50 | 490 |
| Comparative Example 1 | 8.4 | 5.4 | 2.11 | 0.87 | 2.03 | 0.16, 0.14 | 455 |

Figure 6:
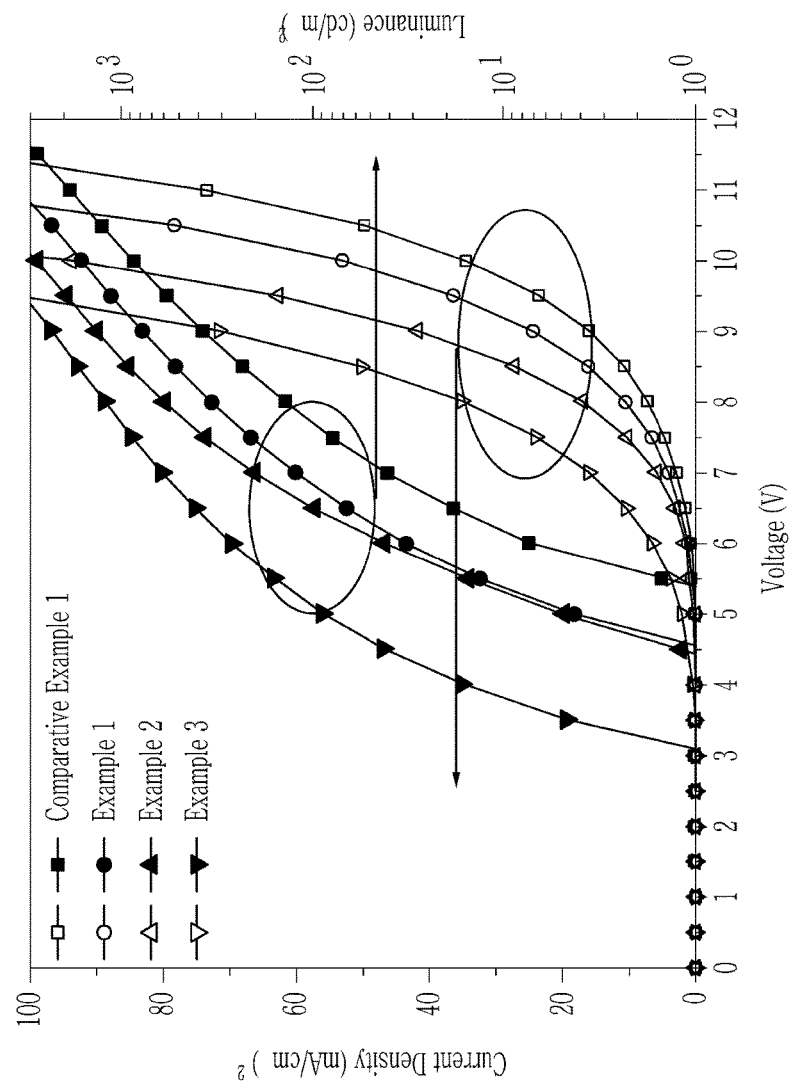
FIG. 6 is a graph showing current characteristics and luminance of the organic light emitting diodes according to Example 1 to Example 3 and Comparative Example 1.
Figure 7:
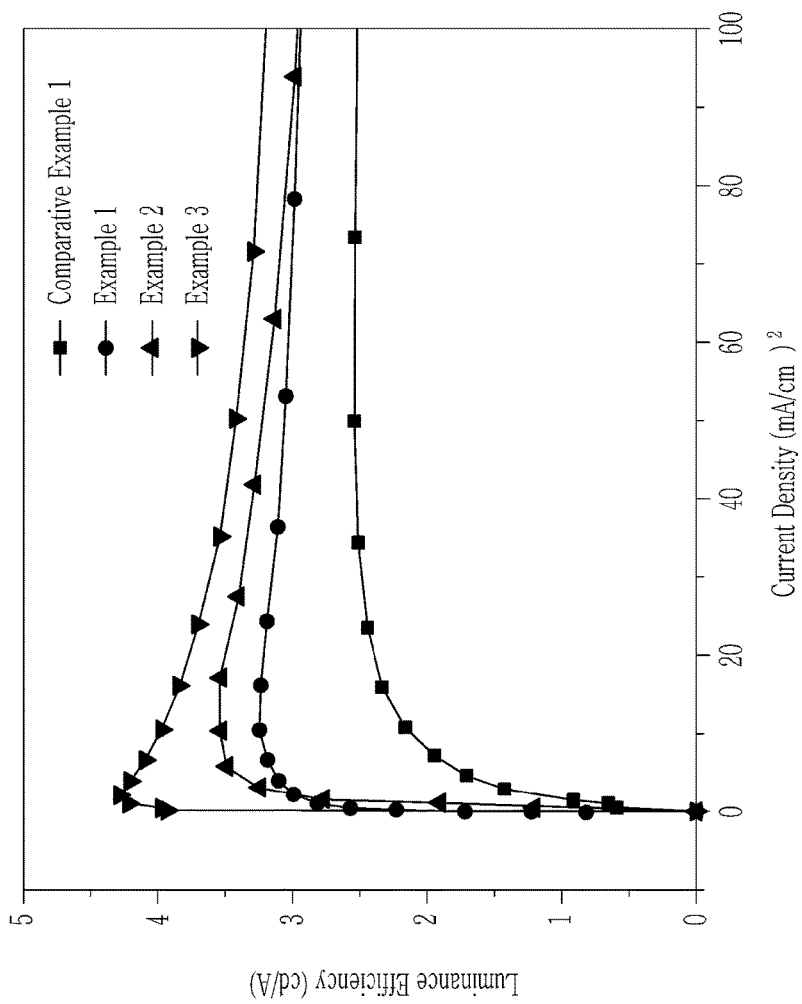
FIG. 7 is a graph showing luminous efficiency of the organic light emitting diodes according to Example 1 to Example 3 and Comparative Example 1.
Figure 8:
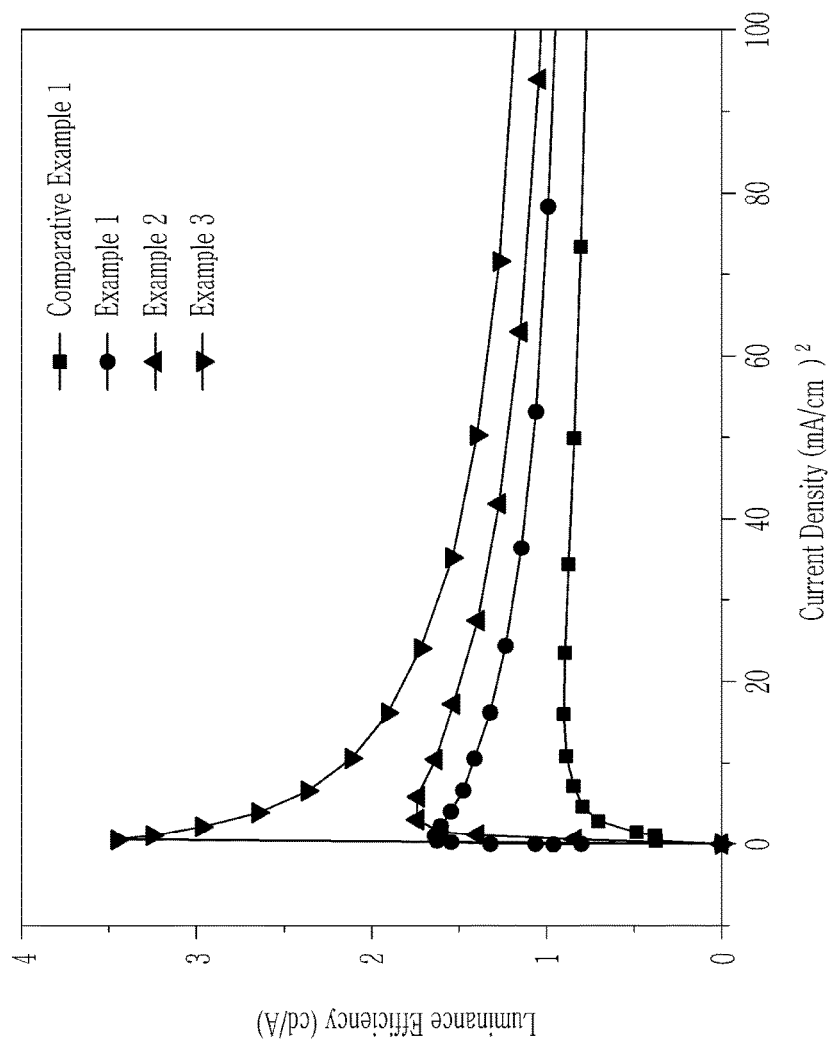
FIG. 8 is a graph showing power efficiency of the organic light emitting diodes according to Example 1 to Example 3 and Comparative Example 1.
Figure 9:
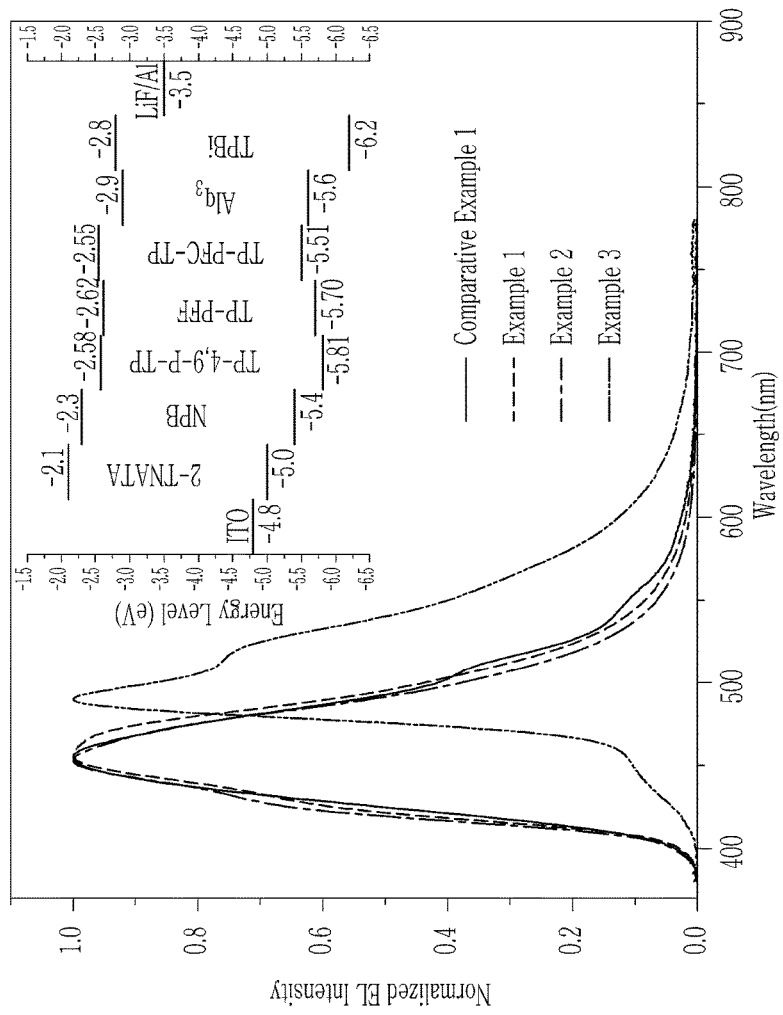
FIG. 9 is a graph showing photoluminescence characteristics of the organic light emitting diodes according to Example 1 to Example 3 and Comparative Example 1.
Figure 10:
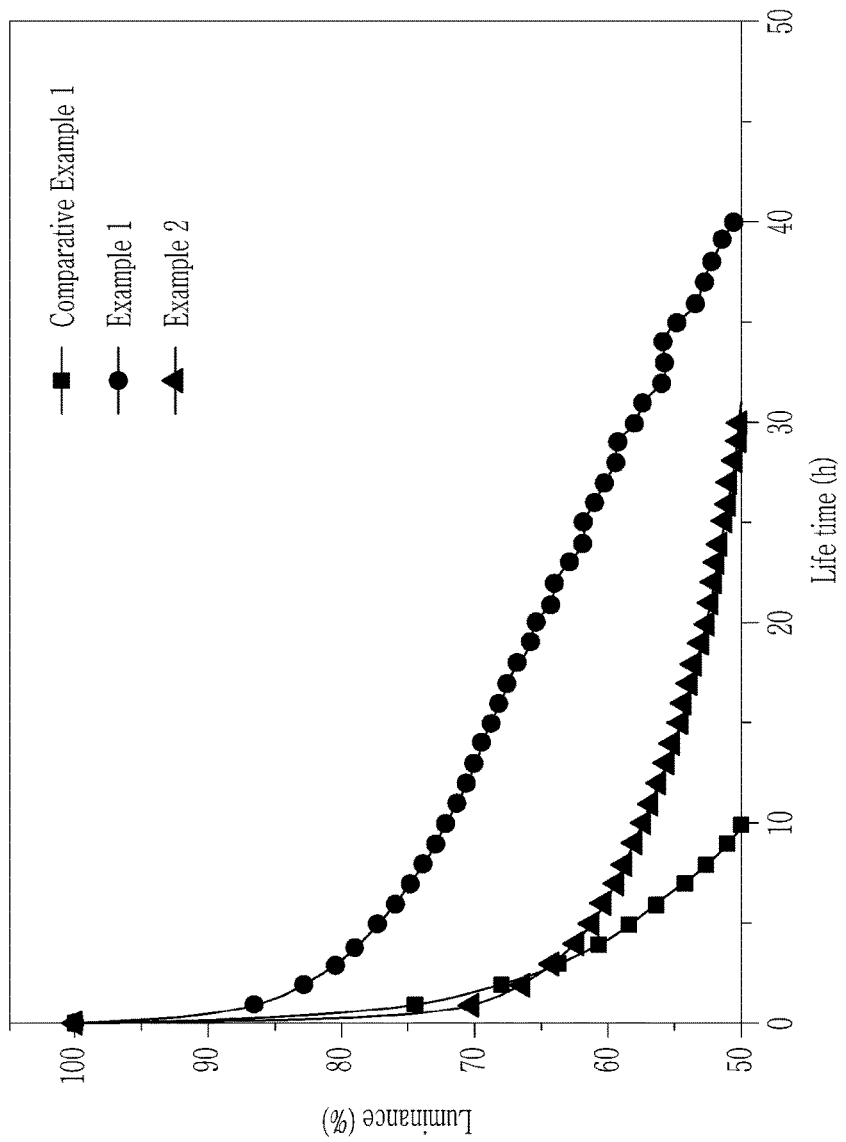
FIG. 10 is a graph showing life-span characteristics of the organic light emitting diodes according to Example 1, Example 2, and Comparative Example 1.

FIG. 6 is a graph showing current characteristics and luminance of the organic light emitting diodes according to Example 1 to Example 3 and Comparative Example 1, FIG. 7 is a graph showing luminous efficiency of the organic light emitting diodes according to Example 1 to Example 3 and Comparative Example 1, FIG. 8 is a graph showing power efficiency of the organic light emitting diodes according to Example 1 to Example 3 and Comparative Example 1, FIG. 9 is a graph showing photoluminescence characteristics of the organic light emitting diodes according to Example 1 to Example 3 and Comparative Example 1, and FIG. 10 is a graph showing life-span characteristics of the organic light emitting diodes according to Example 1, Example 2, and Comparative Example 1.

Referring to Table 1 and FIGS. 6 to 10, the organic light emitting diodes according to Examples 1 to 3 and Comparative Example 1 showed sufficient electric characteristics, light emitting characteristics, life-span characteristics, and color characteristics.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

What is claimed is:

1. An organic compound represented by Chemical Formula 3:

[Chemical Formula 3]

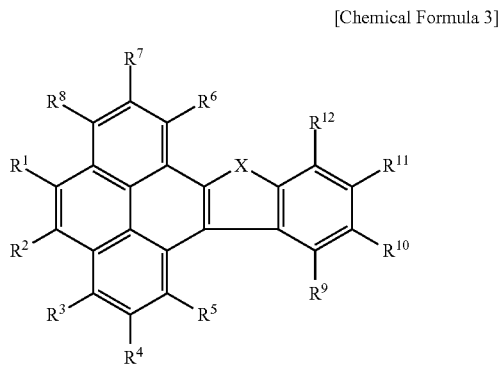

wherein, in Chemical Formula 3, $R^1$ to $R^8$ are independently hydrogen, deuterium, a substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, provided that $R^6$ to $R^8$ are the same, $R^9$ to $R^{12}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, and X is —$CR^aR^b$—, wherein $R^a$ and $R^b$ are independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heteroaryl group or Ra and Rb are linked with each other to form a fused ring, wherein at least one of $R^1$ and $R^2$ is substituted or unsubstituted amine group, a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, at least one of $R^9$ to $R^{12}$ is a substituted or unsubstituted C1 to C30 alkyl group, a substituted or unsubstituted C6 to C30 aryl group, a substituted or unsubstituted C2 to C30 heteroaryl group, a substituted or unsubstituted fluorenyl group, or a combination thereof, and X is —$CR^aR^b$—, wherein $R^a$ and $R^b$ are independently hydrogen, deuterium, a substituted or unsubstituted amine group, a substituted or unsubstituted C1 to C30 alkyl group, a substituted or unsubstituted C6 to C30 aryl group or a substituted or unsubstituted C2 to C30 heteroaryl group, or $R^a$ and $R^b$ are linked with each other to form a fused ring.

2. The organic compound of claim 1, wherein the organic compound is represented by one of Chemical Formulas 4-1 to 4-38

[Chemical Formula 4-1]

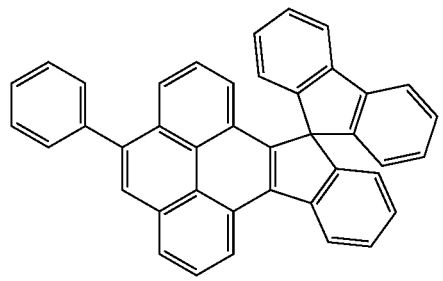

[Chemical Formula 4-2]

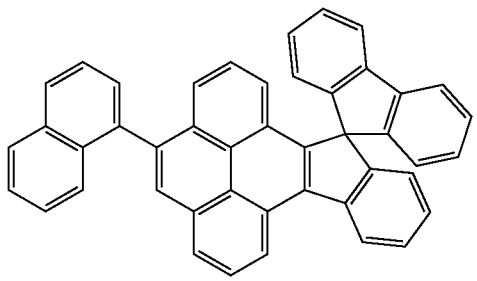

[Chemical Formula 4-3]

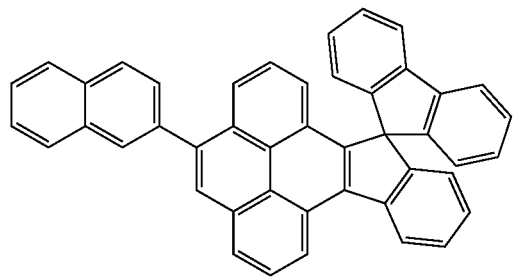

[Chemical Formula 4-4]

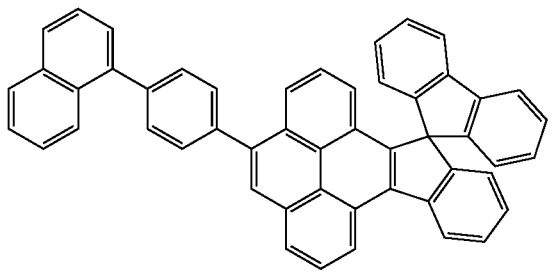

-continued
[Chemical Formula 4-5]
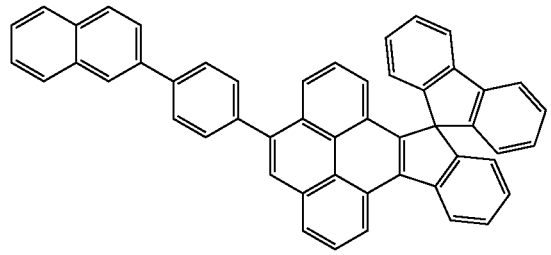
[Chemical Formula 4-6]
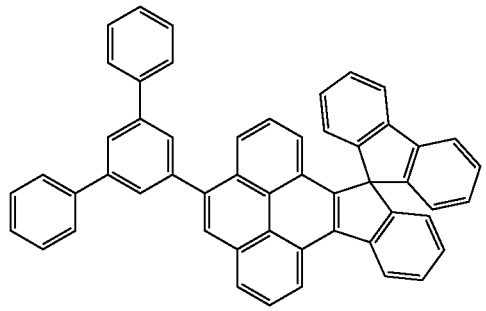
[Chemical Formula 4-7]
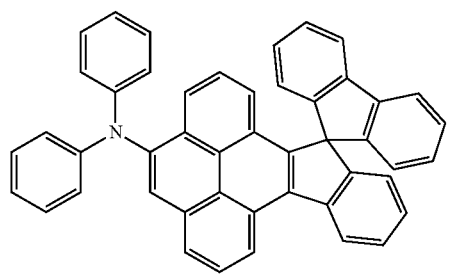
[Chemical Formula 4-8]
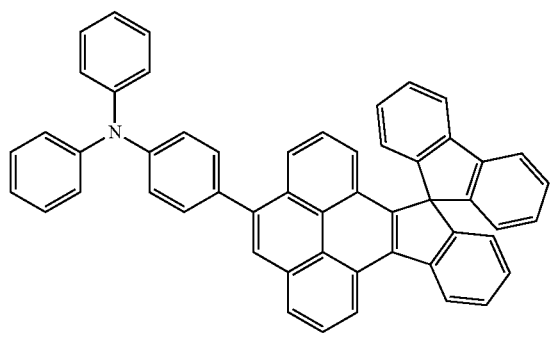
[Chemical Formula 4-9]
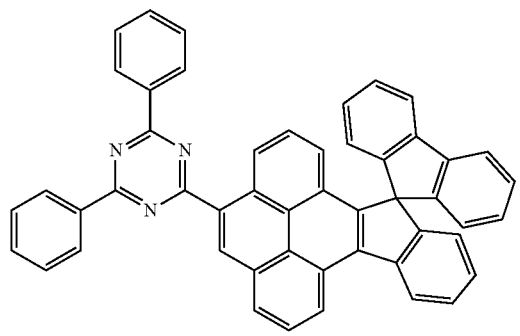
[Chemical Formula 4-10]
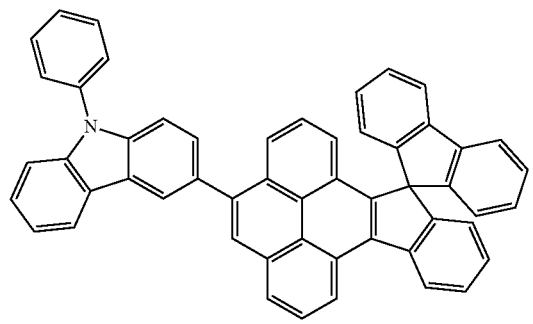
[Chemical Formula 4-11]
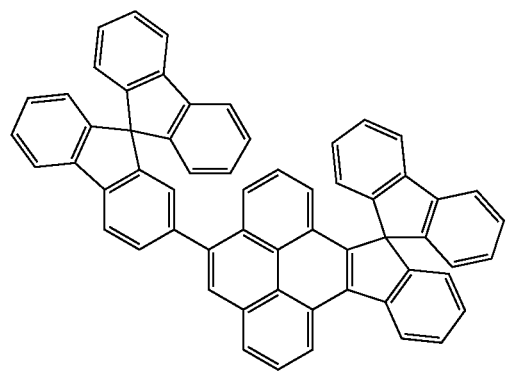
[Chemical Formula 4-12]
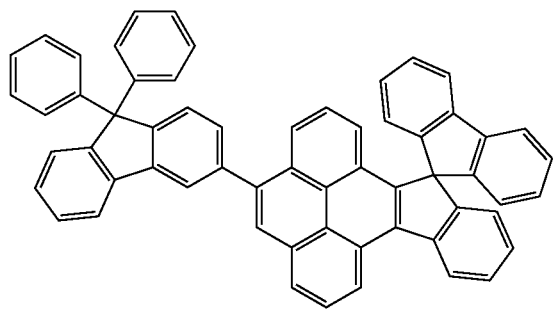

-continued
[Chemical Formula 4-13]
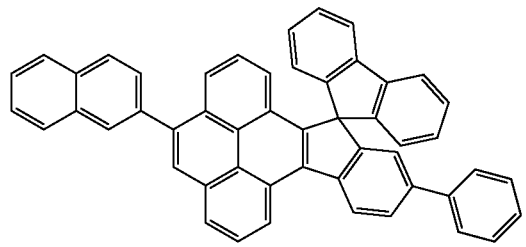
[Chemical Formula 4-14]
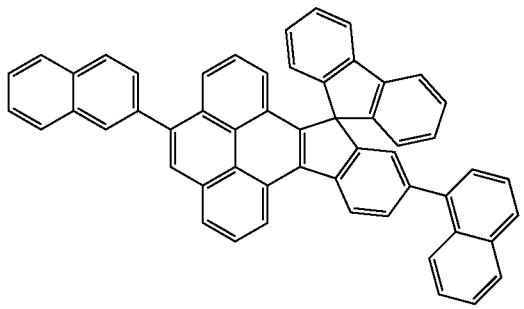
[Chemical Formula 4-15]
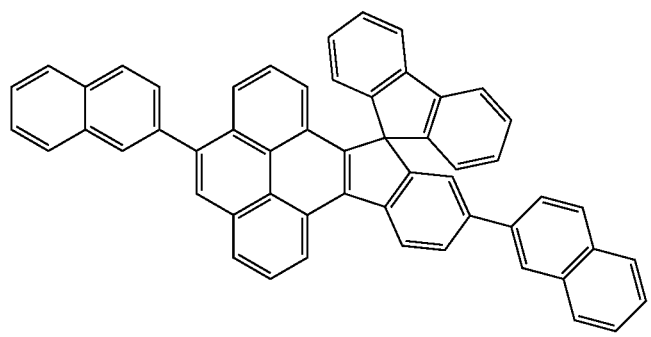
[Chemical Formula 4-16]
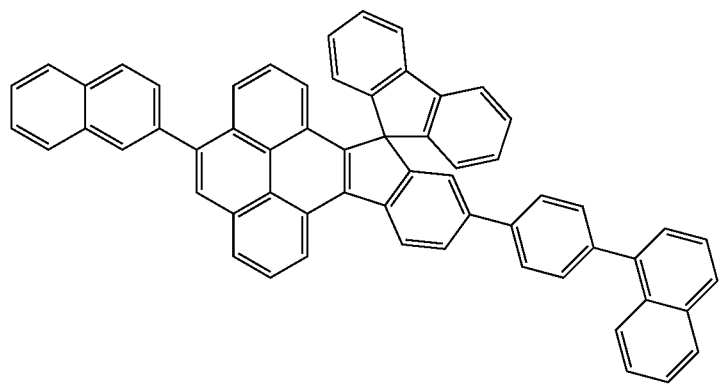
[Chemical Formula 4-17]
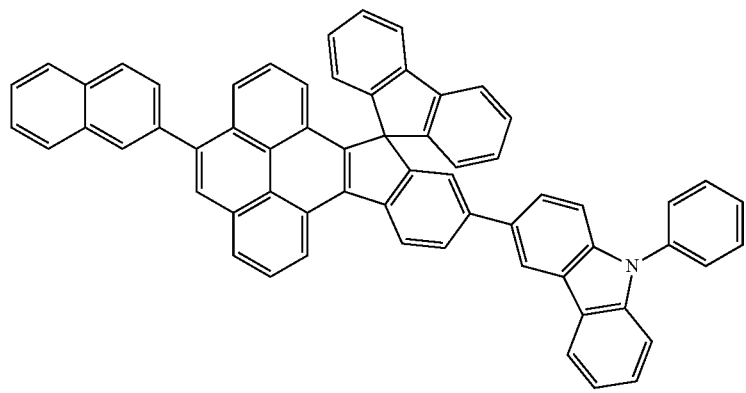

[Chemical Formula 4-18]
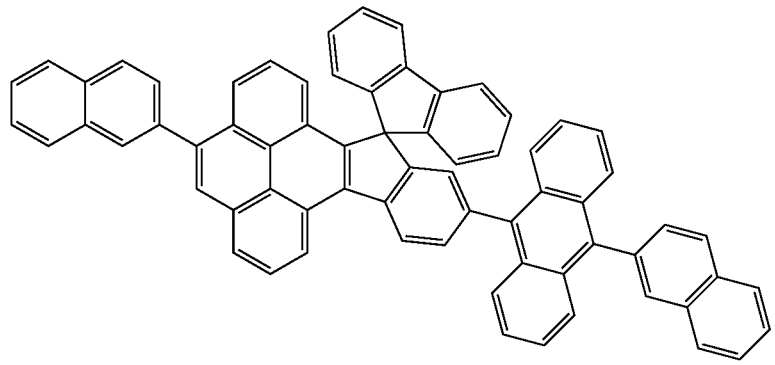
[Chemical Formula 4-19]
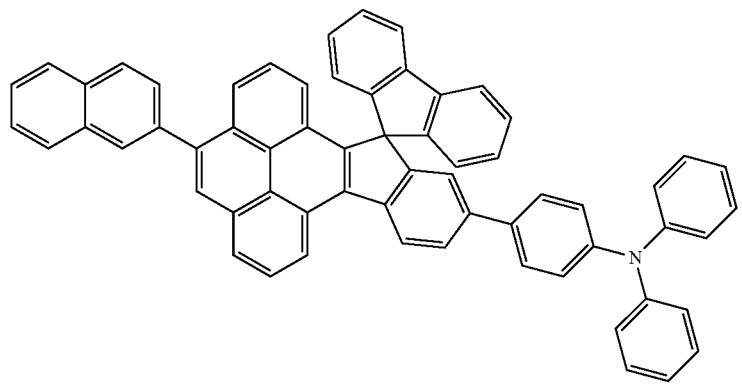
[Chemical Formula 4-20]
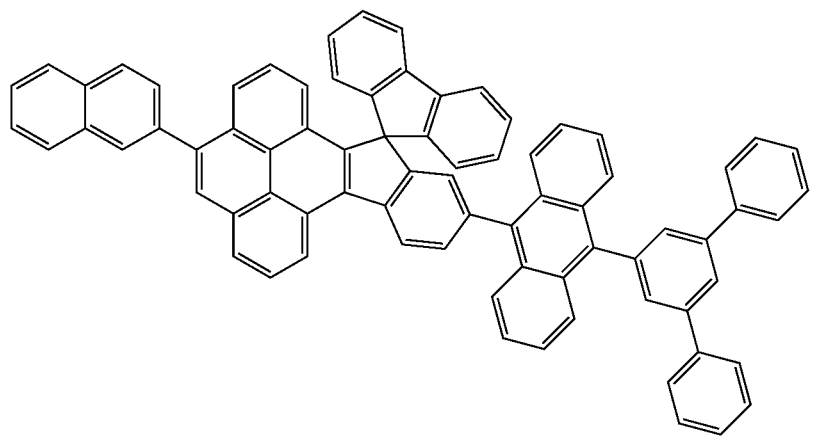
[Chemical Formula 4-21]
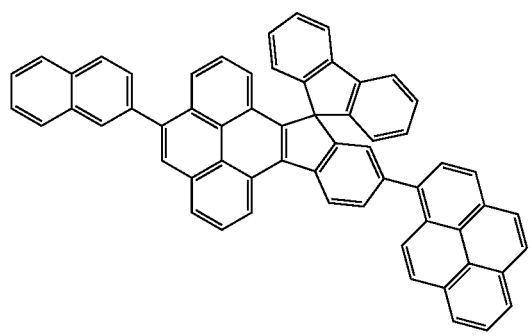
[Chemical Formula 4-22]
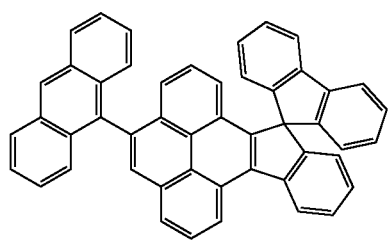

-continued

[Chemical Formula 4-23]

[Chemical Formula 4-24]

[Chemical Formula 4-25]

[Chemical Formula 4-26]

[Chemical Formula 4-27]

[Chemical Formula 4-28]

[Chemical Formula 4-29]

[Chemical Formula 4-30]

[Chemical Formula 4-31]
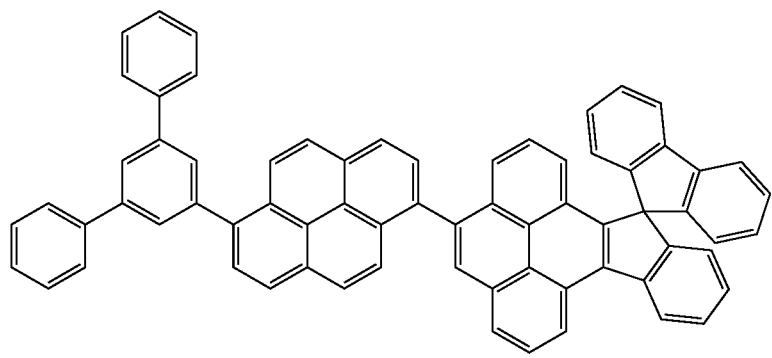
[Chemical Formula 4-32]
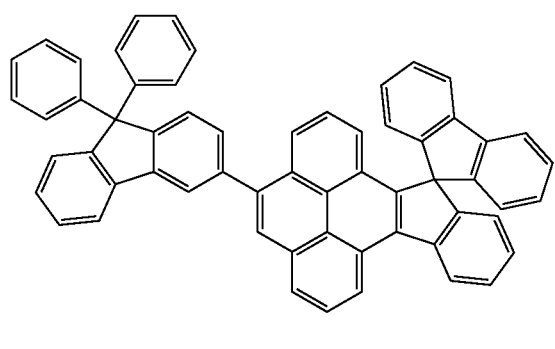
[Chemical Formula 4-33]
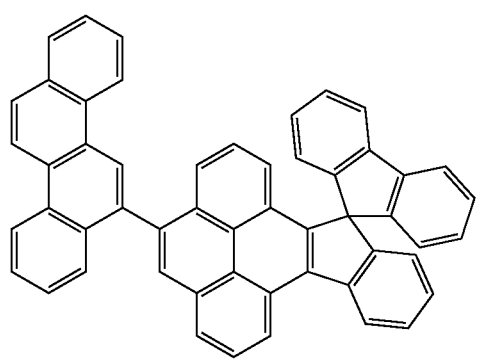
[Chemical Formula 4-34]
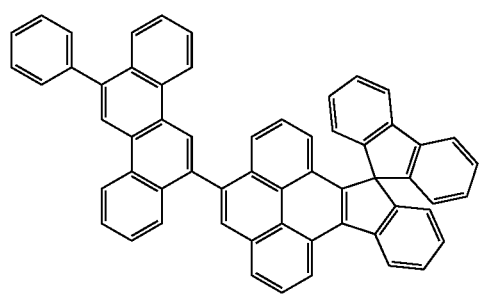
[Chemical Formula 4-35]
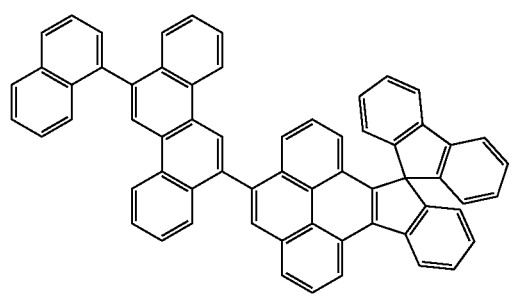
[Chemical Formula 4-36]
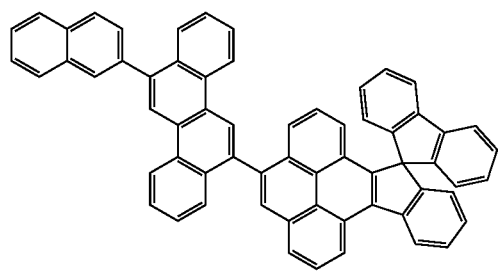
[Chemical Formula 4-37]
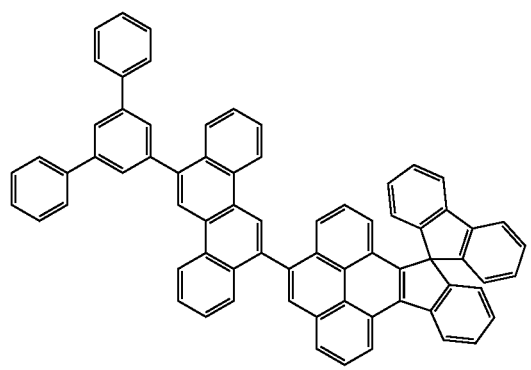

[Chemical Formula 4-38]

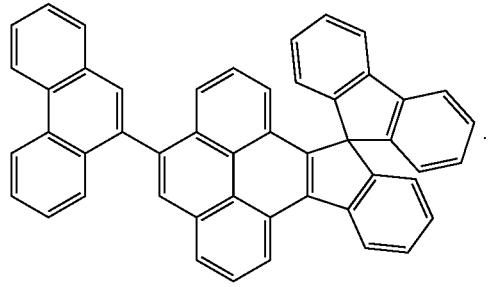

3. An organic optoelectronic device, comprising
an anode, a cathode, and at least one organic layer disposed between the anode and the cathode,
wherein at least one layer of the organic layer includes the organic compound of claim 1.

4. The organic optoelectronic device of claim 3, wherein the organic layer is selected from a light emitting layer, a hole transport layer, a hole injection layer, an electron transport layer, an electron injection layer, a hole blocking layer, and a combination thereof.

5. The organic optoelectronic device of claim 4, wherein the organic compound is included in the light emitting layer.

6. The organic optoelectronic device of claim 3, wherein the organic optoelectronic device is selected from an organic photoelectric device, an organic light emitting diode, an organic solar cell, an organic transistor, an organic photo conductor drum, and an organic memory device.

7. The organic optoelectronic device of claim 6, wherein the organic optoelectronic device is an organic light emitting diode.

8. A display device comprising the organic light emitting diode of claim 7.

* * * * *